(12) United States Patent
O'Connor et al.

(10) Patent No.: US 11,406,608 B2
(45) Date of Patent: Aug. 9, 2022

(54) HISTONE ACETYLTRANSFERASE ACTIVATORS AND COMPOSITIONS AND USES THEREOF

(71) Applicant: The Trustees of Columbia University in the City of New York, New York, NY (US)

(72) Inventors: Owen Anthony O'Connor, Scarsdale, NY (US); Jennifer Effie Amengual, Scarsdale, NY (US); Donald W. Landry, New York, NY (US); Ottavio Arancio, New York, NY (US); Luigi Scotto, Stamford, CT (US); Shixian Deng, White Plains, NY (US); Rosa Purgatorio, Bari (IT); Joie Fiorito, Floral Park, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/870,584

(22) Filed: May 8, 2020

(65) Prior Publication Data
US 2020/0330410 A1    Oct. 22, 2020

Related U.S. Application Data

(62) Division of application No. 15/655,583, filed on Jul. 20, 2017, now Pat. No. 10,653,648.

(60) Provisional application No. 62/364,480, filed on Jul. 20, 2016.

(51) Int. Cl.
| | |
|---|---|
| *A61K 31/16* | (2006.01) |
| *A61K 31/167* | (2006.01) |
| *A61K 31/5377* | (2006.01) |
| *A61K 31/44* | (2006.01) |
| *A61K 31/381* | (2006.01) |
| *A61K 45/06* | (2006.01) |
| *A61K 31/535* | (2006.01) |
| *A61K 31/4409* | (2006.01) |
| *A61K 31/495* | (2006.01) |
| *A61K 31/505* | (2006.01) |
| *A61K 31/18* | (2006.01) |
| *A61K 31/4035* | (2006.01) |
| *A61K 31/4453* | (2006.01) |
| *A61K 38/15* | (2006.01) |

(52) U.S. Cl.
CPC ............ *A61K 31/167* (2013.01); *A61K 31/18* (2013.01); *A61K 31/381* (2013.01); *A61K 31/4035* (2013.01); *A61K 31/44* (2013.01); *A61K 31/4409* (2013.01); *A61K 31/4453* (2013.01); *A61K 31/495* (2013.01); *A61K 31/505* (2013.01); *A61K 31/535* (2013.01); *A61K 31/5377* (2013.01); *A61K 38/15* (2013.01); *A61K 45/06* (2013.01)

(58) Field of Classification Search
CPC .................................................... A61K 31/167
See application file for complete search history.

(56) References Cited

U.S. PATENT DOCUMENTS

| | | |
|---|---|---|
| 10,653,648 B2 | 5/2020 | O'Connor et al. |
| 2009/0076155 A1 | 3/2009 | Kundu et al. |
| 2010/0144885 A1 | 6/2010 | Pandey |
| 2010/0166781 A1 | 7/2010 | Setiadi et al. |
| 2013/0121919 A1 | 5/2013 | Feng et al. |
| 2018/0140722 A1 | 5/2018 | Willis et al. |

FOREIGN PATENT DOCUMENTS

| | | |
|---|---|---|
| WO | WO-2004/053140 A2 | 6/2004 |
| WO | WO-2010047714 | 4/2010 |
| WO | WO-2011/072243 | 6/2011 |
| WO | WO-2012088420 | 6/2012 |
| WO | WO-2013153940 | 10/2013 |
| WO | WO-2015/153410 A1 | 10/2015 |
| WO | WO-2018017858 | 1/2018 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
West, et al. J. Clin Invest. 2014; 124(1):30-39.*
Ahmad et al., "Understanding histone deacetylases in the cancer development and treatment: an epigenetic perspective of cancer chemotherapy," DNA Cell Biol., 31 (Suppl. 1), pp. S62-S71 (2012).
Archer and Hodint, "Histone acetylation and cancer," Current Opinion in Genetics & Development, 9(2), pp. 171-174 (1999).
Balasubramanyam et al., "Small molecule modulators of histone acetyltransferase p300," J. Biol. Chem., 278(21), pp. 19134-19140 (2003).
Bassett, et al., "The Role of Dietary Histone Deacetylases (HDACs) Inhibitors in Health and Disease", Nutrients, 6:4273-4301, Oct. 15, 2014 (29 pages).
Berge et al., "Pharmaceutical Salts," J. Pharm. Sci., 66(1), pp. 1-19 (1977).
Cohen et al., "Histone Modifiers in Cancer: Friends or Foes?" Genes & Cancer, 2(6), pp. 631-647 (2011).
Dal Piaz et al., "The Identification of a Novel Natural Activator of p300 Histone Acetyltranferase Provides New Insights into the Modulation Mechanism of this Enzyme," ChemBioChem., 11(6), pp. 818-827 (2010).

(Continued)

*Primary Examiner* — Shawquia Jackson
(74) *Attorney, Agent, or Firm* — Wilmer Cutler Pickering Hale and Dorr LLP

(57) ABSTRACT

The invention provides pharmaceutical compositions and methods for treating cancer, neurodegenerative disorders, conditions associated with accumulated amyloid-beta peptide deposits, Tau protein levels, and/or accumulations of alpha-synuclein by administering a HAT modulator and a HDAC modulator to a subject.

24 Claims, 37 Drawing Sheets

(56) References Cited

OTHER PUBLICATIONS

Dekker and Haisma, "Histone acetyl transferases as emerging drug targets," Drug Discovery Today, 14, pp. 942-948 (2009).
European Extended Search Report issued in European Patent Application No. EP17831884.6, dated Jun. 23, 2020 (13 pages).
European Supplemental Search Report issued in European Patent Application No. 17831884.6, dated Mar. 3, 2020 (15 pages).
Guan et al., "HDAC2 negatively regulates memory formation and synaptic plasticity," Nature, 459, pp. 55-60 (2009).
Guo et al., "Epigenetic mechanisms of amyloid-β production in anisomycin-treated SH-SY5Y cells," Neuroscience, 194, pp. 272-281 (2011).
International Search Report and Written Opinion for PCT Application No. PCT/US17/43115 dated Oct. 10, 2017 (10 pages).
Kilgore et al. "Inhibitors of Class 1 Histone Deacetylases Reverse Contextual Memory Deficits in a Mouse Model of Alzheimer's Disease," Neuropsychopharmacology, 35, pp. 870-880 (2009).
Kimura et al., "A decade of histone acetylation: marking eukaryotic chromosomes with specific codes," J. Biochem., 138(6), pp. 647-662 (2005).
Lane and Chabner, "Histone deacetylase inhibitors in cancer therapy," J. Clin. Oncol., 27(32), pp. 5459-5468 (2009).
Lee and Workman, "Histone acetyltransferase complexes: one size doesn't fit all," Nat. Rev. Mol. Cell Biol., 8(4), pp. 284-295 (2007).
Majid, et al., "BTG3 tumor suppressor gene promoter demethylation, histone modification and cell cycle arrest by genistein in renal cancer", Carcinogenesis, 30(4):662-670, 2009 (9 pages).
Mantelingu et al., "Activation of p300 histone acetyltransferase by small molecules altering enzyme structure: probed by surface-enhanced Raman spectroscopy," J. Phys. Chem. B, 111(17), pp. 4527-4534 (2007).
Mariani, "Targeting Cancer Cells—More Pathways, More Inhibitors, More Trials: Highlights of 9th Annual Drug Discovery Technology World Congress; Aug. 8-13, 2004; Boston, Massachusetts," Med. Gen. Med., 6(4), 6 pages (2004).
Marmorstein, "Structure of histone acetyltransferases," J. Mol. Biol., 311, pp. 433-444 (2001).
Pasqualucci et al., "Inactivating mutations of acetyltransferase genes in B-cell lymphoma," Author Manuscript, published in final edited form as: Nature, 471(7337), pp. 189-195 (2011).
Roth et al., "Histone Acetyltransferases," Annual Review of Biochemistry, 70, 81-120 (2001).
Singh et al., "Inhibition of class I histone deacetylases in non-small cell lung cancer by honokiol leads to suppression of cancer cell growth and induction of cell death in vitro and in vivo," Epigenetics, 8(1), pp. 54-65 (2013).
Sjölander and Urbaniczky, "Integrated fluid handling system for biomolecular interaction analysis," Anal. Chem., 63, pp. 2338-2345 (1991).
Sweatt, "Neuroscience. Epigenetics and cognitive aging," Science, 328(5979), pp. 701-702 (2010).
Woan, et al., "Modulation of antigen-presenting cells by HDAC inhibitors: implications in autoimmunity and cancer", Immunology and Cell Biology, 90:55-65, 2012, published online Nov. 22, 2011 (11 pages).
Yuan et al., "Involvement of p300/CBP and epigenetic histone acetylation in TGF-β1-mediated gene transcription in mesangial cells," American Journal of Physiology—Renal Physiology, 304(5), pp. F601-F613 (2013).

\* cited by examiner

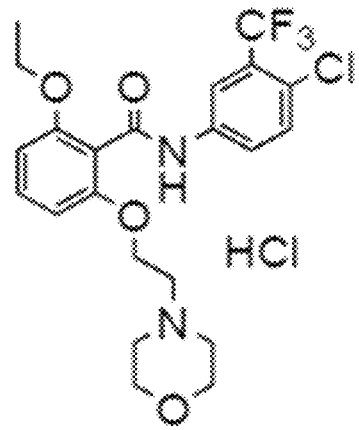
JF2
Chemical Formula: C₂₂H₂₆Cl₂F₃N₂O₄
Molecular Weight: 509.35
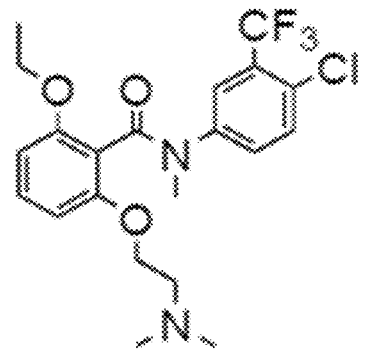
RP72
Chemical Formula: C₂₁H₂₄ClF₃N₂O₃
Molecular Weight: 444.88
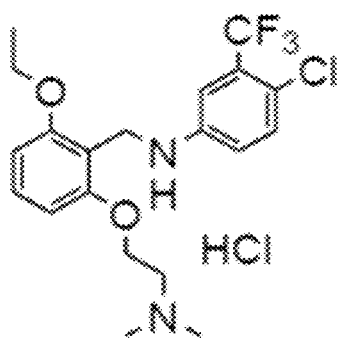
RP52
Chemical Formula: C₂₀H₂₄ClF₃N₂O₂
Molecular Weight: 416.87
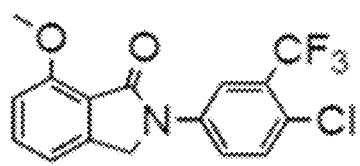
RP14
Chemical Formula: C₁₆H₁₁ClF₃NO₂
Molecular Weight: 341.71
FIG. 1

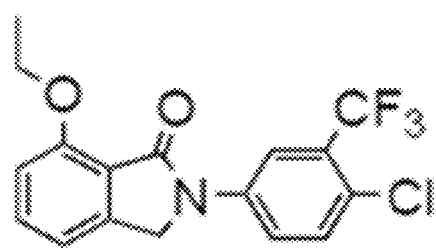
RP58
Chemical Formula: C₁₇H₁₅ClF₃NO₂
Molecular Weight: 355.74
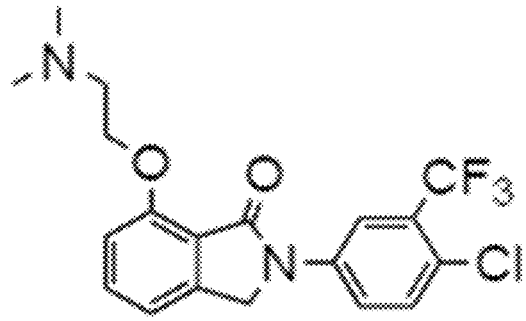
RP59
Chemical Formula: C₁₉H₁₈ClF₃N₂O₂
Molecular Weight: 398.81
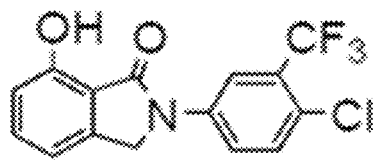
RP23
Chemical Formula: C₁₅H₉ClF₃NO₂
Molecular Weight: 327.69
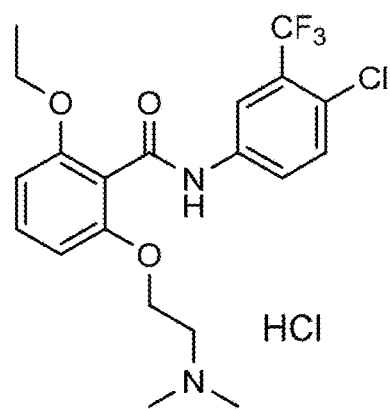
YF2·HCl
Chemical Formula: C₂₀H₂₃Cl₂F₃N₂O₃
Molecular Weight: 467.31
FIG. 1 cont.

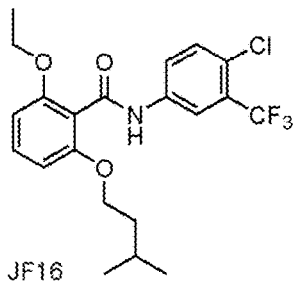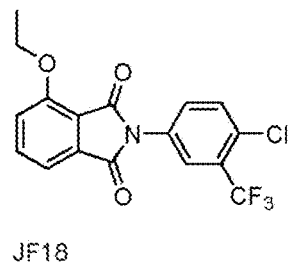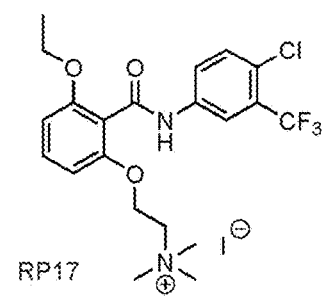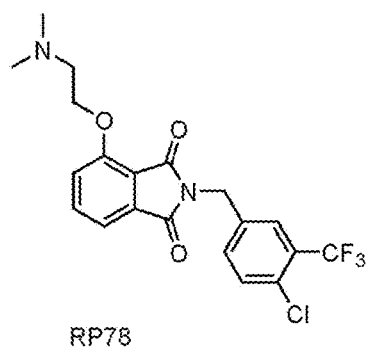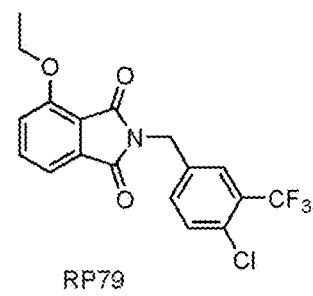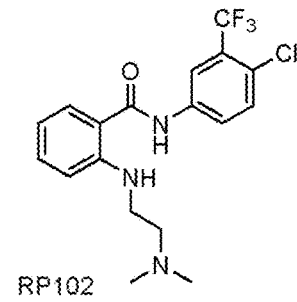
FIG. 1 cont.

FIG. 9A
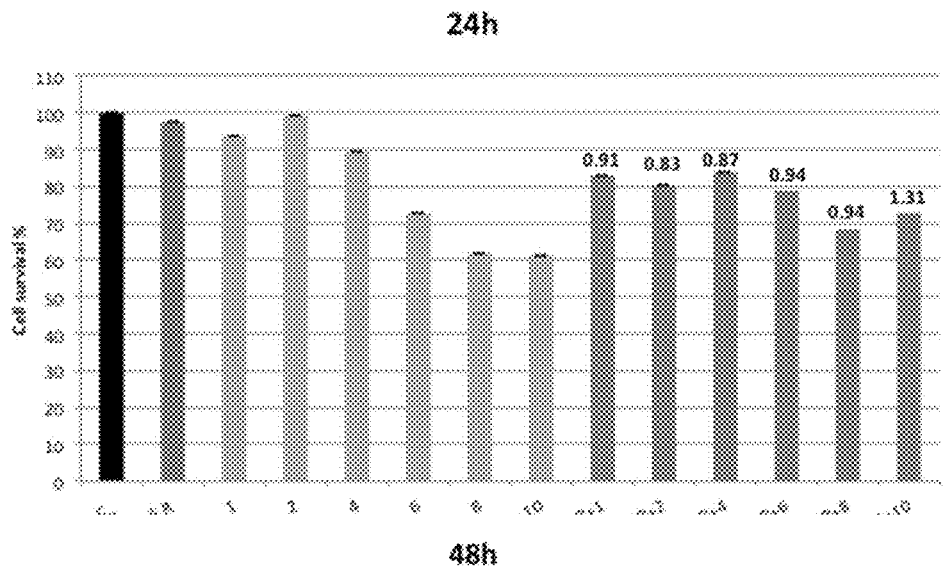
FIG. 9B
FIG. 9C
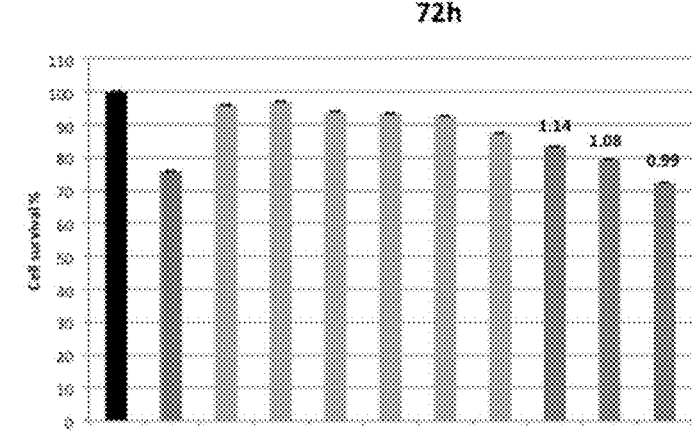

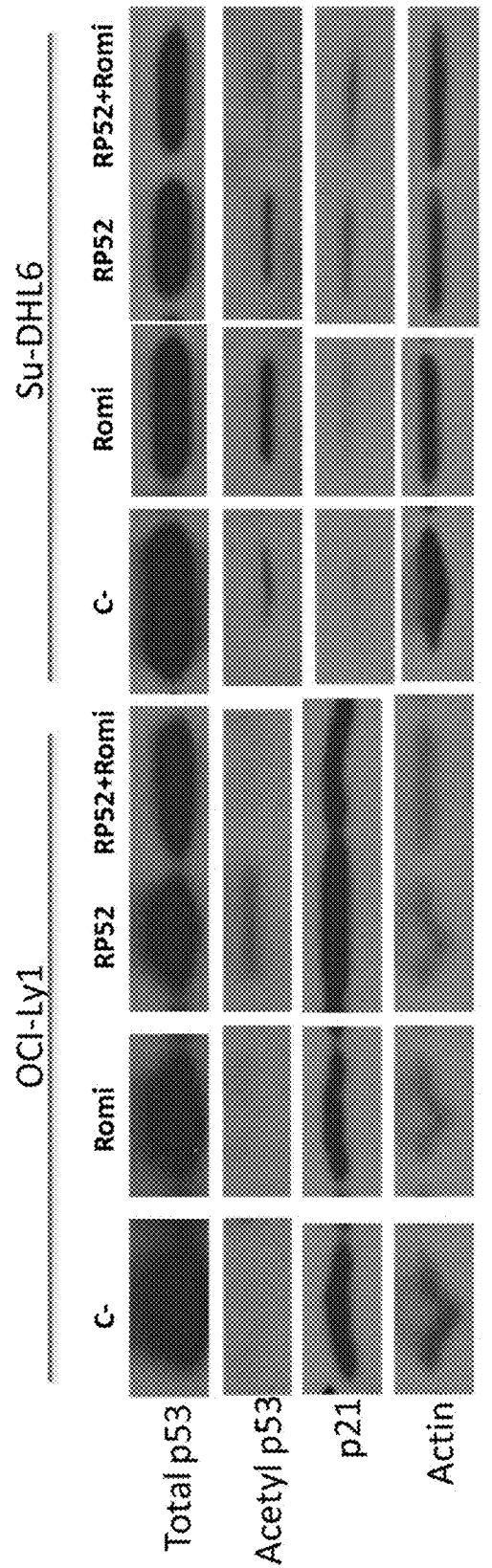

| JF1/YF2 (μM) Romidepsin (nM) | | JF1 72hrs | | | YF2 72hrs | | |
|---|---|---|---|---|---|---|---|
| | | 2 | 2.5 3 | 3 4 | 6 | 7 | 8 |
| SUDHL-10 | 1 | -5.1 | 13.1 | 31.9 | 20.5 | 24.8 | 22.8 |
| | 1.25 | 8.0 | 20.2 | 50.6 | 38.3 | 38.4 | 28.0 |
| | 1.5 | 18.9 | 27.9 | 69.7 | 47.0 | 41.1 | 28.6 |
| Toledo | 1 | 21.1 | 25.5 | 37.5 | 30.3 | 38.1 | 44.1 |
| | 1.25 | 32.3 | 39.6 | 44.8 | 40.4 | 42.9 | 43.1 |
| | 1.5 | 28.6 | 33.7 | 36.7 | 30.5 | 31.5 | 30.6 |
| SUDHL-2 | 1 | 12.3 | 13.9 | 13.6 | 38.3 | 22.8 | 43.3 |
| | 1.25 | 25.2 | 24.4 | 26.0 | 52.6 | 42.2 | 40.2 |
| | 1.5 | 26.1 | 24.2 | 26.1 | 38.7 | 31.2 | 27.9 |
| SUDHL-6 | 1 | -8.6 | -9.9 | -11.6 | 7.9 | 13.8 | 21.1 |
| | 1.25 | -1.5 | 15.1 | 27.2 | 25.5 | 26.5 | 26.1 |
| | 1.5 | 25.1 | 35.7 | 40.6 | 29.2 | 30.4 | 29.1 |
| Farage | 1 | -.8 | 6.7 | -1.7 | | | |
| | 1.25 | 26.6 | 23.3 | 12.6 | | | |
| | 1.5 | 17.8 | 9.4 | 16.5 | | | |
| Ly-1 | 1 | -7.6 | 18.3 | 32.5 | | | |
| | 1.25 | 7.2 | 58.7 | 35 | | | |
| | 1.5 | 27.4 | 61.7 | 38.3 | | | |
| Pfeiffer | 2 | 7.4 | 11.6 | 12.8 | -0.3 | 4.3 | 4.7 |
| | 2.5 | 6.1 | 14.2 | 11.8 | 6.5 | 10.5 | 4.3 |
| | 3 | 8.1 | 11.9 | 21.0 | 12.2 | 10.9 | 8.5 |
| RIVA | 1 | -6.4 | 0.2 | 4.9 | | | |
| | 1.25 | -13.7 | 6.2 | 20.7 | | | |
| | 1.5 | -24.7 | 9.6 | 13.1 | | | |
| Ly-7 | 1 | -11.7 | -8.5 | 3.1 | 20.1 | 13.8 | 20.1 |
| | 1.25 | -13.0 | -2.1 | 11.5 | 28.7 | 27.5 | 30.6 |
| | 1.5 | -8.9 | 4.5 | 24.9 | 55.0 | 45.0 | 46.0 |
| Z-138 | 1 | 1.4 | -9.3 | -17.5 | 20.4 | 6.4 | 5.6 |
| | 1.25 | 13.4 | 1.2 | -5.7 | 33.2 | 16.8 | 31.3 |
| | 1.5 | 29.1 | 31 | 15.4 | | 72.5 | 62.9 |
| MT1 | 1 | 15.9 | 14 | 20.2 | | | |
| | 1.25 | 22.3 | 26.6 | 26.8 | | | |
| | 1.5 | 4.4 | 6.4 | 7.7 | | | |
| MT2 | 1 | -8.3 | -6.4 | -0.3 | | | |
| | 1.25 | -10.6 | -9.5 | -6.7 | | | |
| | 1.5 | -2.1 | -10.7 | -3.7 | | | |
| TLom1 | 1 | 7.5 | 1.3 | -4.7 | | | |
| | 1.25 | 10.1 | 11.5 | 15.7 | | | |
| | 1.5 | 22.6 | 26.5 | 21.6 | | | |
| H9 | 1 | 11 | 10.7 | 10.3 | | | |
| | 1.25 | 18.5 | 16.9 | 19.7 | | | |
| | 1.5 | 16.6 | 15.5 | 19.3 | | | |

FIG. 27

HISTONE ACETYLTRANSFERASE ACTIVATORS AND COMPOSITIONS AND USES THEREOF

CROSS REFERENCE TO RELATED APPLICATION

This application is a divisional of U.S. patent application Ser. No. 15/655,583, filed on Jul. 20, 2017, which claims the benefit of U.S. Provisional Patent Application No. 62/364,480, filed on Jul. 20, 2016 and entitled "Histone Acetyltransferase Activators and Uses Thereof," the disclosure of which is hereby incorporated by reference in its entirety for all purposes.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Modulation of the acetylation state of histones, transcription factors, and other regulatory proteins is known to influence their activity within cancer and inflammatory cells. The acetylation state of a protein is controlled by the activity of two main groups of enzymes, histone deacetylases (HDAC) and histone acetyl transferases (HAT). The HDAC removes acetyl-groups while the HATs transfer acetyl-groups to the protein of interest.

Classically, modulation of acetylation status is known to influence the condensation of chromatin. In cancer, histones are deacetylated maintaining a condensed chromatin structure, and a transcriptionally silenced state. This transcriptional inactivation is mediated by HDACs which remove acetyl groups from histone tails, maintain a condensed chromatic structure. Inhibitors of HDACs help maintain transcriptionally active chromatin, theoretically allowing for expression of tumor suppressor genes. One observation that has evolved is that histones are not the only targets of acetylation. It is now accepted that post-translational acetylation of intracellular proteins such as tumor suppressors (p53) and oncogenes (Bcl6) plays a critical role in influencing their activity. It has been established that there is a network of proteins and enzymes that can be modified by acetylation, now collectively referred to as the acetylome.

Cognitive neurodegenerative disorders are characterized by synaptic dysfunction, cognitive abnormalities, and/or the presence of inclusion bodies throughout the CNS containing, for example, but not limited to native beta-amyloid fragments, native and phosphorylated Tau, native and phosphorylated alpha-synuclein, lipofuscin, cleaved TARDBP (TDB-43), in various percentages and in relation to the specific disease.

Alzheimer's disease (AD) is an irreversible neurodegenerative disease characterized by memory loss, synaptic dysfunction and accumulation of amyloid β-peptides (Aβ). The pathogenesis of AD is believed to be caused by high levels and aggregation of amyloid-β (Aβ) in the brain. Aβ has been found to impair memory by reducing acetylation of specific histone lysines important for memory formation. Histones are proteins that closely associate with DNA molecules and play an important role in gene transcription.

Currently available therapies for AD are palliative and do not cure the disease. Cholinesterase inhibitors such as Razadyne® (galantamine), Exelon® (rivastigmine), Aricept® (donepezil), and Cognex® (tacrine) have been prescribed for early stages of Alzheimer's disease, and may temporarily delay or prevent progression of symptoms related to AD. However, as AD progresses, the brain loses less acetylcholine, thereby rendering cholinesterase inhibitors unproductive as treatment for AD. Namenda® (memantine), an N-methyl D-aspartate (NMDA) antagonist, is also prescribed to treat moderate to severe Alzheimer's disease; however only temporary benefits are realized.

Histone Acetyltransferases (HATs) are involved in histone acetylation (leading to gene activation), chromosome decondensation, DNA repair and non-histone substrate modification. The post-translational acetylation status of chromatin is governed by the competing activities of two classes of enzymes, HATs and HDACs. The potential of inhibiting HDACs to counteract neurodegenerative disorders has been widely explored (*Curr Drug Targets CNS Neurol Disord*, 2005. 4(1): p. 41-50; hereby incorporated by reference in its entirety). HATs, however, have been investigated to a lesser extent. HAT activators have been reported, but many are neither soluble nor membrane permeant, which makes them poor candidates for therapeutics. CTPB and CTB are HAT activators that are insoluble and membrane-impermeable (*J Phys Chem B*, 2007. 111(17): p. 4527-34; *J Biol Chem*, 2003. 278(21): p. 19134-40; each hereby incorporated by reference in its entirety). Nemorosone is another HAT activator (*Chembiochem.* 11(6): p. 818-27; hereby incorporated by reference in its entirety). However, these compounds suffer from unfavorable physicochemical characteristics for use in CNS diseases.

There is a need for novel HAT activators. There is also a need for novel treatments for a variety of disease states for which HAT activity is implicated. There is a further need for novel and effective treatments for neurodegenerative diseases, neurological disorders and cancers. In particular, there is a continuing need for treatment of dementia and memory loss associated with Alzheimer's disease. There is also a continuing need for treatment of cancer.

SUMMARY OF THE INVENTION

In one aspect, the invention is directed to pharmaceutical compositions and methods for treating cancer in a subject in need thereof. The pharmaceutical compositions may comprise a HAT activator and a HDAC inhibitor and the methods may comprise administering to a subject a HAT activator and a HDAC inhibitor.

In one embodiment of the pharmaceutical compositions disclosed herein, the HAT activator has a structure of formula (I),

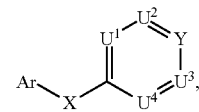

wherein,

Ar is

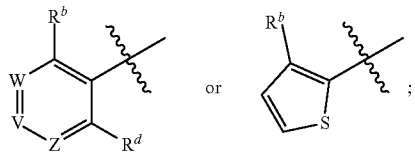

$R^a$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$;

$R^b$ is H, OH, halogen, $C_1$-$C_6$-alkyl, —($C_1$-$C_6$-alkyl)$CO_2$—($C_1$-$C_6$-alkyl), $C_1$-$C_6$-haloalkyl, $C_2$-$C_6$-alkenyl, $C_3$-$C_8$-cycloalkyl, $C_2$-$C_6$-heteroalkyl, $C_3$-$C_8$-heterocycloalkyl, aryl, heteroaryl, O—($C_1$-$C_6$-alkyl), O—($C_1$-$C_6$-alkyl)$CO_2$—($C_1$-$C_6$-alkyl), O—($C_1$-$C_6$-haloalkyl), O—($C_3$-$C_8$-cycloalkyl), O—($C_2$-$C_6$-alkenyl), O—($C_3$-$C_8$-heterocycloalkyl), N($R^{10}$)—($C_1$-$C_6$-alkyl), N($R^{10}$)—($C_1$-$C_6$-alkyl)$CO_2$—($C_1$-$C_6$-alkyl), N($R^{10}$)—($C_3$-$C_8$-cycloalkyl), SH, S—($C_1$-$C_6$-alkyl), S—($C_1$-$C_6$-alkyl)$CO_2$—($C_1$-$C_6$-alkyl), $SO_2$—($C_1$-$C_6$-alkyl), $SO_2$—($C_1$-$C_6$-alkyl)$CO_2$—($C_1$-$C_6$-alkyl), O—($C_2$-$C_6$-alkyl)-N($R^{10}$)$_2$, O—($C_2$-$C_6$-alkyl)-N($R^{10}$)$_3^+$halogen$^-$, O—($C_3$-$C_8$-cycloalkyl)-N($R^{10}$)$_2$, N($R^{10}$)—($C_2$-$C_6$-alkyl)-N($R^{10}$)$_2$, —($C_1$-$C_6$-alkyl)-N($R^{10}$)$_2$, —($C_1$-$C_6$-alkyl)-$R^3$, O—($C_1$-$C_6$-alkyl)-$R^3$, O—($C_3$-$C_8$-cycloalkyl)-$R^3$, N($R^{10}$)—($C_1$-$C_6$-alkyl)-$R^3$, O-aryl, or O-heteroaryl;

$R^c$ is H, —($C_1$-$C_6$-alkyl), O—($C_1$-$C_6$-alkyl), C(=O)NH-phenyl, wherein phenyl is substituted with one or more halo or haloalkyl;

$R^d$ is H, OH, halogen, $C_1$-$C_{16}$-alkyl, $C_1$-$C_{16}$-haloalkyl, O—($C_3$-$C_8$-cycloalkyl), O—($C_3$-$C_8$-heterocycloalkyl), O—($C_2$-$C_6$-alkenyl), O—($C_1$-$C_6$-alkyl), O—($C_1$-$C_6$-alkyl)-phenyl, O—($C_2$-$C_6$-alkyl)-N($R^{10}$)$_2$, O—($C_2$-$C_6$-alkyl)-N($R^{10}$)$_3^+$halogen$^-$, —($C_1$-$C_6$-alkyl)-$R^3$, O—($C_1$-$C_6$-alkyl)-$R^3$, O—S($C_1$-$C_6$-alkyl), N($R^{10}$)—($C_1$-$C_6$-alkyl)-$R^3$, —N($R^{10}$)—($C_1$-$C_6$-alkyl), —N($R^{10}$)—($C_2$-$C_6$-alkenyl), —N($R^{10}$)—($C_3$-$C_8$-cycloalkyl), —N($R^{10}$)—($C_3$-$C_8$-heterocycloalkyl), N($R^{10}$)—($C_2$-$C_6$-alkyl)-N($R^{10}$)$_2$, —($C_1$-$C_6$-alkyl)-N($R^{10}$)$_2$, S—($C_2$-$C_6$-alkyl)-N($R^{10}$)$_2$, $OCH_2$C(O)O($C_1$-$C_6$-alkyl), O-aryl, N-aryl, O-heteroaryl, or N-heteroaryl;

$U^1$-$U^4$ are independently N or $CR^a$, wherein $U^1$-$U^4$ are not each N;

V is a bond, N or $CR^c$;

W and Z are independently N or $CR^1$;

X is —CO—, —CON($R^{10}$)—, —CON($R^{10}$)($CH_2$)$_n$—, —($CH_2$)$_n$CON($R^{10}$)—, —($CH_2$)$_n$CON($R^{10}$)($CH_2$)$_n$—, —SON($R^{10}$)—, —SON($R^{10}$)($CH_2$)$_n$—, —$SO_2$N($R^{10}$)—, —$SO_2$N($R^{10}$)($CH_2$)$_n$—, —N($R^{10}$)C(=O)N($R^{10}$)—, —N($R^{10}$)CO—, —N($R^{10}$)CO($CH_2$)$_n$—, or —N($R^{10}$)CO($CH_2$)$_n$—, —($CH_2$)$_n$N($R^{10}$)—, —C=N—; or

Ar and X together form

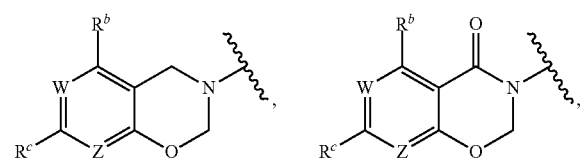

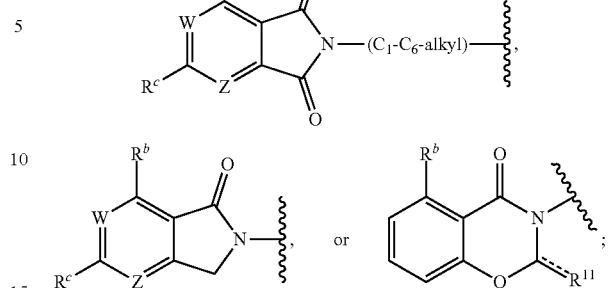

Y is a bond, N or $CR^2$;

$R^1$ is H, halogen, O—($C_1$-$C_6$-alkyl), O—($C_2$-$C_6$-alkyl)N($R^{10}$)$_2$;

$R^2$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$;

$R^3$ is cycloalkylamino, optionally containing a heteroatom selected from N($R^{10}$), O and S;

$R^{10}$ is independently H, —($C_1$-$C_4$-alkyl), —($C_1$-$C_4$-haloalkyl), —($C_3$-$C_8$-cycloalkyl), —($C_3$-$C_8$-heterocycloalkyl), aryl or heteroaryl;

═══ is a double bond and $R^{11}$ is O; or

═══ is a single bond and $R^{11}$ is —($C_1$-$C_6$-alkyl), —($C_1$-$C_6$-alkyl)-N($R^{10}$)$_2$, or —($C_1$-$C_6$-alkyl)-N($R^{10}$)$_3^+$halogen; and each n is independently an integer from 1-4, or a pharmaceutically acceptable salt thereof.

In one embodiment of the pharmaceutical compositions disclosed herein, the HAT activator is selected from the group consisting of:

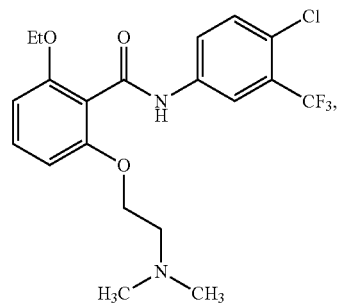

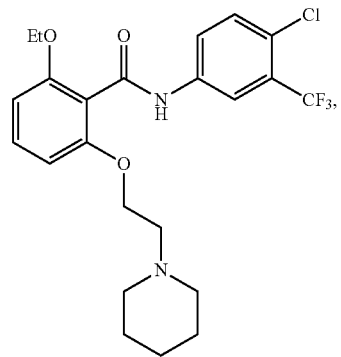 [SMILES: CCOc1cccc(OCCN2CCCCC2)c1C(=O)Nc1ccc(Cl)c(C(F)(F)F)c1]

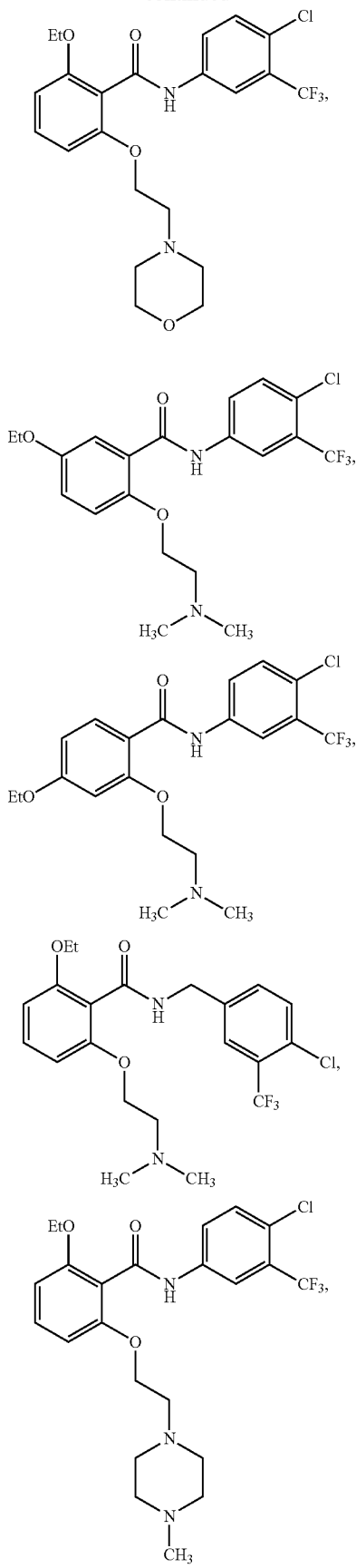
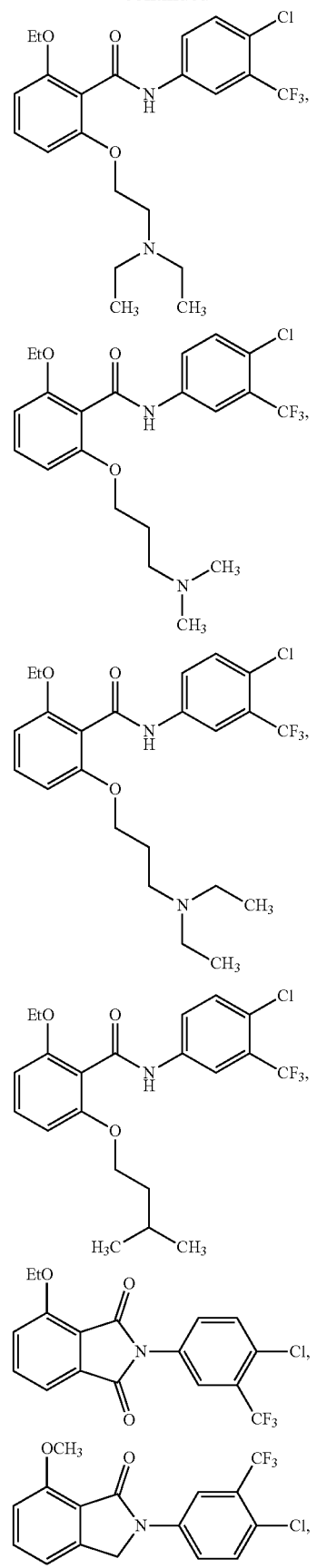

7
-continued
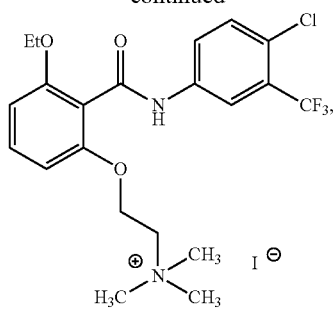
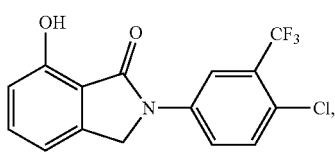
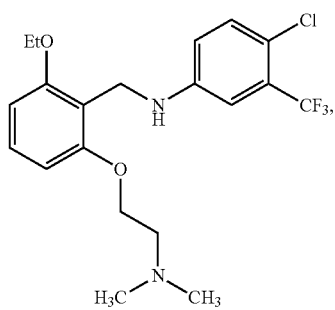
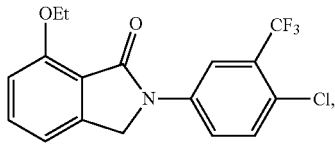
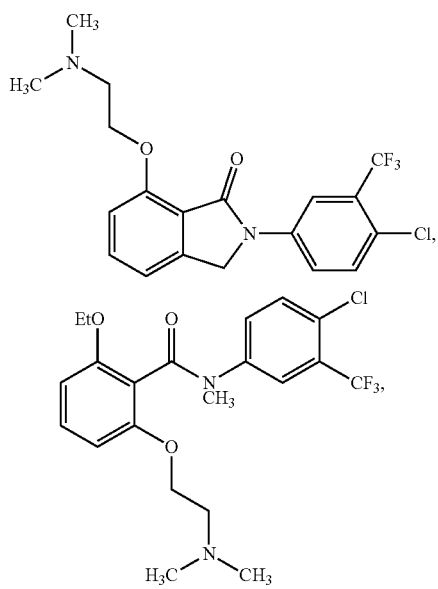
8
-continued
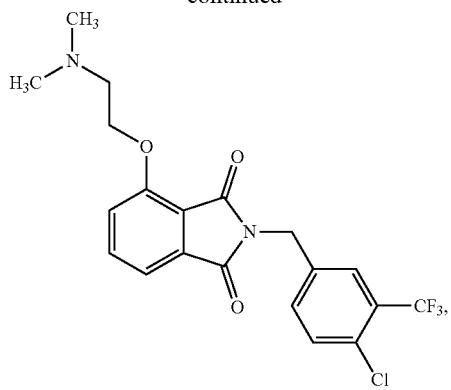
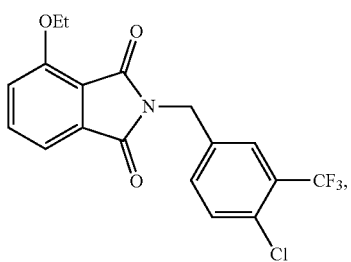
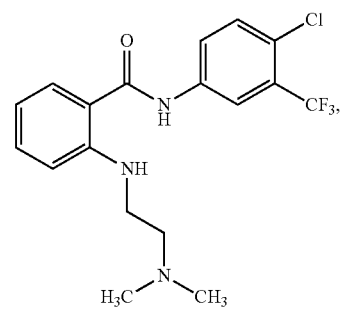
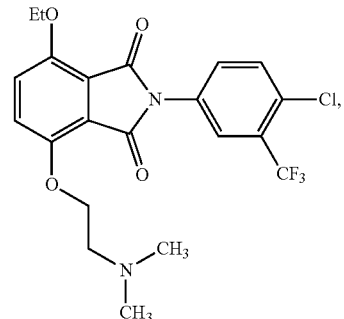
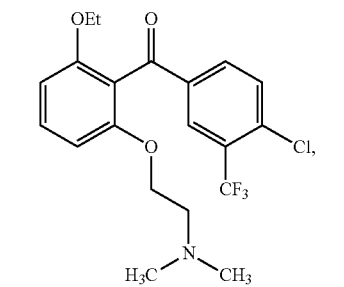

-continued
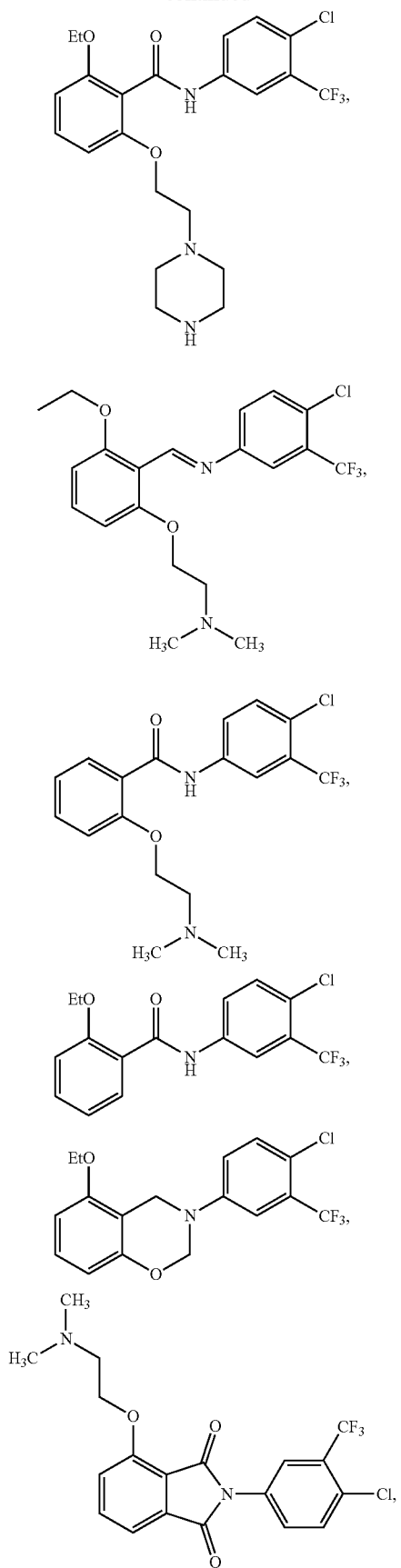
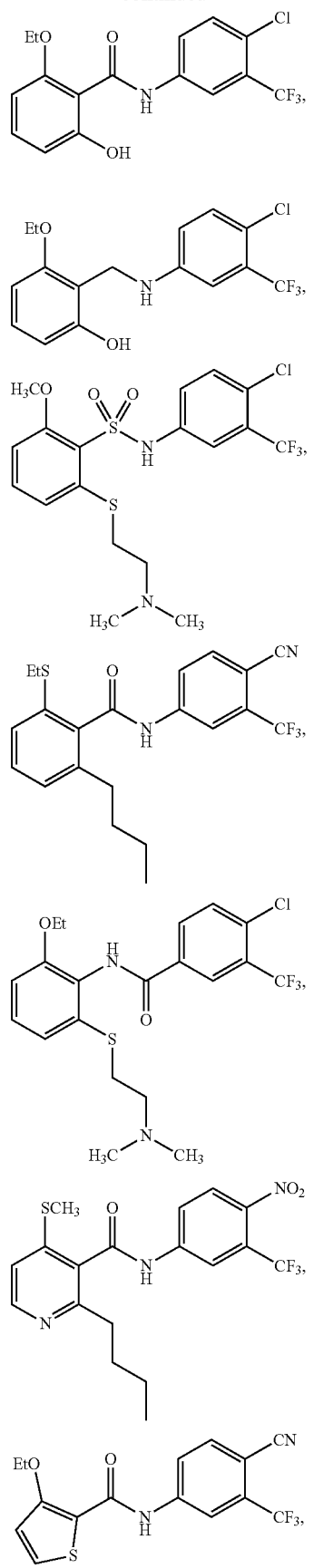

11
-continued
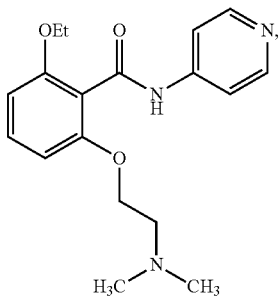
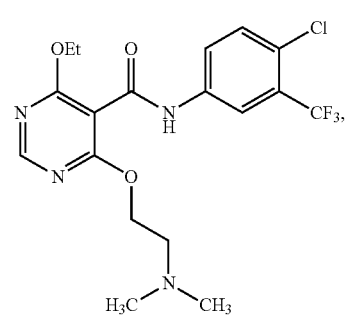
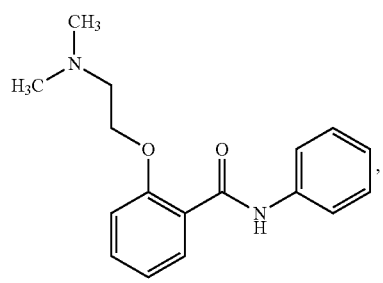
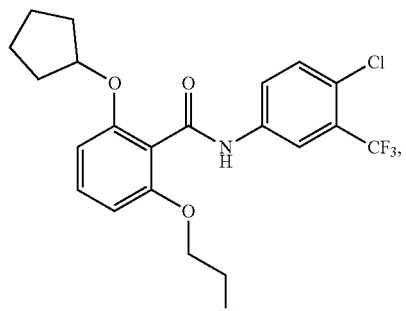
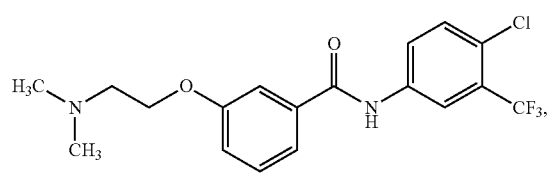
12
-continued
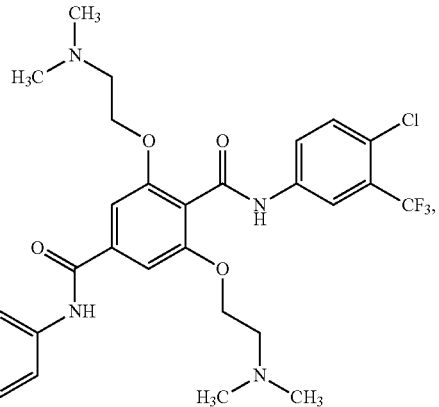
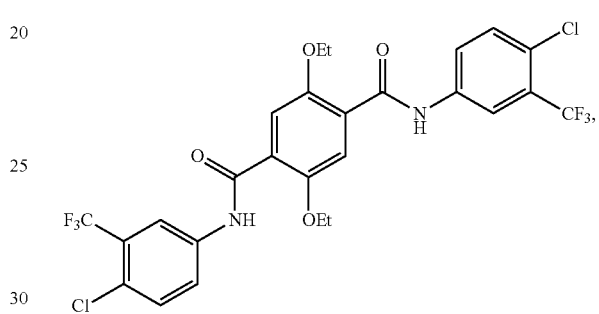
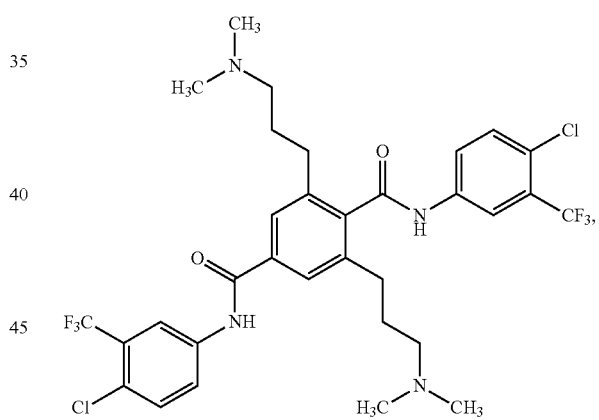
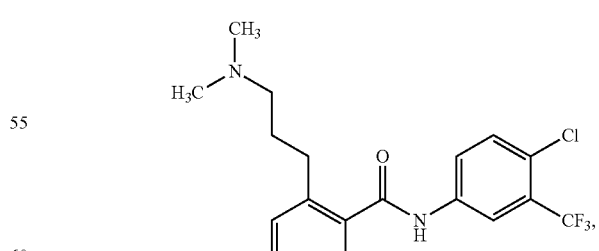
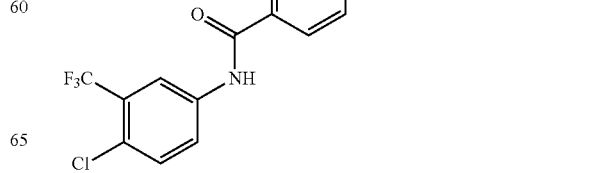

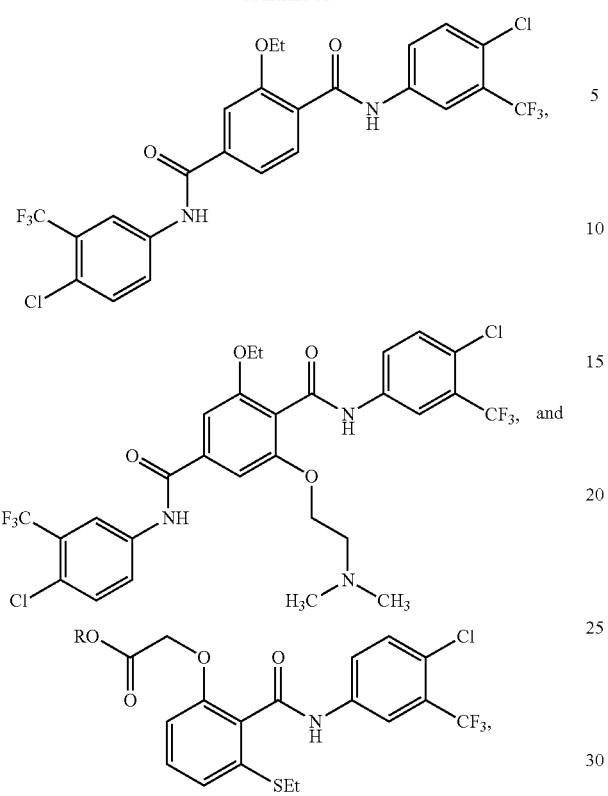
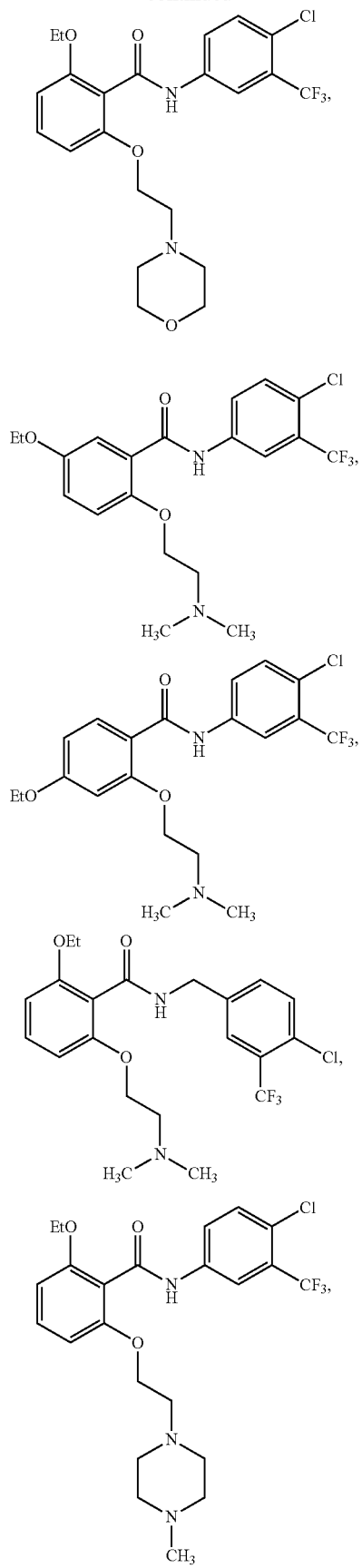
wherein R is H, Methyl, Ethyl, n-Propyl, Isopropyl, n-butyl, t-butyl, $C_8H_{18}$, $C_{15}H_{26}$, $C_{15}H_{28}$, $C_{15}H_{30}$, or $C_{15}H_{32}$.
In one embodiment of the pharmaceutical compositions disclosed herein, the HAT activator is selected from the group consisting of:

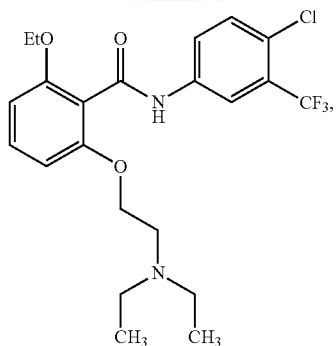
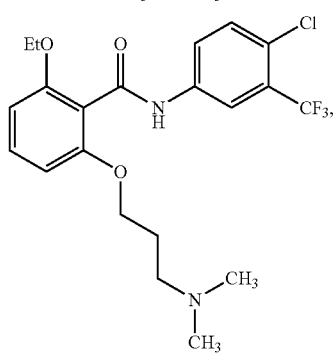
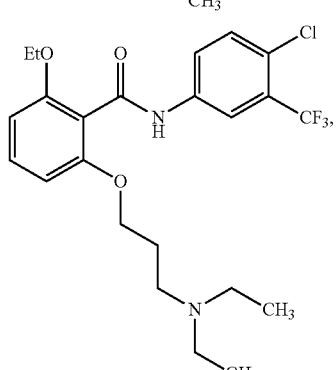
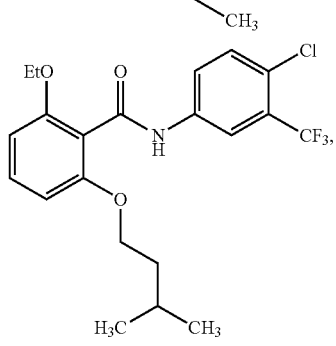
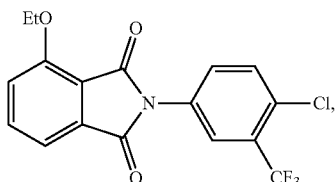
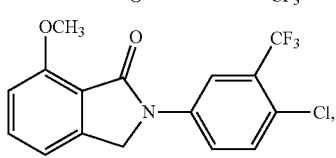
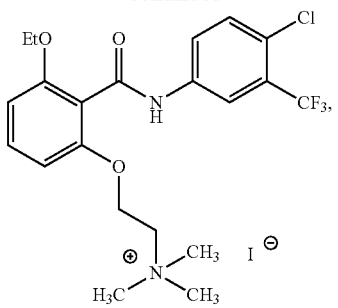
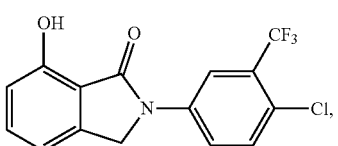
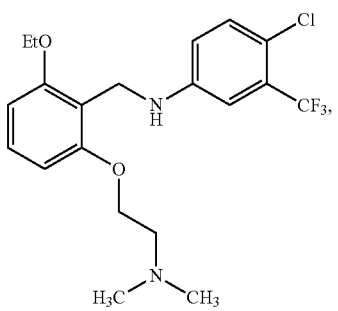
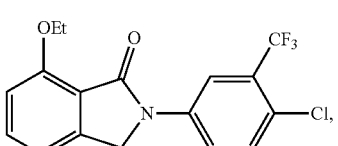
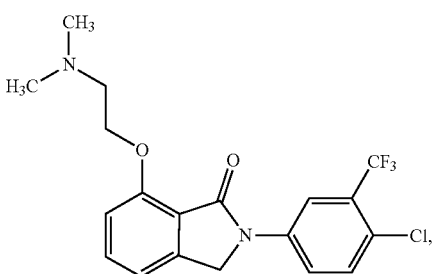
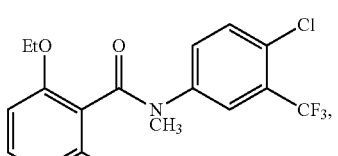
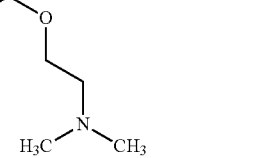

-continued
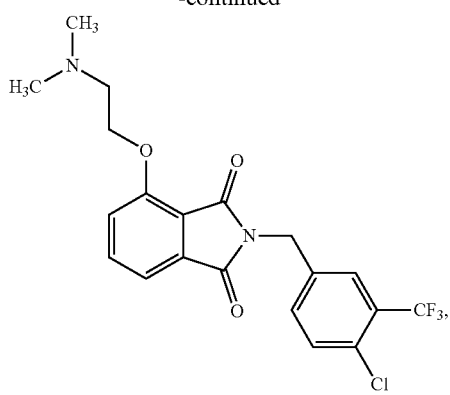
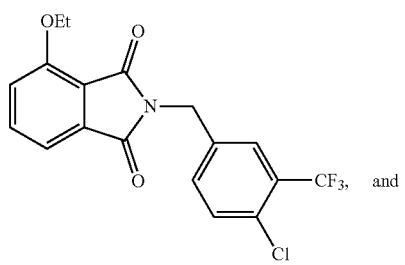 and
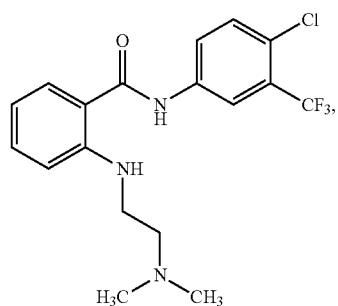
or a pharmaceutically acceptable salt thereof.
In one embodiment of the pharmaceutical compositions disclosed herein, the HAT activator is selected from the group consisting of
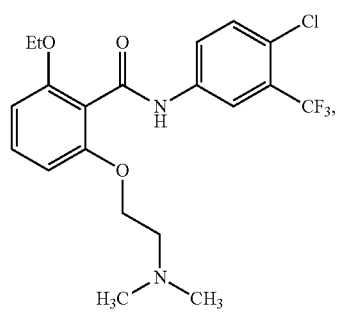 [SMILES: CCOc1cccc(OCCN(C)C)c1C(=O)Nc1ccc(Cl)c(C(F)(F)F)c1]
-continued
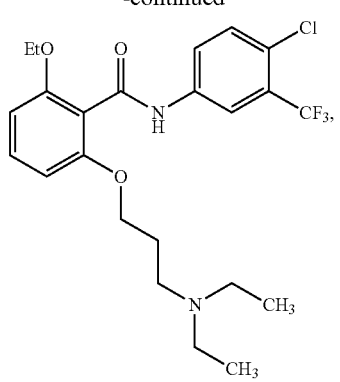
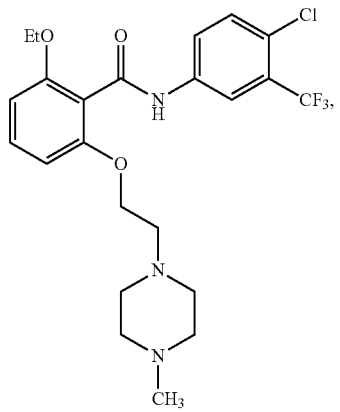
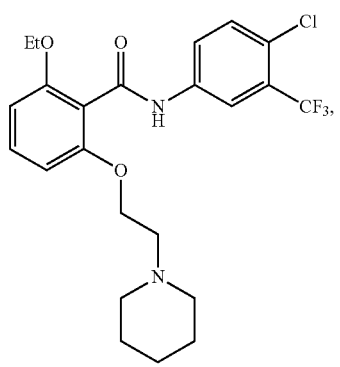
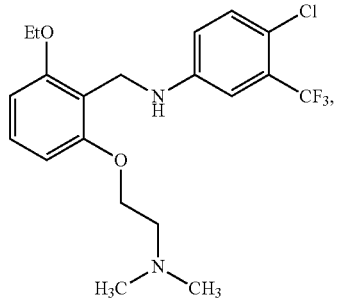

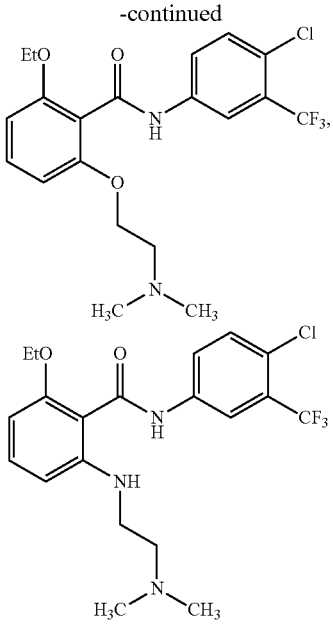

or a pharmaceutically acceptable salt thereof.

In one embodiment of the pharmaceutical compositions disclosed herein, the HAT activator is or a pharmaceutically acceptable salt thereof, and a HDAC inhibitor.

In one embodiment of the pharmaceutical compositions disclosed herein, the HAT activator is or a pharmaceutically acceptable salt thereof and a HDAC inhibitor. In a specific embodiment, the HAT activator is

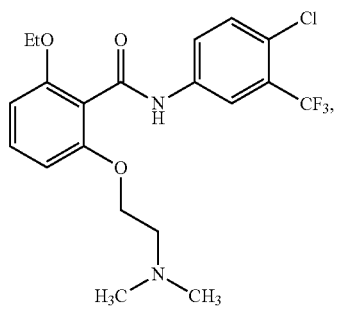 [SMILES: CCOc1cccc(OCCN(C)C)c1C(=O)Nc1ccc(Cl)c(C(F)(F)F)c1]

or a pharmaceutically acceptable salt thereof, and the HDAC inhibitor is romidepsin.

In one aspect, the invention is directed to methods for treating cancer in a subject in need thereof, the method comprising administering the pharmaceutical compositions above to a subject. In one embodiment of the any one of the methods disclosed herein, the cancer comprises B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkin's lymphoma, Hodgkin's lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, multiple myeloma, follicular lymphoma or medullary carcinoma.

In one embodiment of the any one of the methods disclosed herein, the HAT activator increases histone acetylation. In another embodiment of the any one of the methods disclosed herein, the HDAC inhibitor increases histone acetylation. In some embodiments, histone acetylation comprises acetylation of histones H2B, H3, H4, or a combination thereof. In other embodiments, histone acetylation comprises acetylation of histone lysine residues H3K4, H3K9, H3K14, H4K5, H4K8, H4K12, H4K16, or a combination thereof.

In one embodiment of the any one of the methods disclosed herein, the HAT activator increases p53 acetylation. In another embodiment of the any one of the methods disclosed herein, the HDAC inhibitor increases p53 acetylation.

In one embodiment of the any one of the methods disclosed herein, the IDAC inhibitor is romidepsin, vorinostat, belinostat, panobinostat, entinostat, mocetinostat, abexinostat, quisinostat or gavinostat. In some embodiments, the HDAC inhibitor is romidepsin or vorinostat. In another embodiment, the HDAC inhibitor is romidepsin.

In one embodiment of the any one of the methods disclosed herein, the cancer is colon cancer, lung cancer, renal cancer, leukemia, CNS cancer, melanoma, ovarian cancer, breast cancer, or prostate cancer. In other embodiments, the cancer is colon cancer, renal cancer, T cell leukemia, myeloma, leukemia, acute myeloid leukemia, acute lymphocytic leukemia, renal cell carcinoma, adenocarcinoma, glioblastoma, breast carcinoma, prostate carcinoma, or lung carcinoma. In one embodiment, the cancer is Hodgkin's lymphoma, non-Hodgkin's lymphoma, B cell lymphoma, T cell lymphoma, or follicular lymphoma. In some embodiments, the B cell lymphoma is diffuse large B-cell lymphoma.

In one embodiment of the any one of the methods disclosed herein, the cancer is diffuse large B-cell lymphoma selected from germinal center-derived diffuse large B cell lymphoma, an activated B-cell-derived (ABC) diffuse large B-cell lymphoma, or non-germinal center diffuse large B cell lymphoma.

Another aspect of the invention provides a method for reducing amyloid beta (A) protein deposits in a subject in need thereof, the method comprising administering to the subject a HAT activator and a HDAC inhibitor.

In one embodiment of the anyone of the methods disclosed herein, the subject exhibits abnormally elevated levels of amyloid beta plaques. In another embodiment, the subject is afflicted with Alzheimer's disease, Lewy body dementia, inclusion body myositis, or cerebral amyloid angiopathy. Another aspect of the invention provides a method for treating a neurodegenerative disease in a subject, the method comprising administering to a subject a HAT activator and a HDAC inhibitor.

In one embodiment of the any one of the methods disclosed herein, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease, Batten disease, Spinocerebellar ataxia, Spinal muscular atrophy, Steele-Richardson-Olszewski disease, Tabes dorsalis, or Toxic encephalopathy. In another embodiment, the neurodegenerative disease is selected from Alzheimer's Disease, ALS, Parkinson's Disease, and Huntington's Disease. In some embodiments, the neurodegenerative disease is Alzheimer's Disease. In other embodiments, the neurodegenerative disease is Huntington's Disease.

Another aspect of the invention provides a method for increasing memory retention in a subject afflicted with a neurodegenerative disease, the method comprising administering to a subject a HAT activator and a HDAC inhibitor.

In one embodiment of the any one of the methods disclosed herein, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease, Batten disease, Spinocerebellar ataxia, Spinal muscular atrophy, Steele-Richardson-Olszewski disease, Tabes dorsalis, or Toxic encephalopathy. In another embodiment, the neurodegenerative disease is Alzheimer's Disease.

In one aspect, the invention is directed to a method for treating cancer in a subject in need thereof, the method comprising administering to a subject

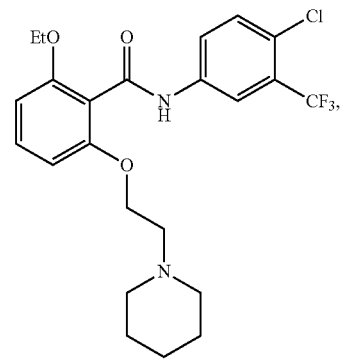 [SMILES: CCOc1cccc(OCCN2CCCCC2)c1C(=O)Nc1ccc(Cl)c(C(F)(F)F)c1]

or a pharmaceutically acceptable salt thereof, and a HDAC inhibitor.

Another aspect of the invention provides a method for treating cancer in a subject in need thereof, the method comprising administering to a subject

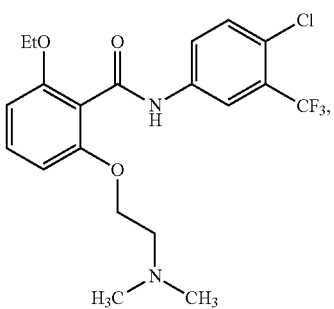

or a pharmaceutically acceptable salt thereof, and a HDAC inhibitor.

BRIEF DESCRIPTION OF THE FIGURES

FIGS. 9A-C show synergy between romidepsin and RP52 evaluated by luminetric assays in cell line Ly10. Cytotoxicity was measured at 24 (A), 48 (B) and 72 (C) hours. Synergy coefficient (RRR) was calculated for the Romidepsin in combination with RP52 treatment and is shown above the bars labeled R+1, R+2, R+4, R+6, R+8, or R+10. An RRR>1 represents an antagonistic interaction, RRR=1 additive, and RRR<1 synergistic interaction.

FIGS. 19A-B show acetylation of p53 and modulation of p21 by HAT activator RP52 in diffuse large B-cell lymphoma cell lines Ly1 (A) and Su-DHL6 (B).

FIGS. 20A-D show the concentration-effect relationship for 21 HAT activator compounds in a panel of non-Hodgkin's lymphoma cell lines at 48 hours. FIG. 20A shows percentage viability of cells treated with HAT activators YF2, JF1, JF3, JF4, JF5, JF7, JF8, JF9, JF10, JF16, JF18 as single agents or in combination with romidepsin at 48 hours. FIG. 20B shows the percentage viability of cells treated with HAT activators RP14, RP17, RP23, RP52, RP58, RP59, RP72, RP78, RP79, RP102 as single agents or in combination with romidepsin at 48 hours. FIG. 20C shows the synergy coefficients calculated as the relative risk ratio (RRR) for cells treated with HAT activators YF2, JF1, JF3, JF4, JF5, JF7, JF8, JF9, JF10, JF16, JF18 as single agents or in combination with romidepsin at 48 hours. FIG. 20D shows the synergy coefficients calculated as the relative risk ratio (RRR) for cells treated with HAT activators RP14, RP17, RP23, RP52, RP58, RP59, RP72, RP78, RP79, RP102 as single agents or in combination with romidepsin at 48 hours.

FIGS. 22A-E show the synergy effect of JF1 with romidepsin in B-cell lymphoma cell lines. Pfeiffer cells (FIG. 22A) and SUDHL-10 cells (FIG. 22B) were exposed to increasing concentration of JF1 and romidepsin alone and in combinations at 72 hrs. Five B-cell lymphoma cell lines were exposed to increasing concentration of JF1 and romidepsin alone and in combinations at 48 hrs (FIG. 22C) and 72 hrs (FIG. 22D) and the Excess Over Bliss was measured for each. Synergy is defined by an Excess Over Bliss of 10. The synergy of JF1 and romidepsin in each cell line and at each time point is further indicated in FIG. 22E.

FIG. 27 shows the synergy of JF1/YF2 and romidepsin in each cell line at 72 hr with EOB, which provides further details for FIG. 23 and FIG. 24.

DETAILED DESCRIPTION OF THE INVENTION

Figure 1:
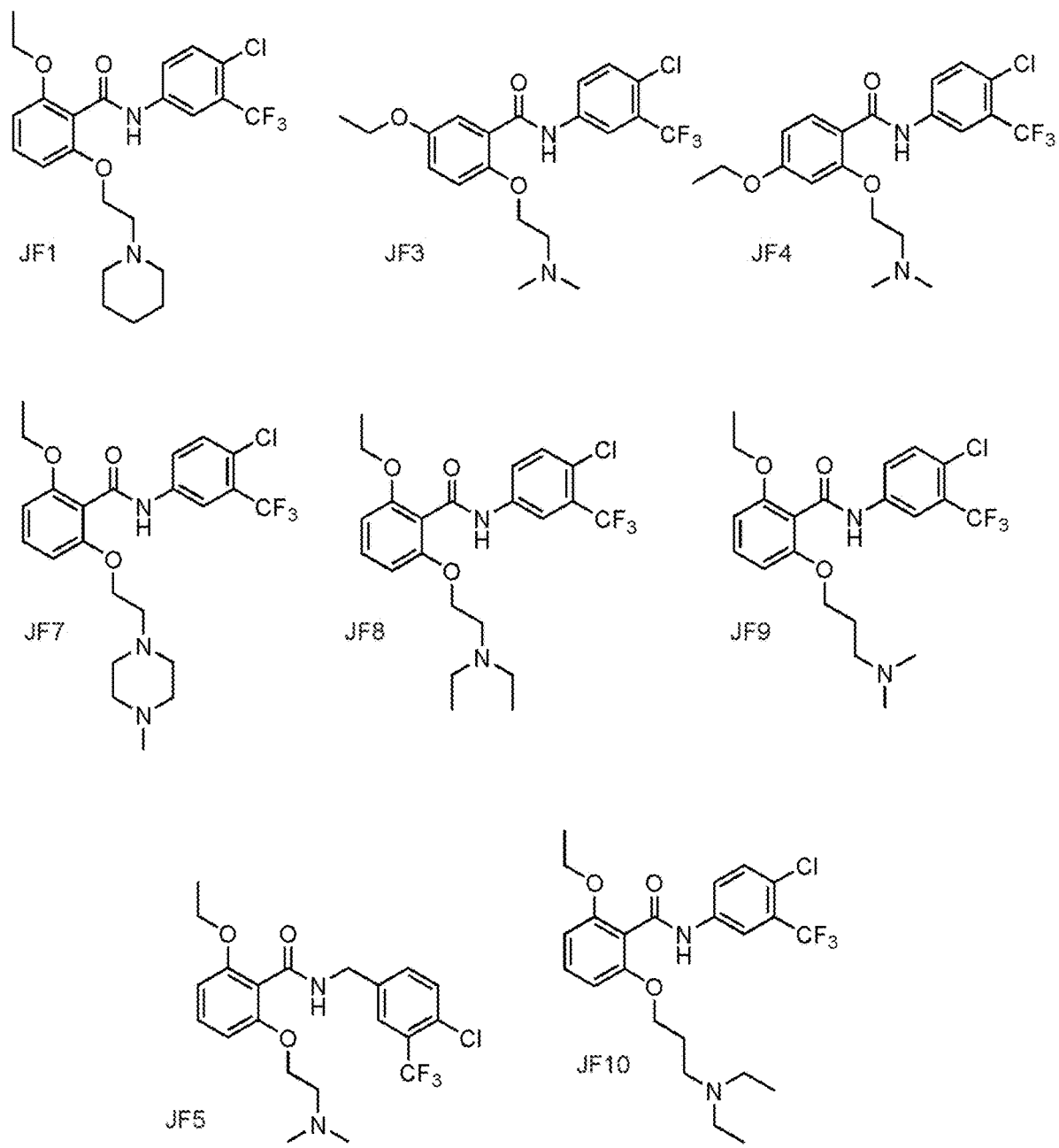
FIG. 1 shows chemical structures of representative HAT modulator compounds.
Figure 2:
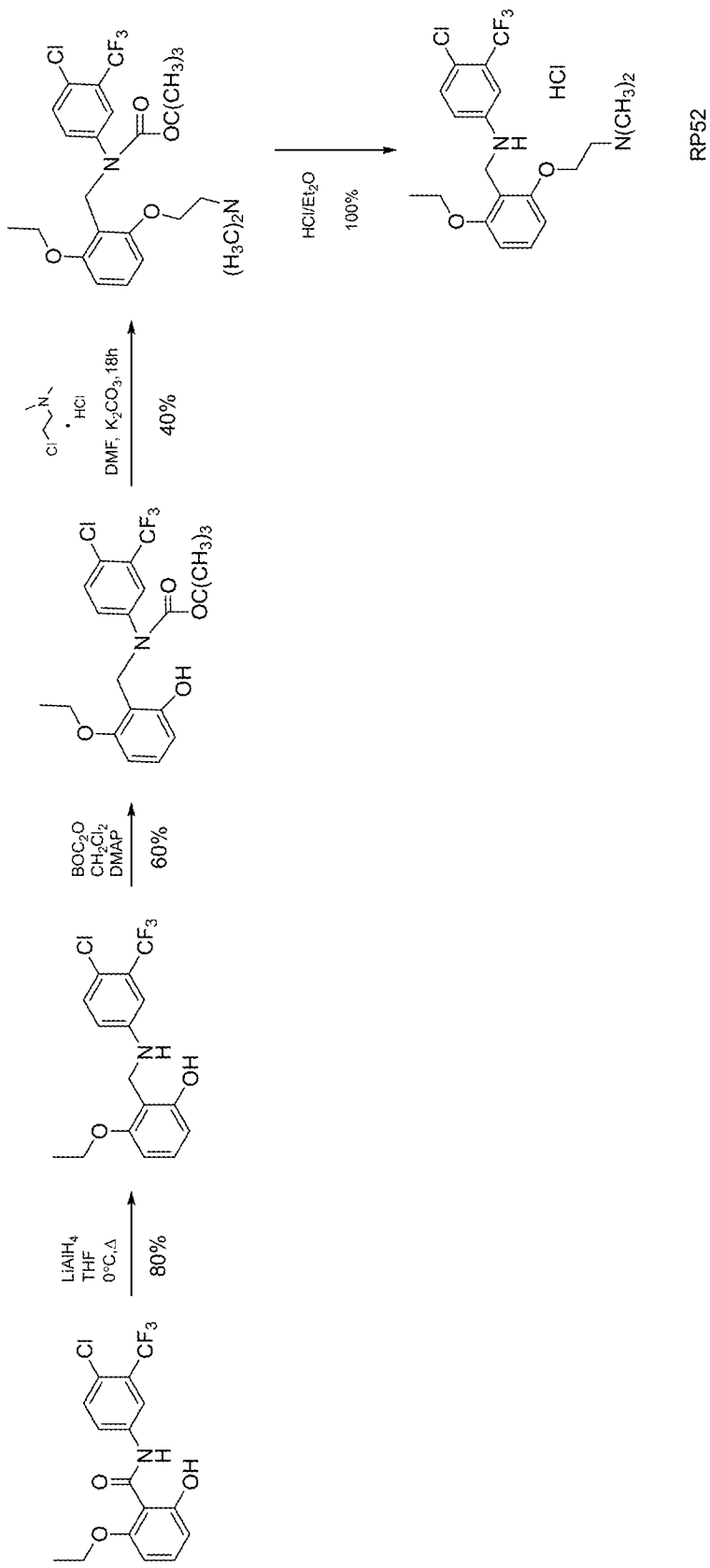
FIG. 2 shows scheme of synthesis of RP52.
Figure 3:
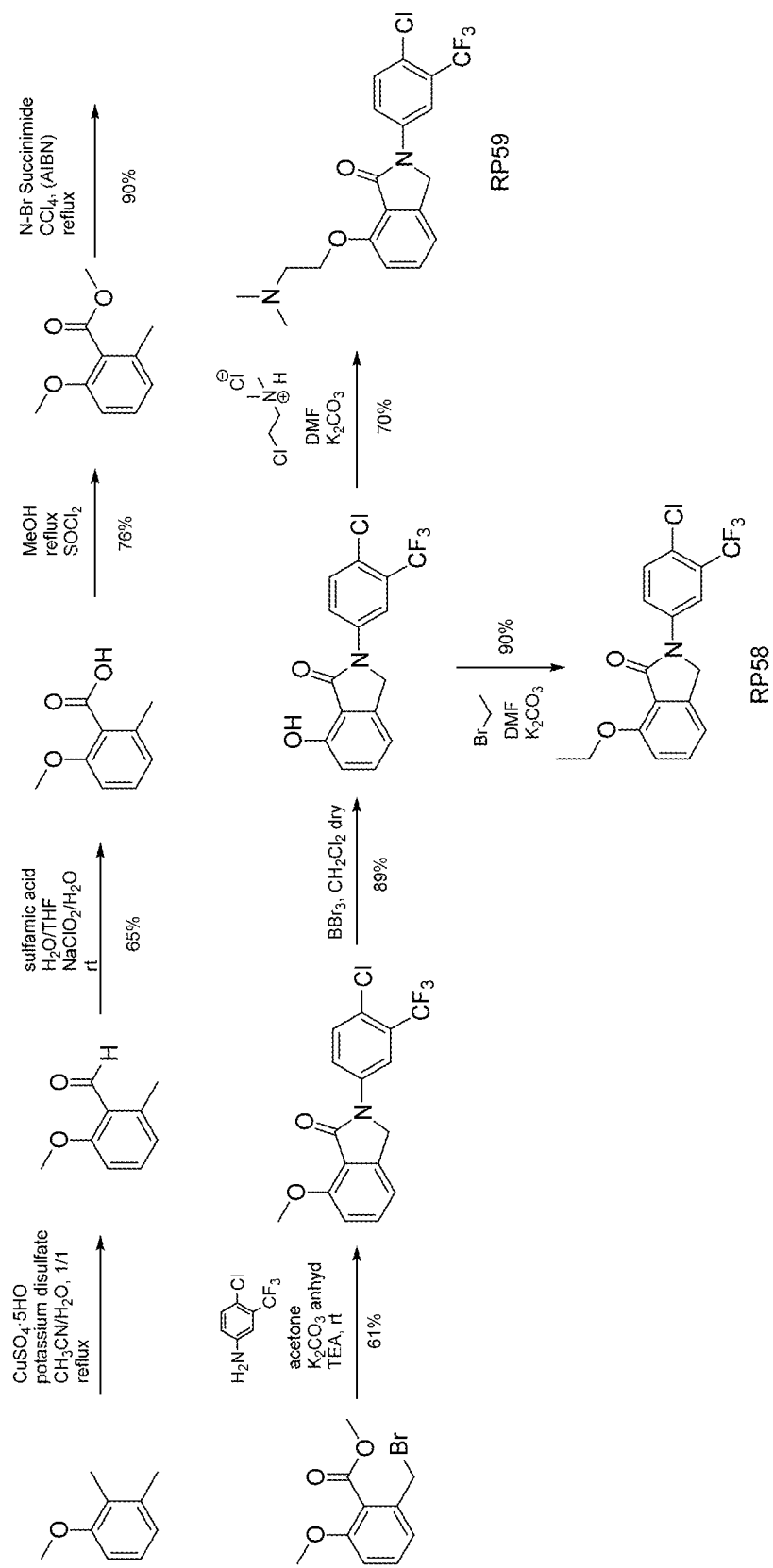
FIG. 3 shows scheme of synthesis of RP14, RP58, and RP59.
Figure 4:
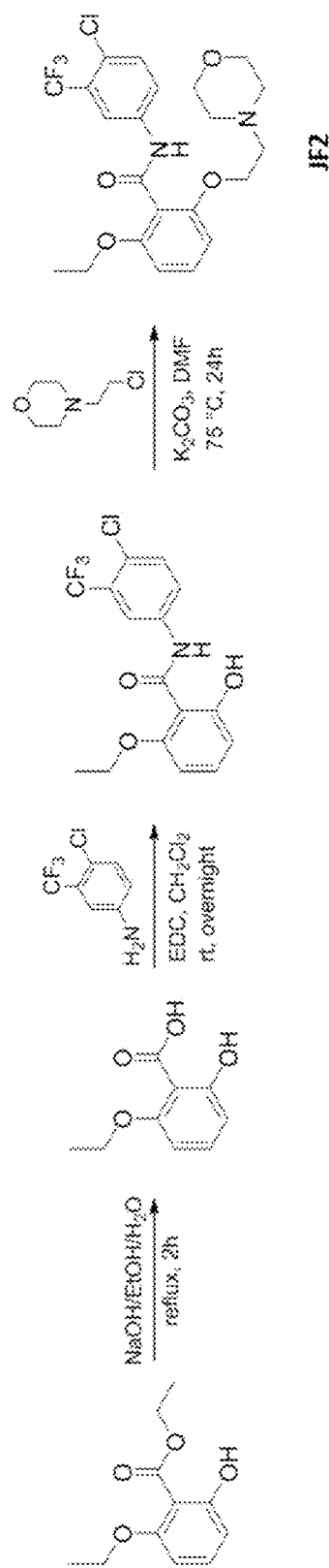
FIG. 4 shows scheme of synthesis of JF2.
Figure 5A:
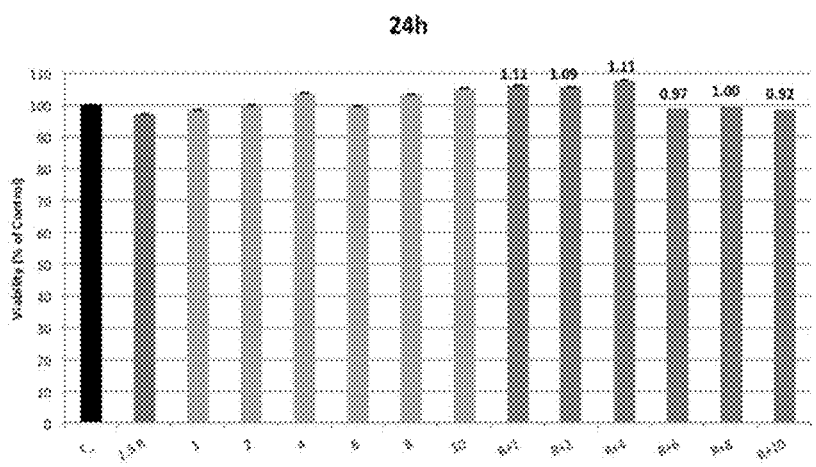
FIGS. 5A-C show synergy between romidepsin and RP14 evaluated by luminetric assays in cell line Ly7. Cytotoxicity was measured at 24 (A), 48 (B) and 72 (C) hours. Synergy coefficient (RRR) was calculated for the Romidepsin in combination with RP14 treatment and is shown above the bars labeled R+1, R+2, R+4, R+6, R+8, or R+10. An RRR<1 represents an antagonistic interaction, RRR=1 additive, and RRR>1 synergistic interaction.
Figure 5B:
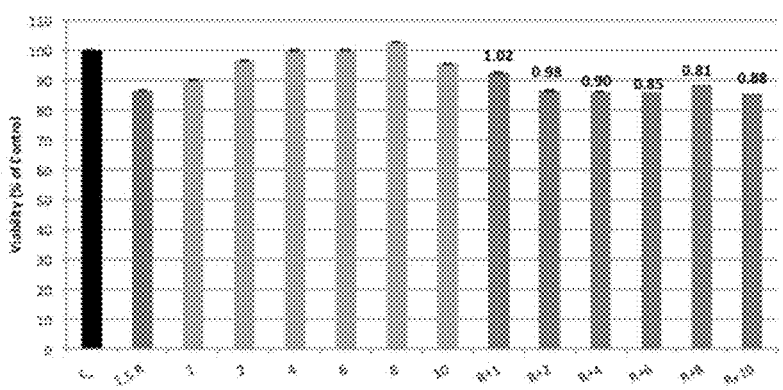
Figure 5C:
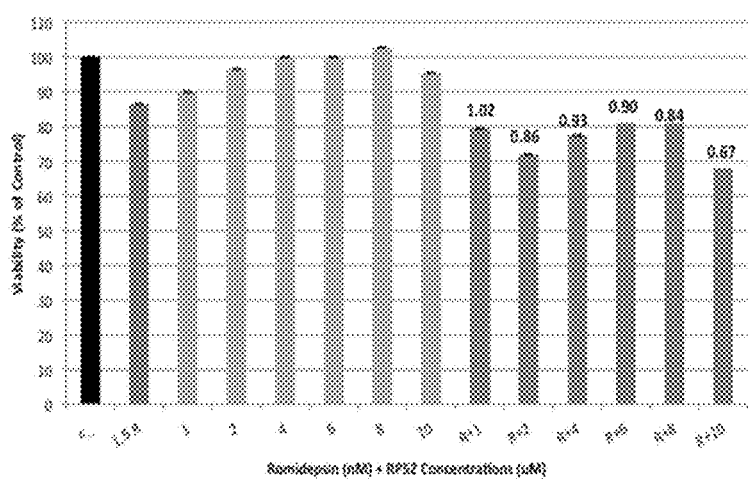
Figure 6A:
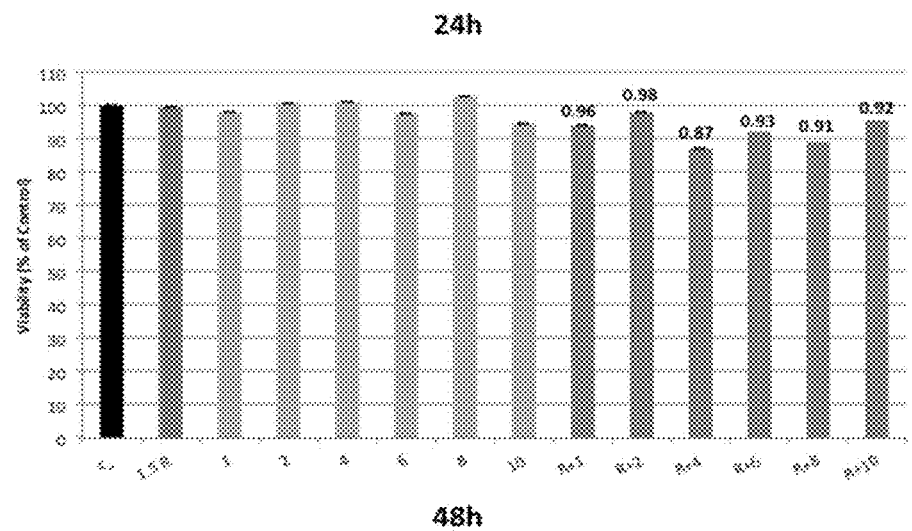
FIGS. 6A-C show synergy between romidepsin and RP14 evaluated by luminetric assays in cell line Ly10. Cytotoxicity was measured at 24 (A), 48 (B) and 72 (C) hours. Synergy coefficient (RRR) was calculated for the Romidepsin in combination with RP14 treatment and is shown above the bars labeled R+1, R+2, R+4, R+6, R+8, or R+10. An RRR>1 represents an antagonistic interaction, RRR=1 additive, and RRR<1 synergistic interaction.
Figure 6B:
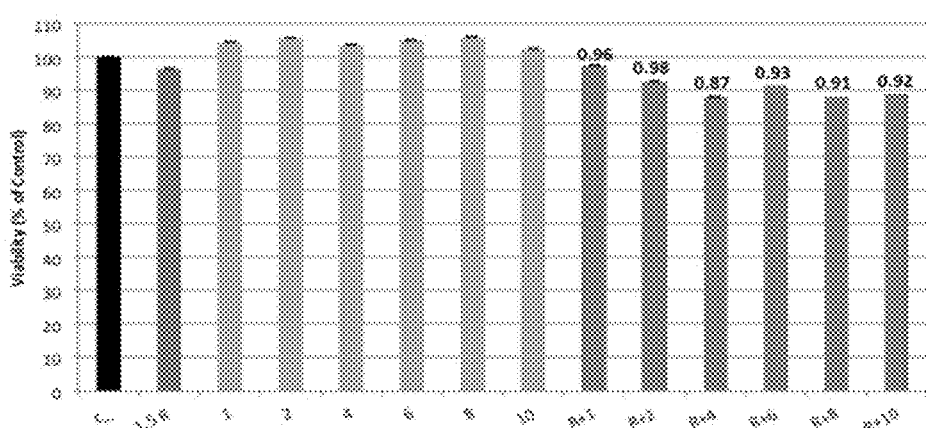
Figure 6C:
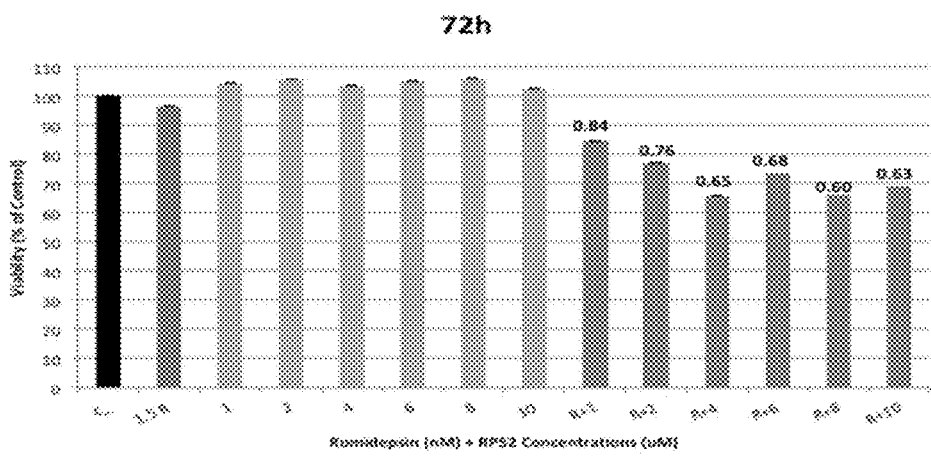
Figure 7A:
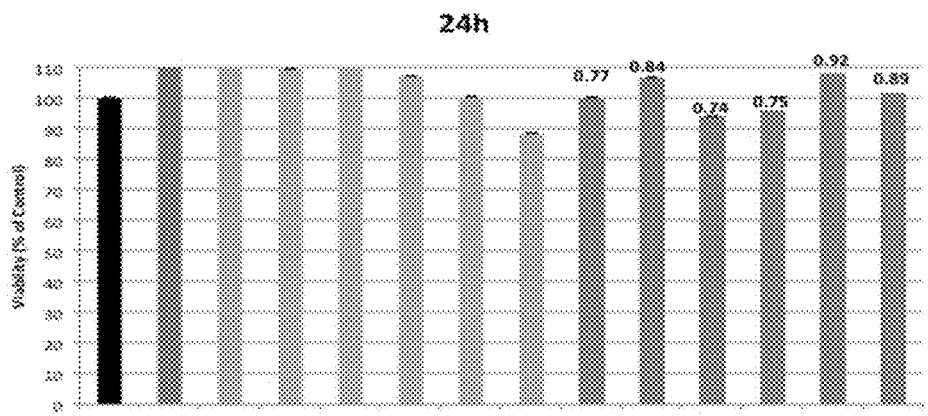
FIGS. 7A-C show synergy between romidepsin and RP14 evaluated by luminetric assays in cell line SuDHL-6. Cytotoxicity was measured at 24 (A), 48 (B) and 72 (C) hours. Synergy coefficient (RRR) was calculated for the Romidepsin in combination with RP14 treatment and is shown above the bars labeled R+1, R+2, R+4, R+6, R+8, or R+10. An RRR>1 represents an antagonistic interaction, RRR=1 additive, and RRR<1 synergistic interaction.
Figure 7B:
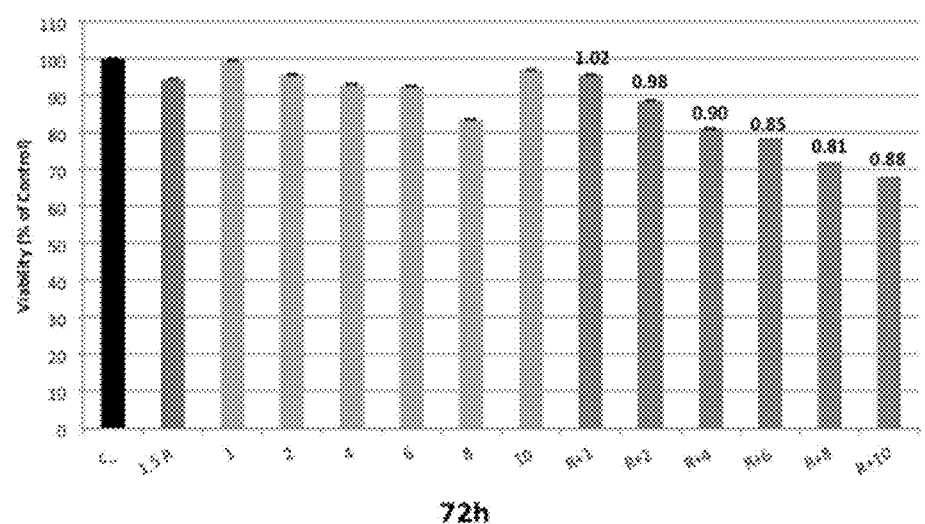
Figure 7C:
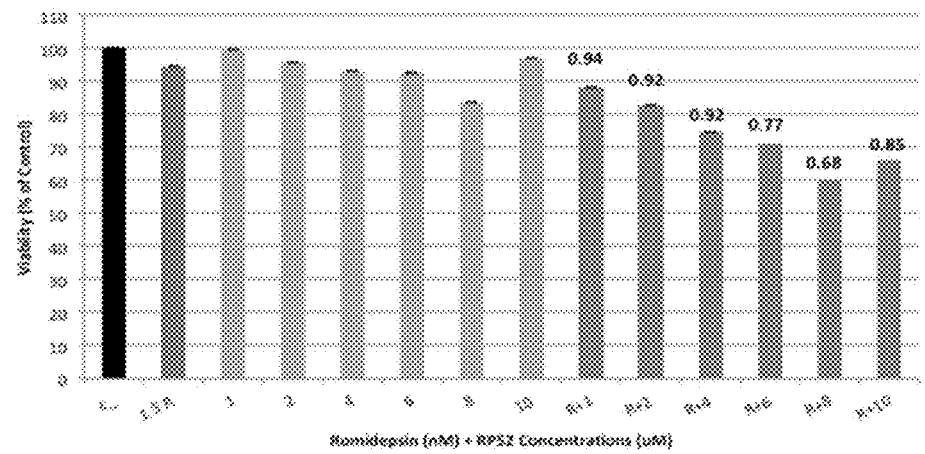
Figure 8A:
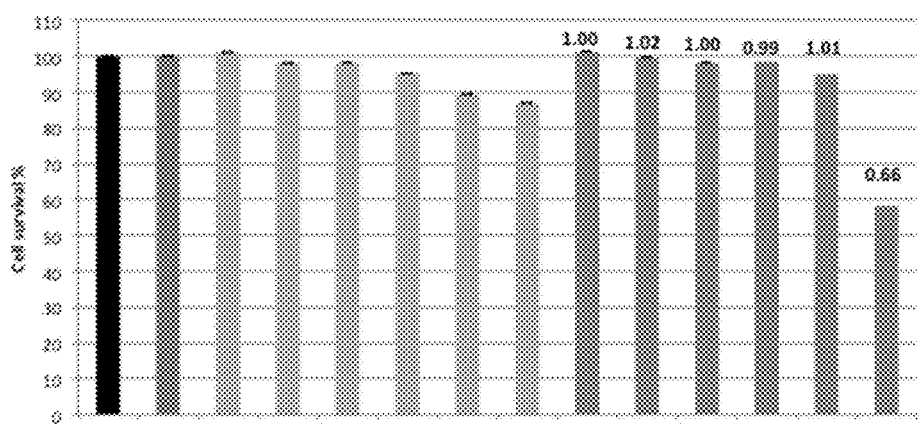
FIGS. 8A-C show synergy between romidepsin and RP52 evaluated by luminetric assays in cell line Ly7. Cytotoxicity was measured at 24 (A), 48 (B) and 72 (C) hours. Synergy coefficient (RRR) was calculated for the Romidepsin in combination with RP52 treatment and is shown above the bars labeled R+1, R+2, R+4, R+6, R+8, or R+10. An RRR>1 represents an antagonistic interaction, RRR=1 additive, and RRR<1 synergistic interaction.
Figure 8B:
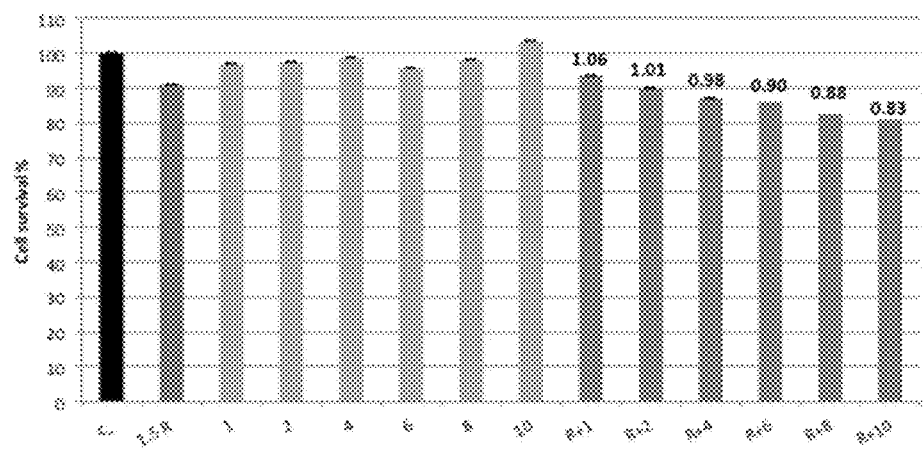
Figure 8C:
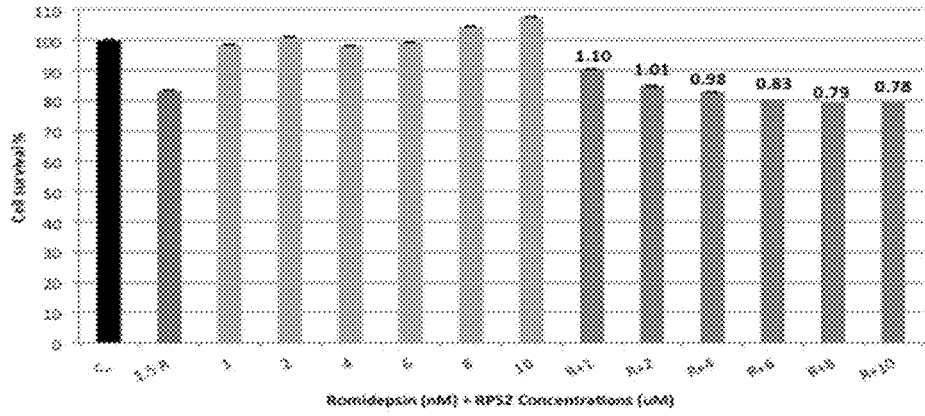
Figure 10A:
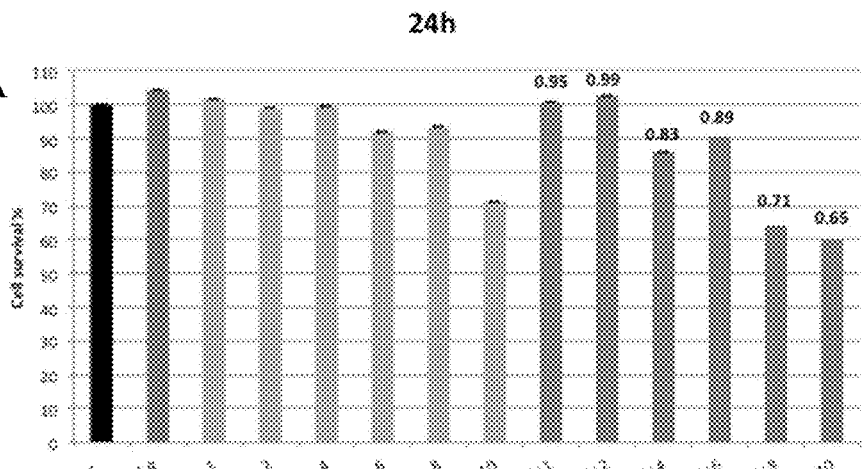
FIGS. 10A-C show synergy between romidepsin and RP52 evaluated by luminetric assays in cell line SuDHL-6. Cytotoxicity was measured at 24 (A), 48 (B) and 72 (C) hours. Synergy coefficient (RRR) was calculated for the Romidepsin in combination with RP52 treatment and is shown above the bars labeled R+1, R+2, R+4, R+6, R+8, or R+10. An RRR>1 represents an antagonistic interaction, RRR=1 additive, and RRR<1 synergistic interaction.
Figure 10B:
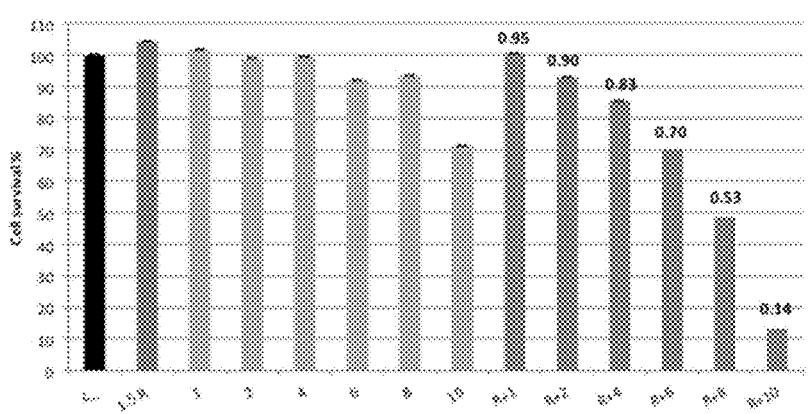
Figure 10C:
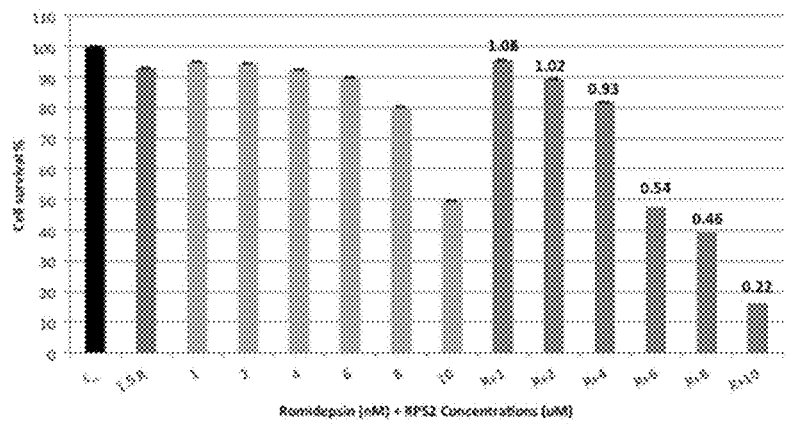
Figure 11A:
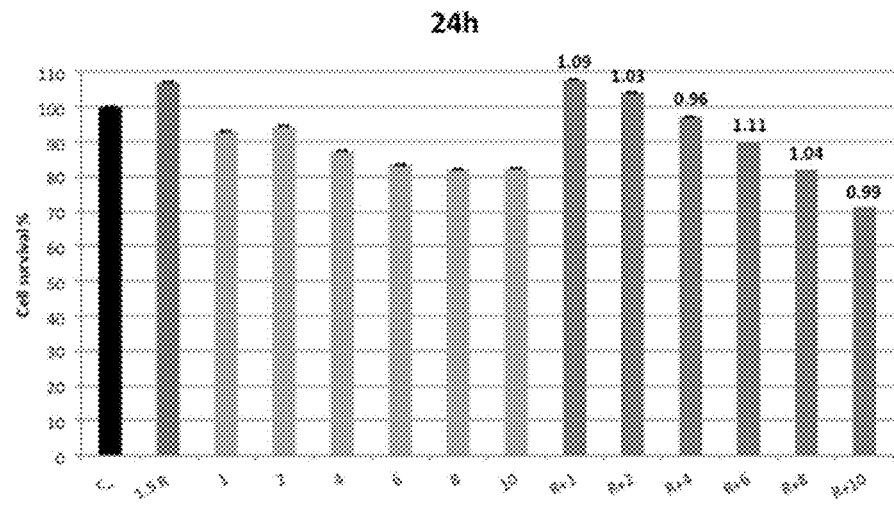
FIGS. 11A-C show synergy between romidepsin and RP59 evaluated by luminetric assays in cell line Ly7. Cytotoxicity was measured at 24 (A), 48 (B) and 72 (C) hours. Synergy coefficient (RRR) was calculated for the Romidepsin in combination with RP59 treatment and is shown above the bars labeled R+1, R+2, R+4, R+6, R+8, or R+10. An RRR>1 represents an antagonistic interaction, RRR=1 additive, and RRR<1 synergistic interaction.
Figure 11B:
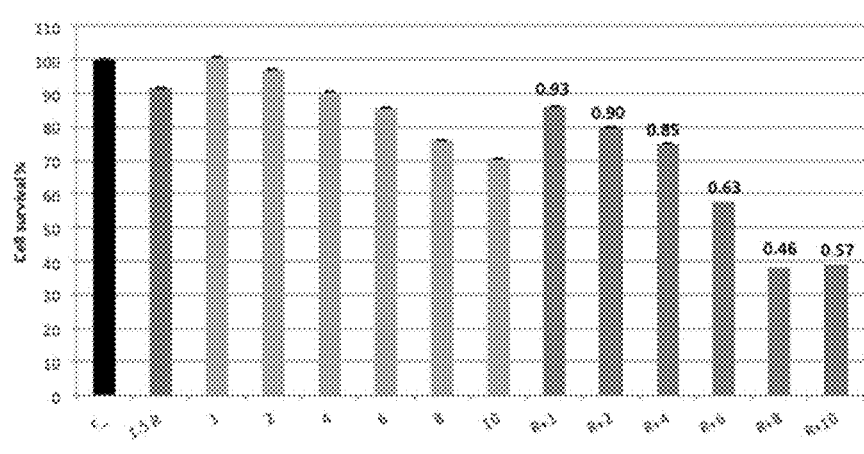
Figure 11C:
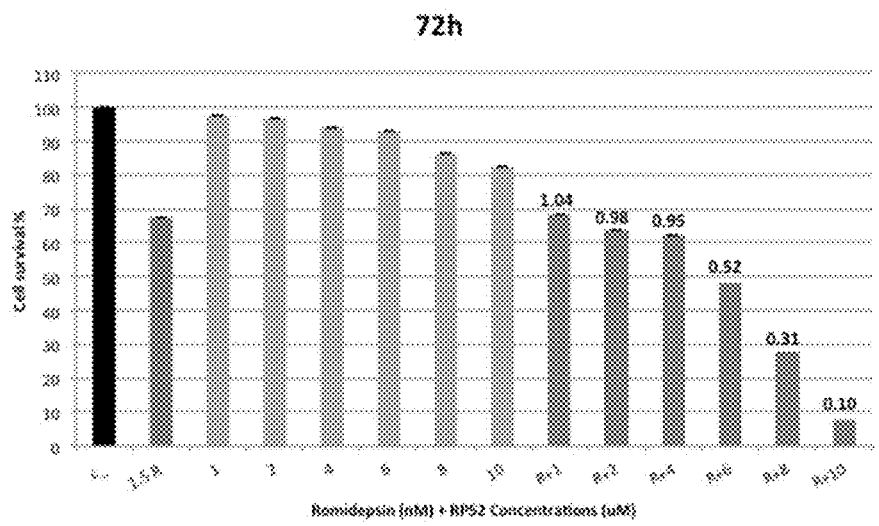
Figure 12A:
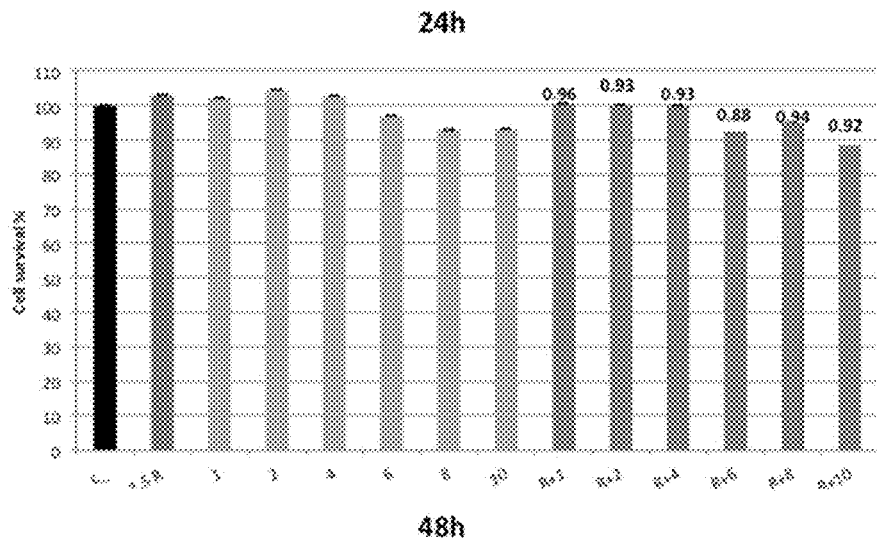
FIGS. 12A-C show synergy between romidepsin and RP59 evaluated by luminetric assays in cell line Ly10. Cytotoxicity was measured at 24 (A), 48 (B) and 72 (C) hours. Synergy coefficient (RRR) was calculated for the Romidepsin in combination with RP59 treatment and is shown above the bars labeled R+1, R+2, R+4, R+6, R+8, or R+10. An RRR>1 represents an antagonistic interaction, RRR=1 additive, and RRR<1 synergistic interaction.
Figure 12B:
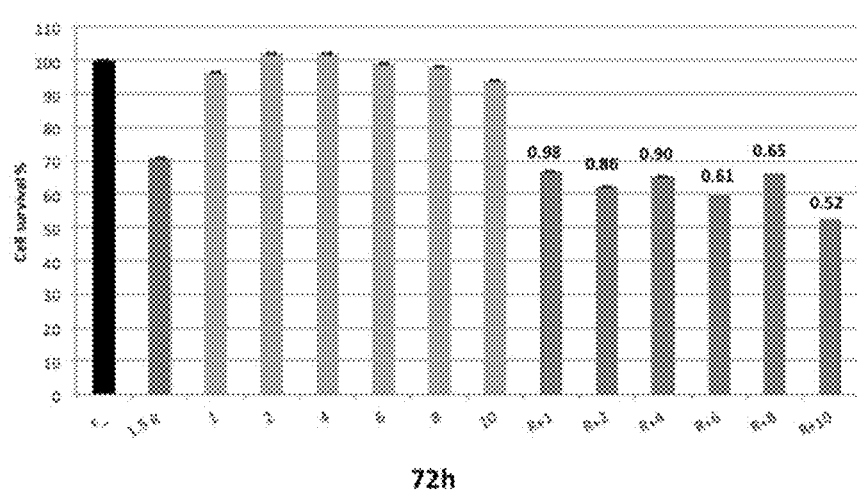
Figure 12C:
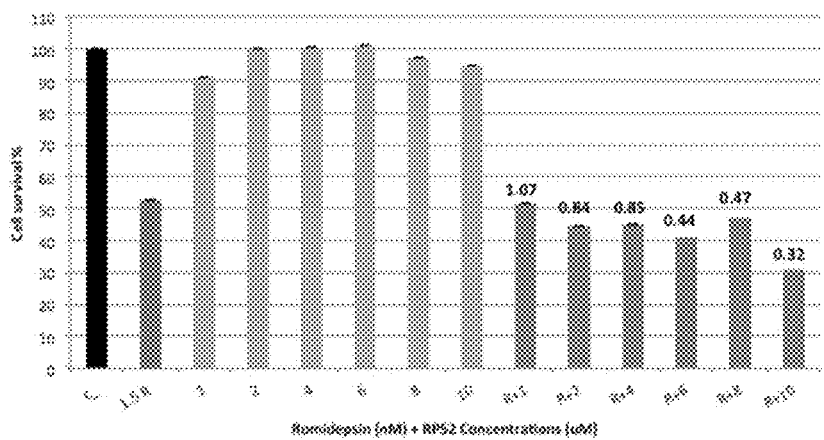
Figure 13A:
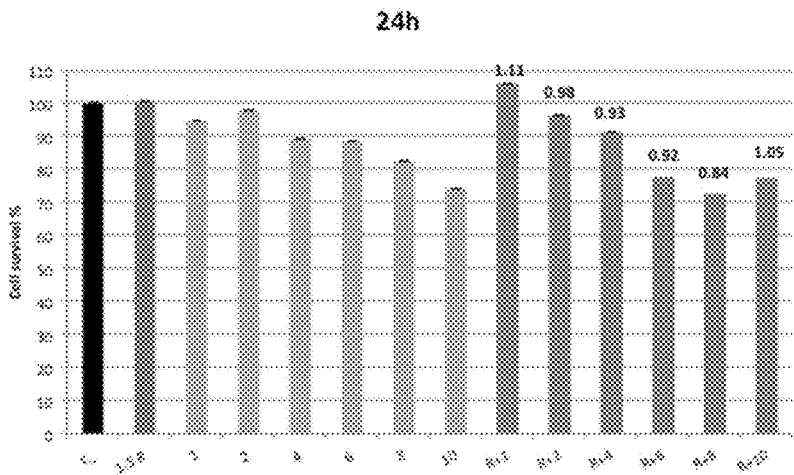
FIGS. 13A-C show synergy between romidepsin and RP59 evaluated by luminetric assays in cell line SuDHL-6. Cytotoxicity was measured at 24 (A), 48 (B) and 72 (C) hours. Synergy coefficient (RRR) was calculated for the Romidepsin in combination with RP59 treatment and is shown above the bars labeled R+1, R+2, R+4, R+6, R+8, or R+10. An RRR>1 represents an antagonistic interaction, RRR=1 additive, and RRR<1 synergistic interaction.
Figure 13B:
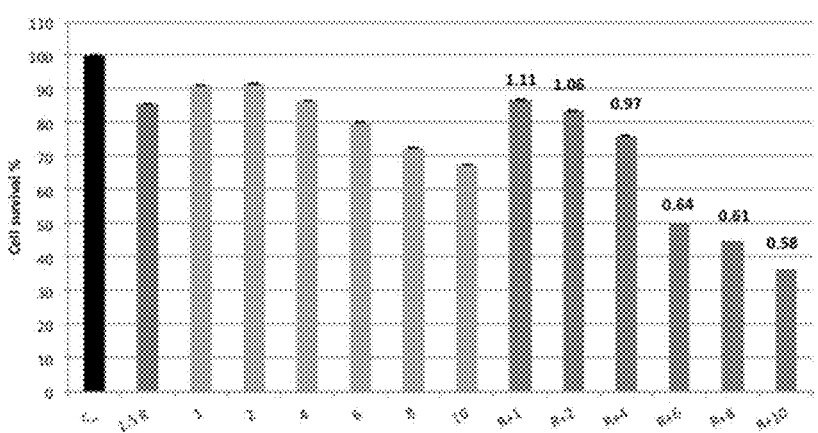
Figure 13C:
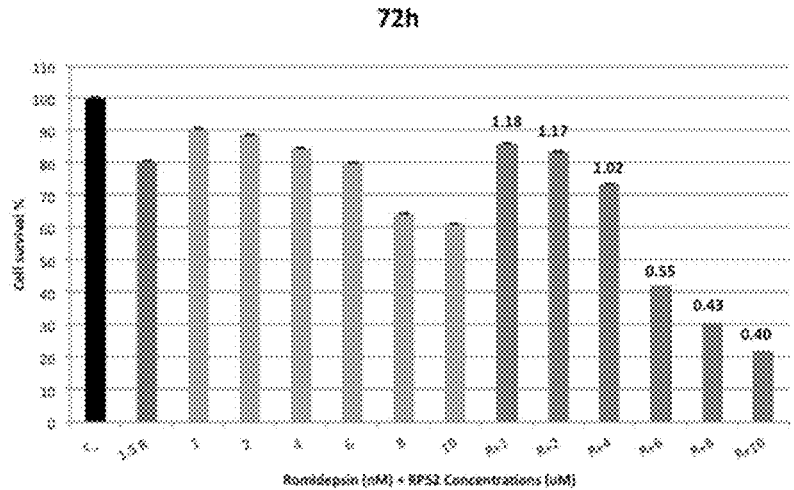
Figure 14A:
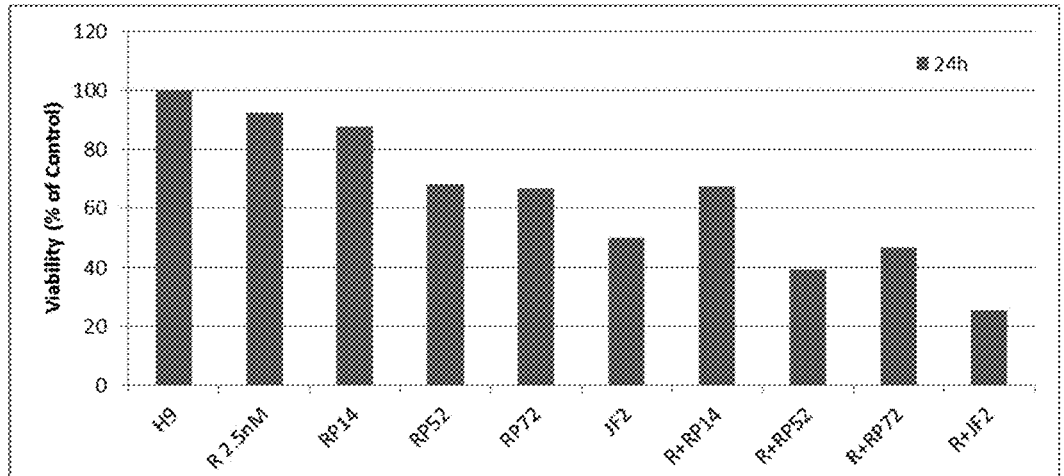
FIGS. 14A-C show synergy between romidepsin and different HAT activators (RP14, RP52, RP72, JF2) evaluated by luminetric assays in cell line H9. Cytotoxicity was measured at 24 (A), 48 (B) and 72 (C) hours.
Figure 14B:
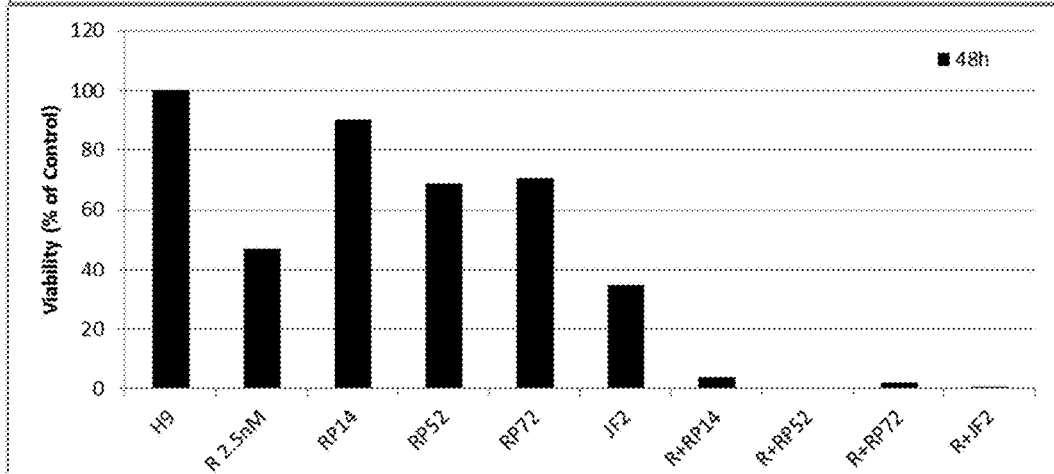
Figure 14C:
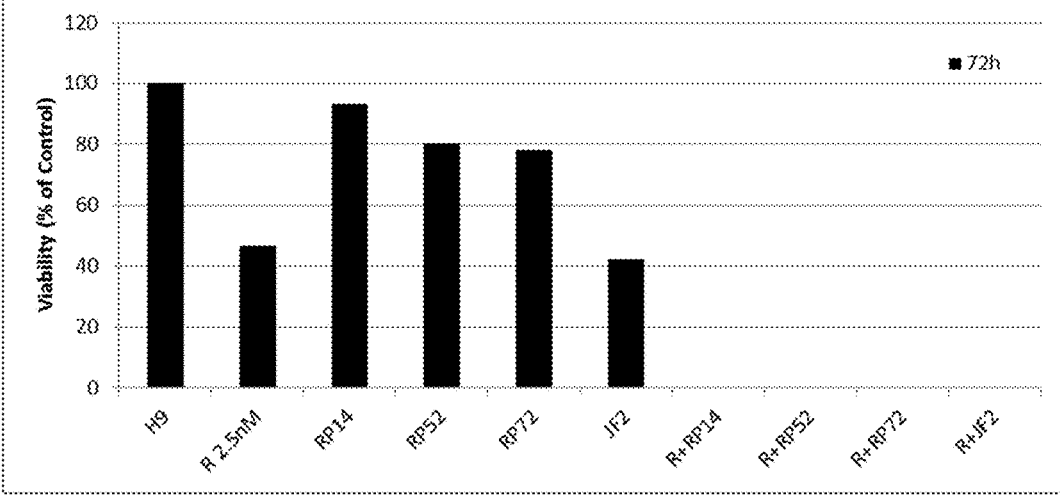
Figure 15A:
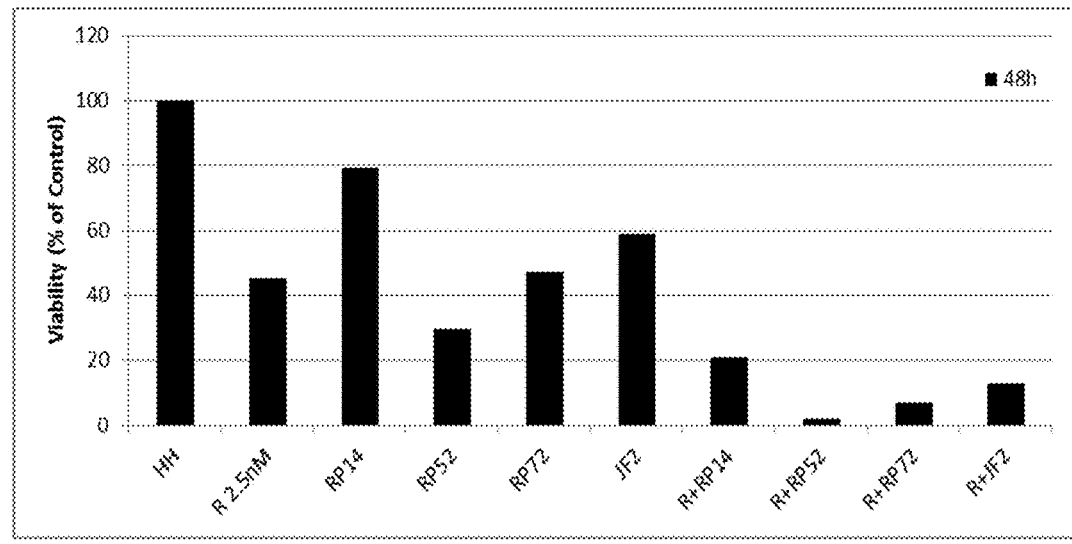
FIGS. 15A-B show synergy between romidepsin and different HAT activators (RP14, RP52, RP72, JF2) evaluated by luminetric assays in cell line HH. Cytotoxicity was measured at 48 (A), and 72 (C) hours.
Figure 15B:
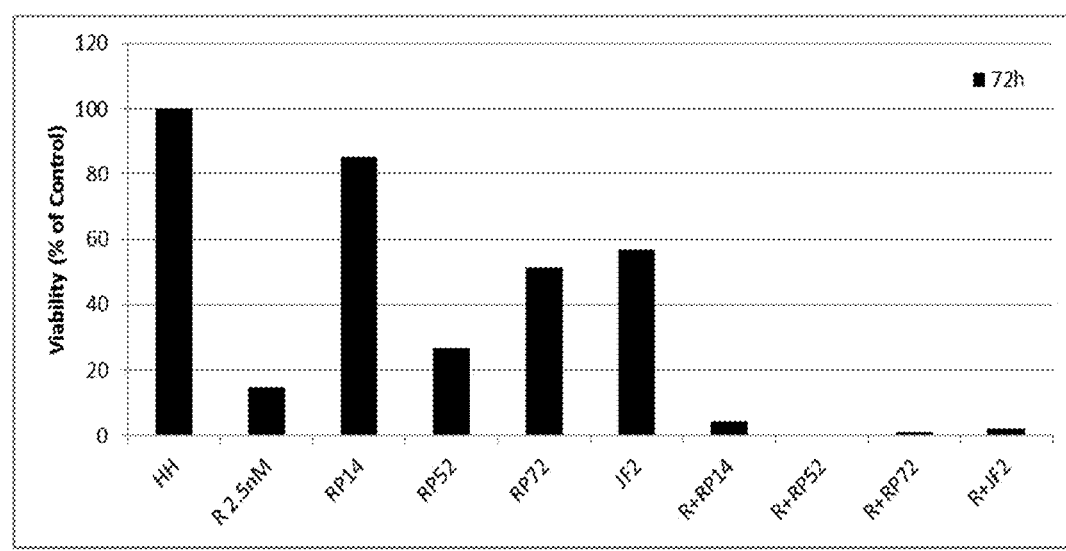
Figure 16A:
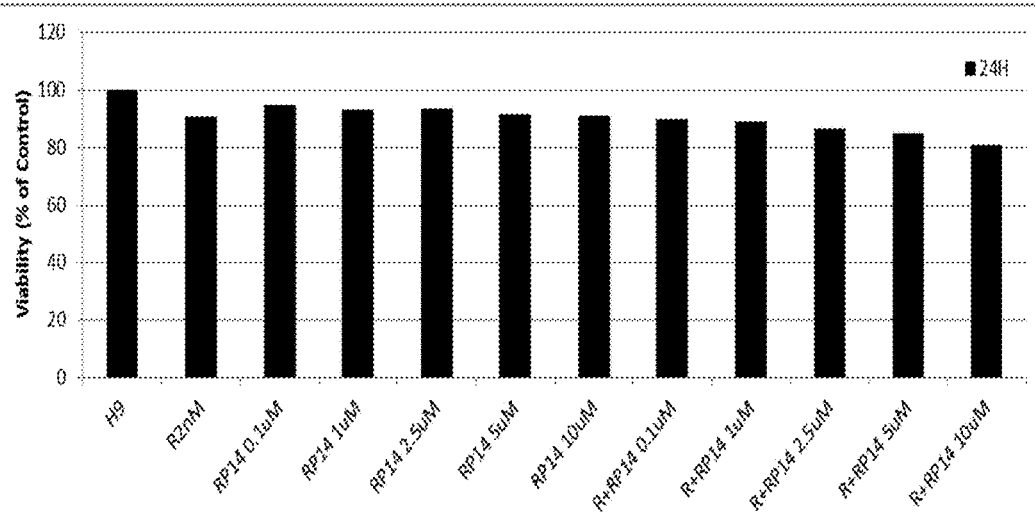
FIGS. 16A-C show synergy between romidepsin and RP14 evaluated by luminetric assays in cell line H9. Cytotoxicity was measured at 24 (A), 48 (B) and 72 (C) hours.
Figure 16B:
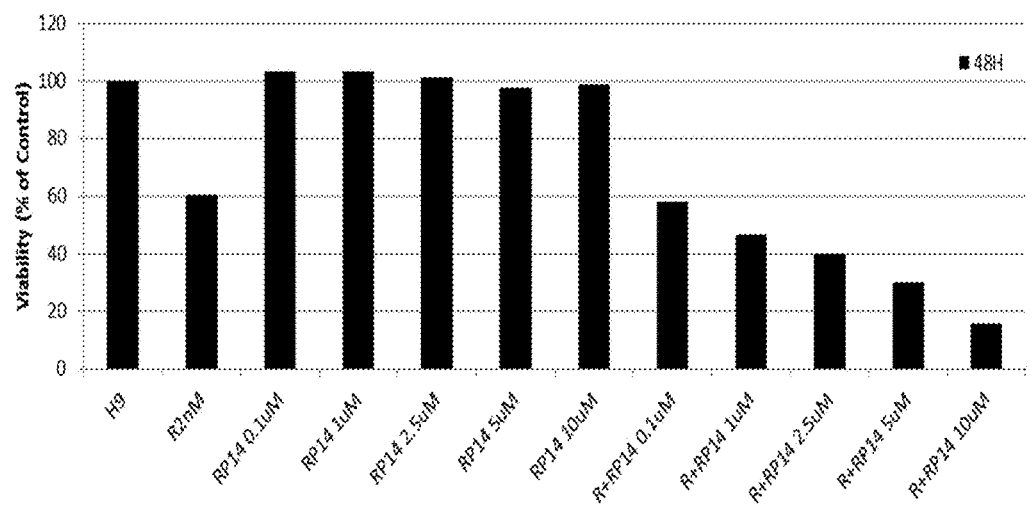
Figure 16C:
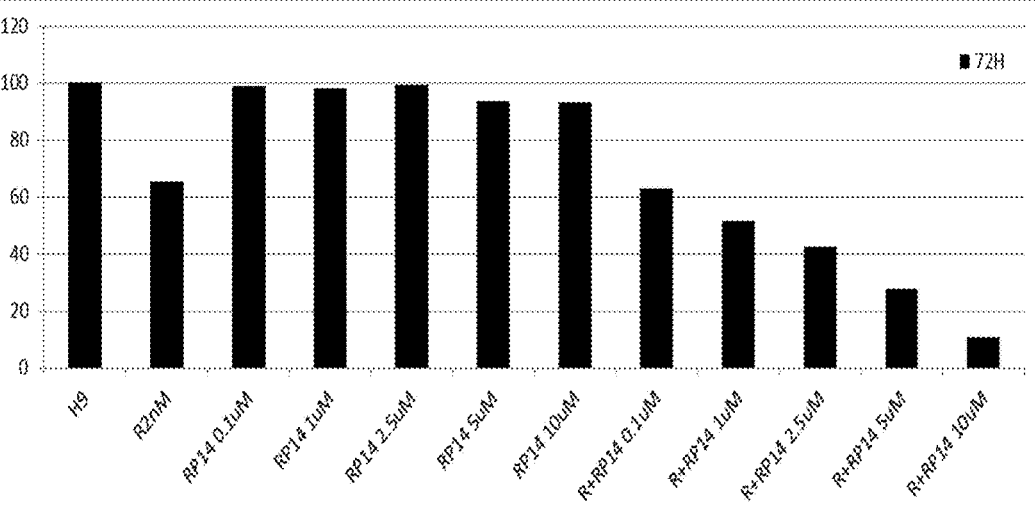
Figure 17A:
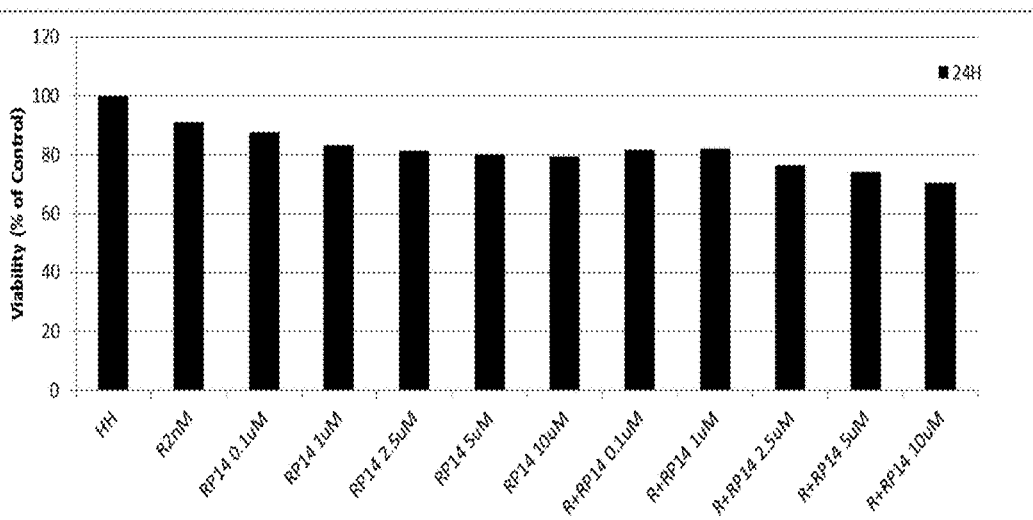
FIGS. 17A-C show synergy between romidepsin and RP14 evaluated by luminetric assays in cell line HH. Cytotoxicity was measured at 24 (A), 48 (B) and 72 (C) hours.
Figure 17B:
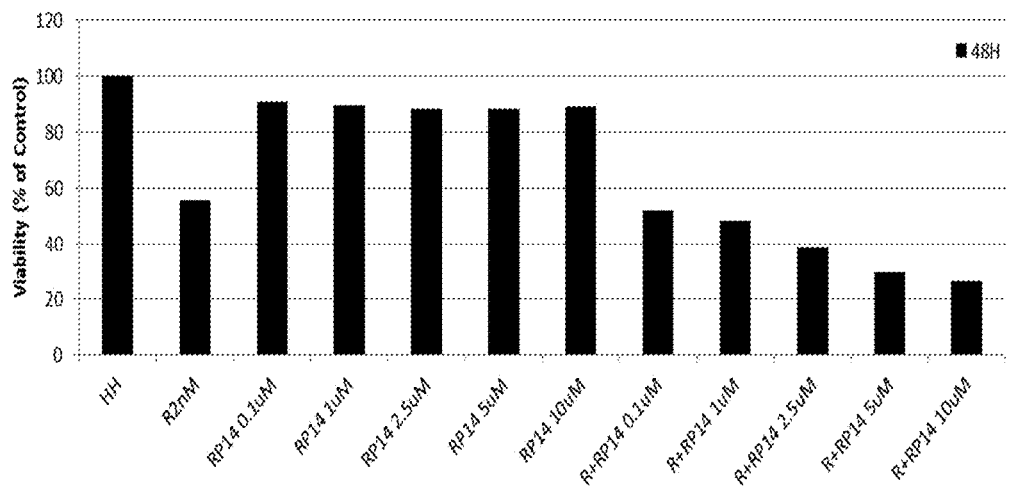
Figure 17C:
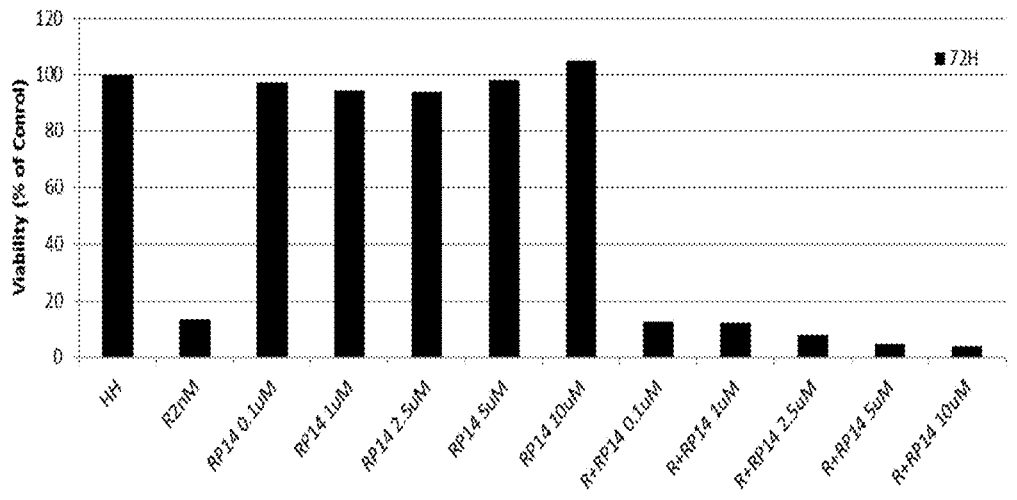
Figure 18A:
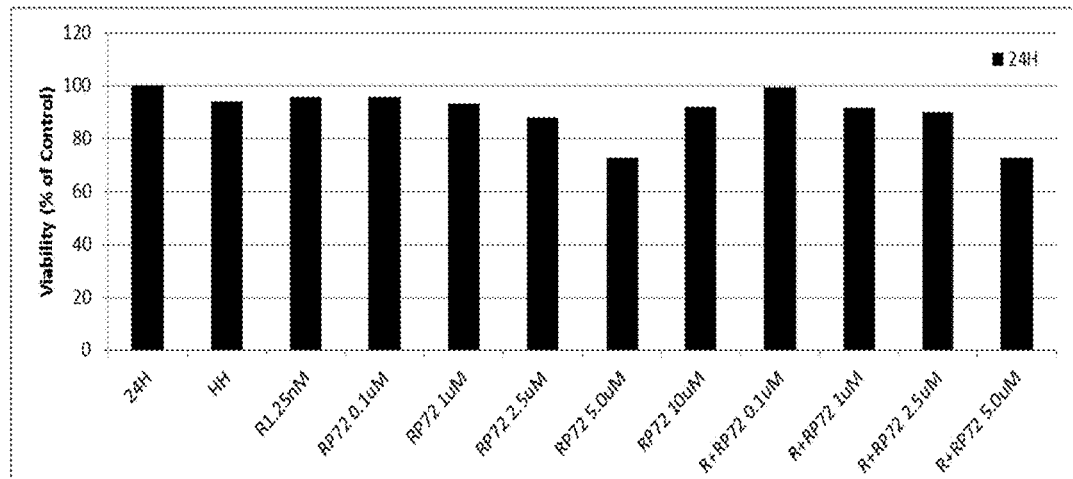
FIGS. 18A-C show synergy between romidepsin and RP72 evaluated by luminetric assays in cell line HH. Cytotoxicity was measured at 24 (A), 48 (B) and 72 (C) hours.
Figure 18B:
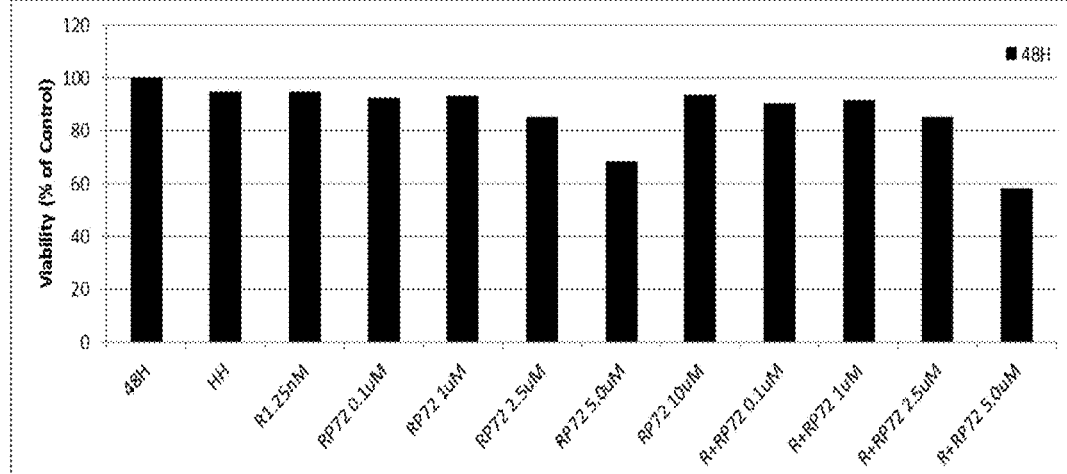
Figure 18C:
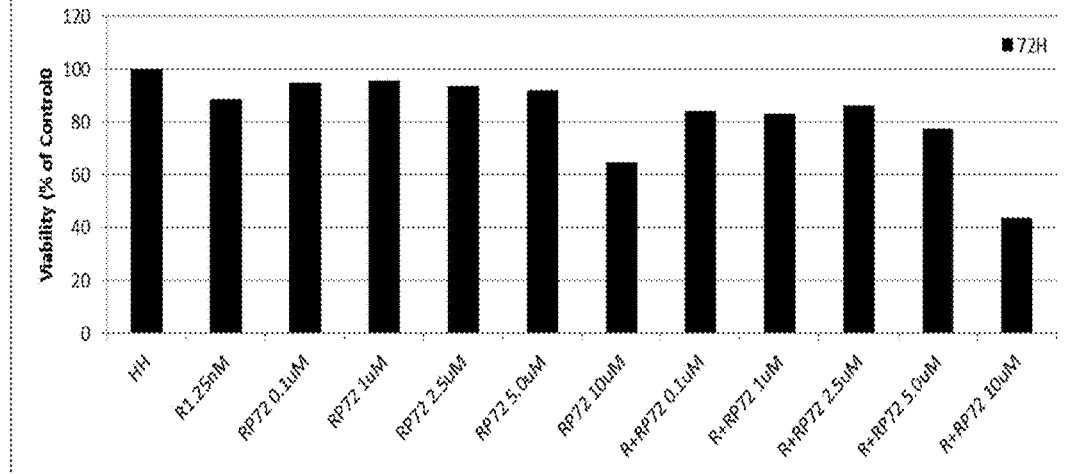

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition such as, for example, cancer or a neurodegenerative disease. The subject in need thereof may or may not be undergoing treatment for conditions related to, for example, cancer or a neurodegenerative disease.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, $21^{st}$ Edition (University of the Sciences in Philadelphia, ed., Lippincott Williams & Wilkins 2005); and Handbook of Pharmaceutical Excipients, $7^{th}$ Edition (Raymond Rowe et al., ed., Pharmaceutical Press 2012); each hereby incorporated by reference in its entirety.

The terms "animal," "subject" and "patient" as used herein includes all members of the animal kingdom including, but not limited to, mammals, animals (e.g., cats, dogs, horses, swine, etc.) and humans.

In some embodiments, the invention is directed to the combination of one or more HAT modulator compounds and one or more HDAC modulator compounds. In some embodiments, the HAT modulator is a HAT activator. In some embodiments, the HAT modulator is a HAT inhibitor. In other embodiments, the HDAC modulator is a HDAC inhibitor. In other embodiments, the HDAC inhibitor is a HDAC activator. In some embodiments, the invention is directed to the combination of one or more HAT activators and one or more HDAC inhibitors. In some embodiments, the invention is directed to the combination of a HAT activator and a HDAC inhibitor. In other embodiments, the combination of a HAT activator and a HDAC inhibitor is unexpectedly effective for killing cancer cells. In other embodiments, the combination of a HAT activator and a HDAC inhibitor is unexpectedly cytotoxic to cancer cells. In some embodiments, the HAT activator increases histone acetylation. In some embodiments, the HDAC inhibitor increases histone acetylation. In some embodiments, the histone acetylation comprises acetylation of histones H2B, H3, H4, or a combination thereof. In some embodiments, the histone acetylation comprises acetylation of histone lysine residues H3K4, H3K9, H3K14, H4K5, H4K8, H4K12, H4K16, or a combination thereof. In some embodiments, the HAT activator increases p53 acetylation. In some embodiments, the HDAC inhibitor increases p53 acetylation. In some embodiments, the HAT activator increases Bcl6 acetylation. In some embodiments, the HDAC inhibitor increases Bcl6 acetylation.

In some embodiments, treatment with a combination of a HAT activator and a HDAC inhibitor can result in a synergistic effect and a reduction in cell viability of cancer cells. The use of a HAT activator in combination with a HDAC inhibitor can allow for a therapeutically effective dose of either the HAT activator, or the HDAC inhibitor, or both, to be administered at a lower dose.

Accordingly, one aspect of the invention is directed to methods for treating cancer in a subject comprising administering to the subject a HAT activator and a HDAC inhibitor.

In some embodiments, the HAT activator is

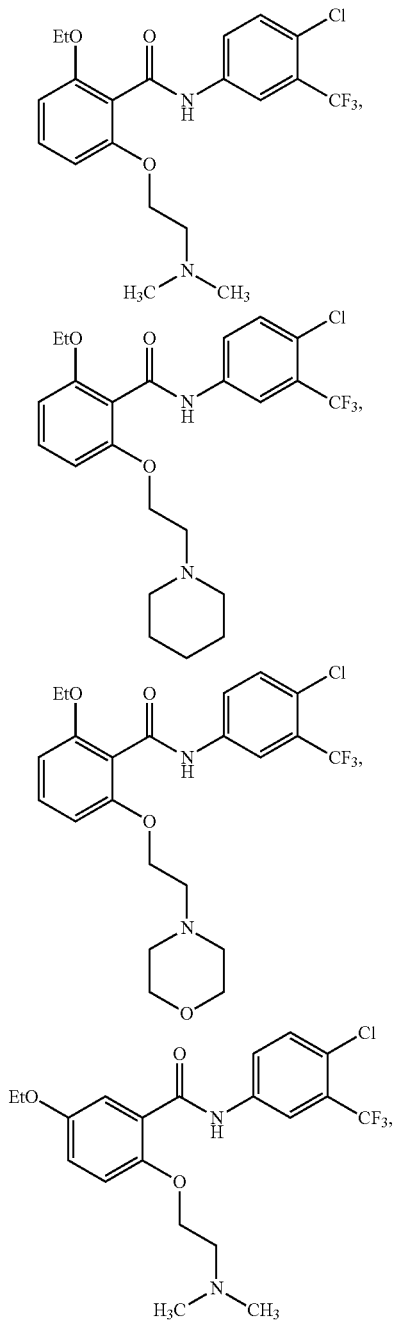

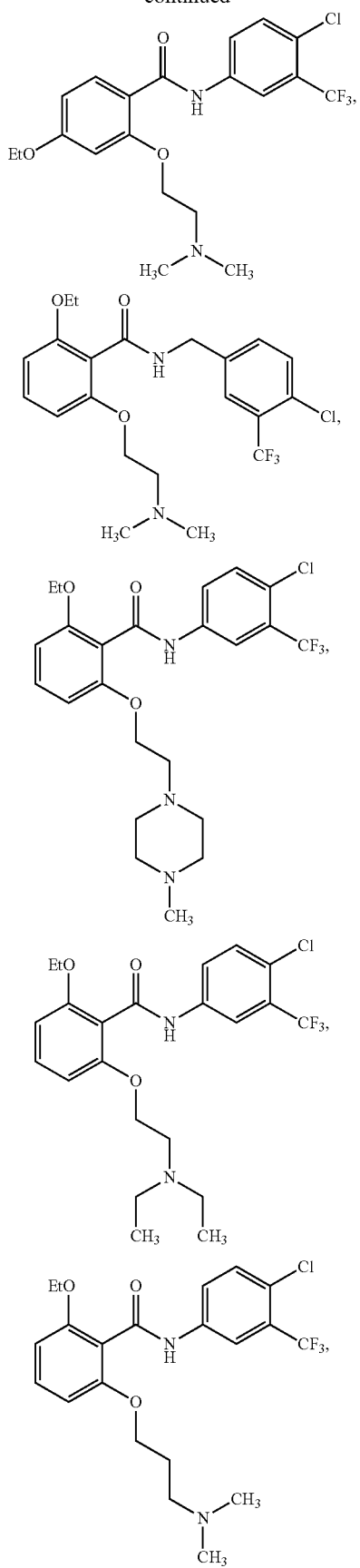

29
-continued
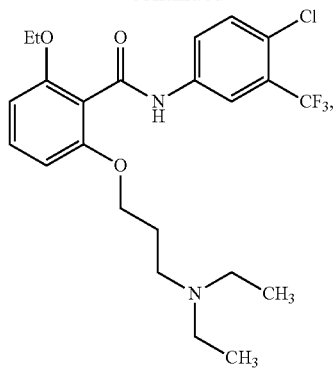
30
-continued
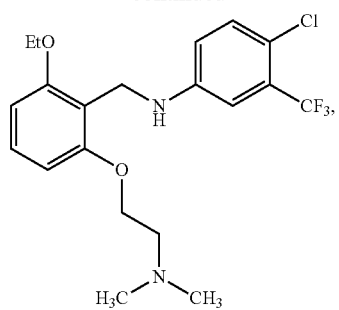
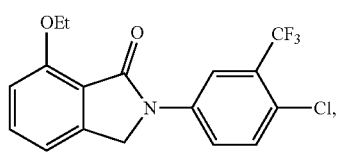
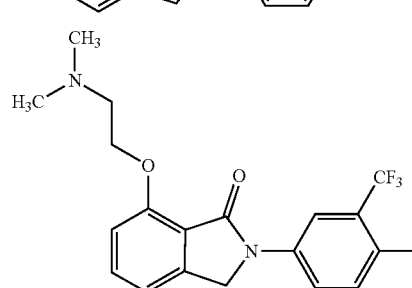
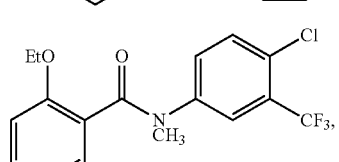
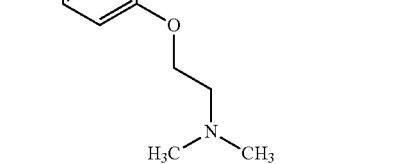
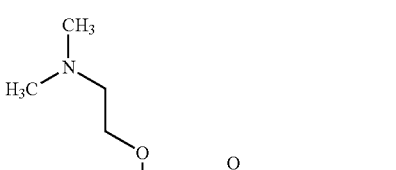
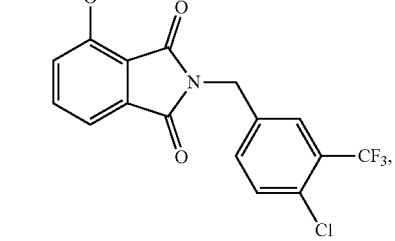
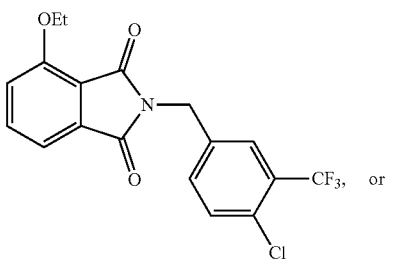

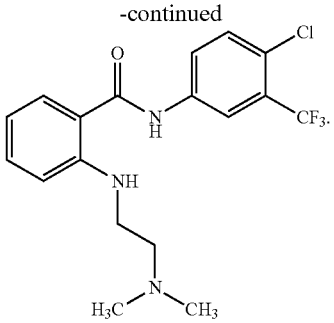

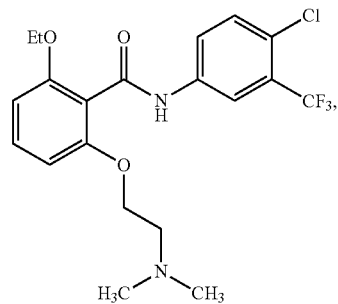 [SMILES: CCOc1cccc(OCCN(C)C)c1C(=O)Nc1ccc(Cl)c(C(F)(F)F)c1]

In some embodiments, the HDAC inhibitor is romidepsin, vorinostat, belinostat, panobinostat, entinostat, mocetinostat, abexinostat, quisinostat, or gavinostat. In another embodiment, the HDAC inhibitor is chidamide, resminostat, givinostat, or kevetrin.

Eukaryotic DNA is highly organized and packaged into the nucleus. The organization and packaging are achieved through the addition of proteins, including core histones H2A, H2B, H3 and H4, which form a complex structure, the chromatin, together with DNA (see, for example, WO 2011/072243 and references cited therein). The modification of core histones is of fundamental importance to conformational changes of the chromatin. The level of acetylation is related to transcription activity, and then the acetylation induces an open chromatin confirmation that allows the transcription machinery access to promoters. Histone deacetylase (HDAC) and histone acetyltransferase (HAT) are enzymes that influence transcription by selectively deacetylating or acetylating the F-amino groups of lysine located near the amino termini of core histone proteins. Chromatin acetylation correlates with transcriptional activity (euchromatin), whereas deacetylation correlates with gene silencing. Further details on HAT, HDAC, chromatin, HAT activators and their role in neurodegenerative diseases and cancer can be found in WO 2011/072243; WO 2012/088420; and U.S. Patent Publication No. 2013/0121919, each incorporated by reference herein in its entirety.

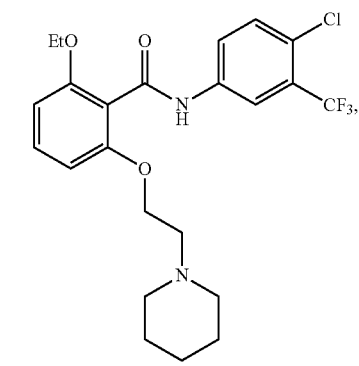

In some embodiments, the HAT modulator compound of the invention is directed to GCN5, GCN5L, HAT1, PCAF, or a combination thereof. Examples of HATs include, but are not limited to GCN5, GCN5L, PCAF, HAT1, ELP3, HPA2, ESA1, SAS2, SAS3, TIP60, HBO1, MOZ, MORF, MOF, SRC1, SRC3, TIF2, GRIP1, ATF-2 [see Lee and Workman (2007) *Nat Rev Mol Cell Biol.*, 8(4):284-95, Marmorstein (2001) *J Molec Biol.* 311: 433-444; and Kimura et al., (2005) *J Biochem.* 138(6): 647-662, which are each hereby incorporated by reference in their entireties]. In some embodiments, the HAT modulator comprises a protein that possesses intrinsic HAT activity, such as nuclear receptor co-activators (for example, CBP/p300 and Taf1). In some embodiments, the acetylation of H2, H3, and/or H4 histones is increased. In some embodiments, the HAT modulator compound is a compound of formula (I). In some embodiments, the HAT modulator compound is selected from the group consisting of:

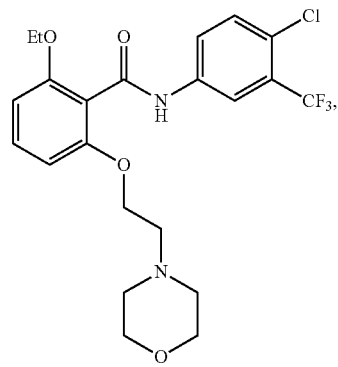

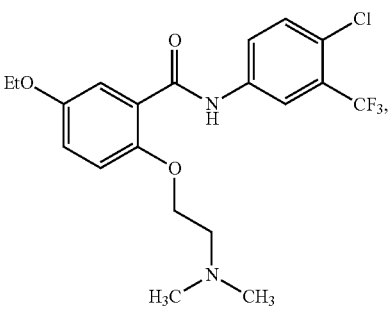

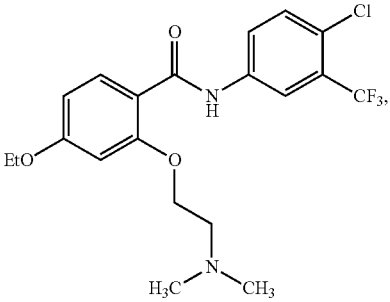

33
-continued
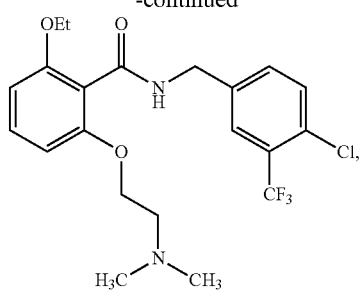
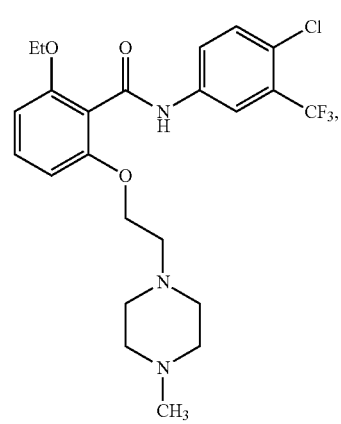
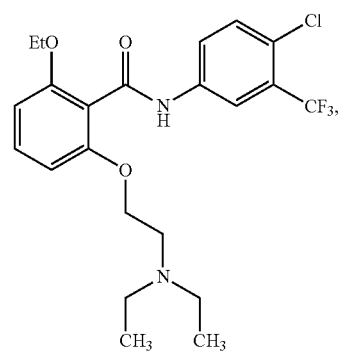
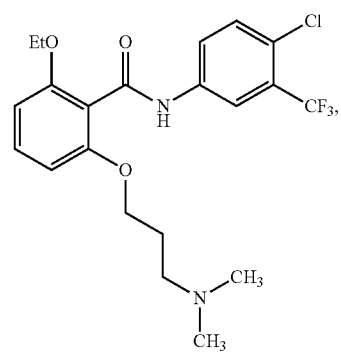
34
-continued
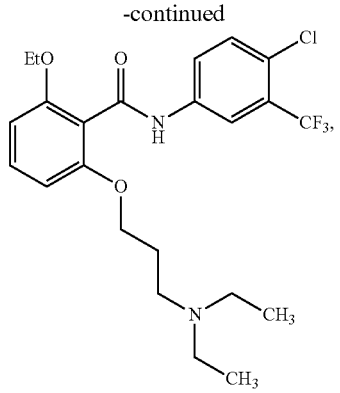
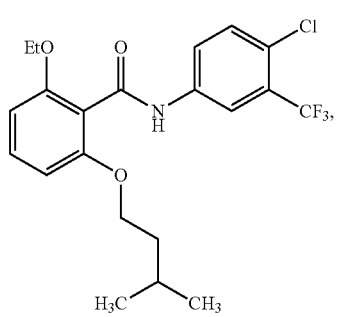
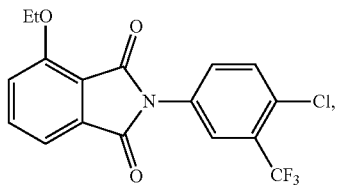
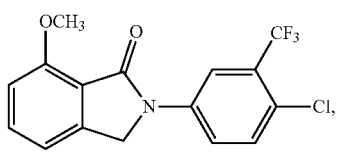
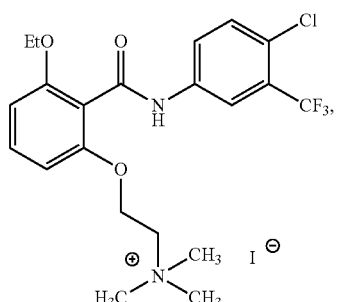
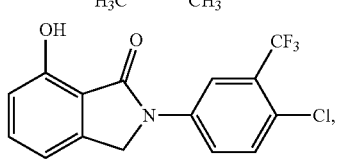

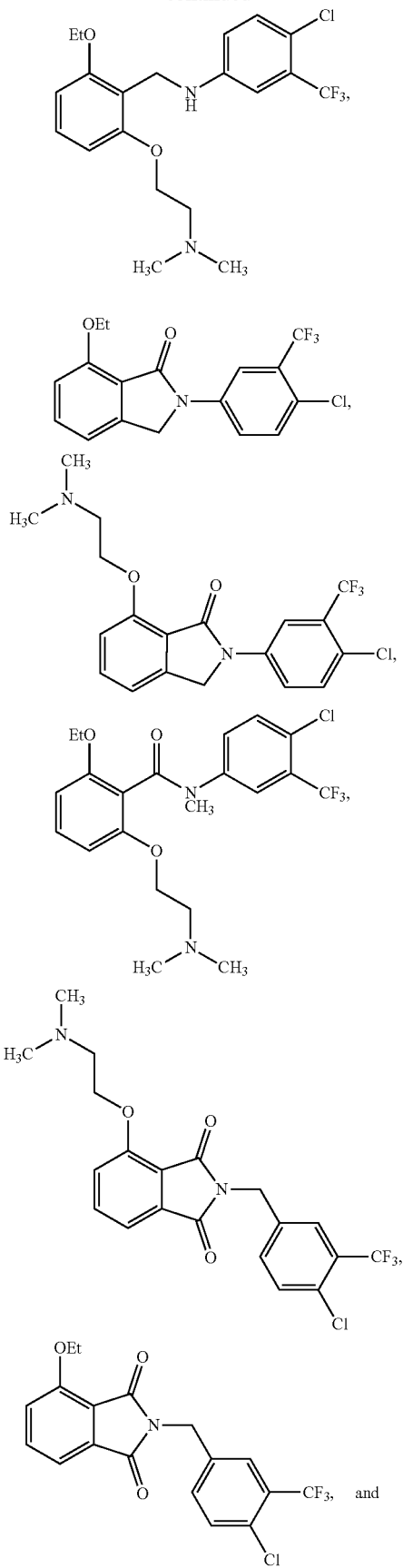

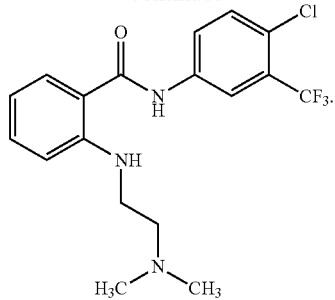

Modulation of the acetylation state of histones, transcription factors, and other regulatory proteins is known to influence their activity within cancer and inflammatory cells. The acetylation state of a protein is controlled by the activity of two main groups of enzymes, histone deacetylases (HDAC) and histone acetyl transferases (HAT). The HDAC removes acetyl-groups while the HATs transfer acetyl-groups to the protein of interest. Classically, modulation of acetylation status is known to influence the condensation of chromatin. In cancer, histones are deacetylated maintaining a condensed chromatin structure, and a transcriptionally silenced state. This transcriptional inactivation is mediated by HDACs which remove acetyl groups from histone tails, maintain a condensed chromatic structure. Inhibitors of HDACs help maintain transcriptionally active chromatin, theoretically allowing for expression of tumor suppressor genes. Two HDAC inhibitors have been approved for the treatment of cancer, including vorinostat and romidepsin, currently FDA approved for the treatment of cutaneous T-cell lymphoma and peripheral T-cell lymphoma.

Since these approvals, the pharmacology of this class of drugs has been extensively studied. One observation that has evolved is that histones are not the only targets of acetylation. It is now accepted that post-translational acetylation of intracellular proteins such as tumor suppressors (p53) and oncogenes (Bcl6) plays a critical role in influencing their activity. It has been established that there is a network of proteins and enzymes that can be modified by acetylation, now collectively referred to as the acetylome. It has been shown that modulation of key intracellular proteins with HDAC inhibitors can lead to profound effects in lymphoma cell lines, in mouse models of lymphoma and in patients with drug-resistant lymphoma. Treatment with HDAC inhibitors, like vorinostat, can inactivate the oncogene, Bcl6, while simultaneously activating the tumor suppressor, p53. The tumor suppress p53 plays an important role in many cancers, and mutations in p53 are critical in the development of many cancers. Enhancement of p53 activity through acetylation protects the tumor suppressor from proteosomal degradation and stimulates induction of apoptosis.

It has also recently been recognized that many patients with diffuse large B-cell lymphoma and follicular lymphoma, the two most common subtypes of lymphoma, harbor inactivating mutations in one of two families of HAT enzymes, CREBBP and p300. These mutations portend a more aggressive phenotype of disease, and shortened survival in mouse models. These mutations are mostly heterozygous, suggesting that the normal haploallele may still be amenable to modification, potentially reversing this malignant phenotype. These mutations have also been identified in B-cell derived acute leukemias.

Given the clinical success of HDAC inhibitors, and the specific HAT mutations in lymphomas, HAT activators may modify the acetylation state of the proteome and may therefore represent a rational therapeutic target for cancer. Furthermore, combined targeting of acetylation through HAT activation and HDAC inhibition may induce profound post-translational modification of key regulatory proteins and 'acetylation stress,' leading to the induction of programmed cell death.

Relapsed and refractory T-cell lymphoma continues to be a rare but extraordinarily aggressive disease. HDAC inhibitors are approved for use in peripheral T-cell lymphoma and cutaneous T-cell lymphoma. In addition, diffuse large B-cell lymphoma and follicular lymphomas are the two most common subtypes of lymphoma and harbor heterogenous inactivating mutations in HATs. Without being bound by theory, the effects of these mutations can be mitigated by enhancement of their effect through pharmacologic modification. Treatment with HAT activators in cells with HAT mutations can reverse the malignant phenotype. These mutations can not be modulated by existing HDAC inhibitors.

Histone deacetylase inhibitors have activity on a set of enzymes that remove acetyl groups from histones and transcription factors. Although HAT activators and HDAC inhibitors have converse mechanisms of action, their end result is to enforce acetylation of histones and transcription factors. HAT activators have a converse mechanism of action from known agents with similar effects. They can reverse the malignant genotype of mutated HATs in follicular and diffuse large B-cell lymphomas as well as B-cell derived acute leukemias. These actions would not be possible with HDAC inhibitors alone. HAT activators can be used to overcome inactivating mutations of HATs, which is not possible with any known or existing technology. In some embodiments, a HAT modulator can enhance HDAC inhibitor activity. They may reverse a malignant phenotype of diffuse large 3-cell lymphoma and follicular lymphoma harboring FIAT mutations. HAT activators can activate key tumor suppressor proteins such as p53.

In some embodiments, the invention described herein can be used to treat inflammatory diseases such as lupus, rheumatoid arthritis, and Sjogren's syndrome, as well as, a host of neurodegenerative diseases including Alzheimer's Disease, Huntington disease, Friederich Ataxia, and others.

In some embodiments, there is also provided a method for reducing the proliferation of a cancer cell or cells comprising contacting the cell(s) with a HAT modulator and a HDAC modulator. In similar embodiments there is provided a use of a HAT modulator and a HDAC modulator for reducing the proliferation of a cancer cell or cells. In some embodiments, there is provided a method for inducing cell death in a cancer cell or cells comprising contacting the cell(s) with a HAT modulator and a HDAC modulator. In similar embodiments there is provided a use of a HAT modulator and a HDAC modulator for inducing cell death in a cancer cell or cells. In some embodiments, the HAT modulator is a HAT activator. In some embodiments, the HAT modulator is a HAT inhibitor. In other embodiments, the HDAC modulator is a HDAC inhibitor. In other embodiments, the HDAC inhibitor is a HDAC activator. In some embodiments, the invention is directed to the combination of one or more HAT activators and one or more HDAC inhibitors. In some embodiments, the invention is directed to the combination of a HAT activator and a HDAC inhibitor. In some embodiments, the cancer cell may be in vivo or in vitro. In some embodiments, the cancer cell may be a precancerous cell. In some embodiments, the cancer is Hodgkin's lymphoma, non-Hodgkin's lymphoma, B cell lymphoma, T cell lymphoma, or follicular lymphoma. In other embodiments, the B cell lymphoma is diffuse large B-cell lymphoma. In further embodiments, the diffuse large B-cell lymphoma is a germinal center-derived diffuse large B cell lymphoma, an activated B-cell-derived (ABC) diffuse large B-cell lymphoma, or a non-germinal center diffuse large B cell lymphoma. In some embodiments, the HDAC inhibitor is romidepsin, vorinostat, belinostat, panobinostat, entinostat, mocetinostat, abexinostat, quisinostat or gavinostat.

Increasing histone acetylation has been shown to improve outcome in a wide variety of diseases as diverse as asthma, infectious disease and psychiatric diseases. Although clinical trials of several HDAC inhibitors are currently underway, the alternative strategy where by histone acetylation is increased by HAT modulator has not been extensively explored. For example, compounds in U.S. Patent Publication No. US2009/076155 and PCT Publication No. WO2004/053140 (which are each hereby incorporated by reference in their entireties) have poor solubility and membrane permeability. Other HAT modulators are described in WO 2011/072243; WO 2012/088420; and U.S. Patent Publication No. 2013/0121919, each incorporated by reference herein in its entirety.

Several HDACi are in trials for cancer some of which are, for example, 4SC-202 (Nycomed, Germany), which is in a Preclinical stage; AR-42 (Arno therapeutics, Parsippany, N.J.) which is in a Preclinical stage; Belinostat (TopoTarget, Rockaway, N.J.) which is in Phase II clinical trials; and Entinostat (Bayer Schering) which is in Phase II clinical trials. For example, in Table 3 of Lane and Chabner (2009, *J Clin Oncol.,* 27(32):5459-68; incorporated by reference in its entirety), selected clinical trials of HDAC inhibitors are discussed, which include Vorinostat, Depsipeptide, and MGCD0103. In Table 2 of Lane and Chabner (2009, *J Clin Oncol.,* 27(32):5459-68; incorporated by reference in its entirety), selected HDAC inhibitors in clinical use or development are discussed, which include hydroxamic acid compounds (e.g., Vorinostat, Trichostatin A, LAQ824, Panobinostat, Belinostat, and ITF2357), cyclic tetrapeptide compounds (e.g., Depsipeptide), benzamide compounds (e.g., Entinostat and MGCD0103), and short-chain aliphatic acid compounds (e.g., valproic acid, phenyl butyrate, and pivanex). Other HDAC inhibitors include, but are not limited to, romidepsin, vorinostat, belinostat, panobinostat, entinostat, mocetinostat, abexinostat, quisinostat or gavinostat. In another embodiment, the HDAC inhibitor is chidamide, resminostat, givinostat, or kevetrin.

Vorinostat, also known as Zolinza® (Merck, Whitehouse Station, N.J.) inhibits the enzymatic activity of histone deacetylases HDAC1, HDAC2 and HDAC3 (Class I) and HDAC6 (Class II). In vitro, vorinostat causes the accumulation of acetylated histones and induces cell cycle arrest and/or apoptosis of some transformed cells. Vorinostat is indicated for the treatment of cutaneous manifestations in patients with cutaneous T-cell lymphoma (CTCL) who have persistent or recurrent disease on or following two systemic therapies. Further details on vorinostat are discussed in the Zolina® label, incorporated by reference in its entirety.

Romidepsin, also known as Istodax® (Celgene, Summit, N.J.) is a bicyclic depsipeptide and inhibits histone deacetylases. In vitro, romidepsin causes the accumulation of acetylated histones and induces cell cycle arrest and/or apoptosis of some cancer cell lines. Romidepsin is indicated for the treatment of cutaneous T-cell lymphoma (CTCL) in patients who have received at least one prior systemic therapy and for the treatment of peripheral T-cell lymphoma (PTCL) in patients who have received at least one prior systemic therapy. Further details on romidepsin are discussed in the Istodax® label, incorporated by reference in its entirety.

Some HDACi are or were being developed for neurological diseases, such as an HDACi from Merck (Whitehouse Station, N.J.) that is being used for the treatment of neurodegenerative diseases; and HDACi from TopoTarget (Rockaway, N.J.) that was being used for the treatment of Huntington's disease, now discontinued; isovaleramide NPS-1776 (NPS Pharmaceutical, Bedminster, N.J.) that was being used for bipolar disorder, epilepsy, and migraines, now discontinued; and a histone acetyltransferase inhibitor for cancer from TopoTarget A/S (København, Denmark), which was discontinued in the preclinical stage.

In some embodiments, the HAT modulator and HDAC modulator combinations may have a synergistic effect, for example, HAT activator and HDAC inhibitor combinations can result in increased histone acetylation compared to histone acetylation of the HAT activator or HDAC inhibitor alone. Combined targeting of acetylation through HAT activation and HDAC inhibition may induce profound post-translational modification of key regulatory proteins and 'acetylation stress,' leading to the induction of programmed cell death. In some embodiments, HAT activator and HDAC inhibitor combinations may lead to acetylation of p53, acetylation of Bcl6 and/or induction of p21.

In some embodiments, the methods include administering a HAT activator and HDAC inhibitor to a subject, wherein the subject is wildtype for all HAT enzymes. In some embodiments, the methods include administering a HAT activator and HDAC inhibitor to a subject, wherein the subject has at least one mutant HAT enzyme gene. In some embodiments, the methods include administering a HAT activator and HDAC inhibitor to a subject, the subject has a wildtype EP300 and wildtype CREBBP gene. In another embodiment, the subject has a wildtype EP300 and CREBBP mutant gene. In a specific embodiment, the CREBBP mutant gene comprises a mismatch mutation. In another specific embodiment, the CREBBP mutant gene comprises a truncation mutation. In another specific embodiment, the CREBBP mutant gene comprises at least one point mutation. In a specific embodiment, the mutation is on only one allele of CREBBP.

In another embodiment, the subject has a mutant EP300 and CREBBP wildtype gene. In a specific embodiment, the EP300 mutant gene comprises a mismatch mutation. In another specific embodiment, the EP300 mutant gene comprises a truncation mutation. In another specific embodiment, the EP300 mutant gene comprises at least one point mutation. In a specific embodiment, the mutation is on only one allele of EP300.

In another embodiment, the subject has a mutant EP300 and CREBBP mutant gene. In a specific embodiment, the EP300 mutant gene and/or CREBBP mutant gene comprises a mismatch mutation. In another specific embodiment, the EP300 mutant gene and/or CREBBP mutant gene comprises a truncation mutation. In another specific embodiment, the EP300 mutant gene and/or CREBBP mutant gene comprises at least one point mutation. In a specific embodiment, the EP300 mutant gene has a mismatch mutation and the CREBBP mutant gene has a truncated mutation. In a specific embodiment, the mutation is on only one allele of CREBBP and/or on only one allele of EP300. In another embodiment, methods include administering a HAT activator and HDAC inhibitor to a subject for the treatment and/or inhibition of lymphoma. In a specific embodiment, the lymphoma is diffuse large B-cell lymphoma and/or follicular lymphoma. In another embodiment, methods include administering a HAT activator and HDAC inhibitor to a subject for the treatment and/or inhibition of B-cell derived acute leukemias. In a specific embodiment, the HAT activator is

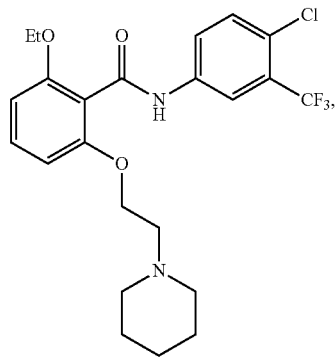 [SMILES: CCOc1cccc(OCCN2CCCCC2)c1C(=O)Nc1ccc(Cl)c(C(F)(F)F)c1]

or a pharmaceutically acceptable salt thereof. In another specific embodiment, the HAT activator is

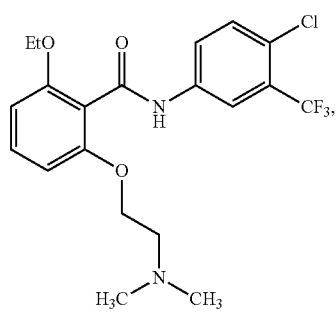 [SMILES: CCOc1cccc(OCCN(C)C)c1C(=O)Nc1ccc(Cl)c(C(F)(F)F)c1]

or a pharmaceutically acceptable salt thereof.

In another specific embodiment, the HDAC inhibitor is romidepsin.

In some embodiments, a HAT modulator compound can be used in combination with one or more HDAC modulators to treat a cancer in a subject in need thereof. In other embodiments, a HAT activator compound can be used in combination with one or more HDAC inhibitors to treat a cancer in a subject in need thereof. Non-limiting examples of cancers include B cell lymphoma, colon cancer, lung cancer, renal cancer, bladder cancer, T cell lymphoma, myeloma, leukemia, chronic myeloid leukemia, acute myeloid leukemia, chronic lymphocytic leukemia, acute lymphocytic leukemia, hematopoietic neoplasias, thymoma, lymphoma, sarcoma, lung cancer, liver cancer, non-Hodgkin's lymphoma, Hodgkin's lymphoma, uterine cancer, renal cell carcinoma, hepatoma, adenocarcinoma, breast cancer, pancreatic cancer, liver cancer, prostate cancer, head and neck carcinoma, thyroid carcinoma, soft tissue sarcoma, ovarian cancer, primary or metastatic melanoma, squamous cell carcinoma, basal cell carcinoma, brain cancer, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, astrocytoma, medulloblastoma, craniopharyngioma, ependymoma, pinealoma, hemangioblastoma, acoustic neuroma, oligodendroglioma, meningioma, retinoblastoma, leukemia, melanoma, neuroblastoma, small cell lung carcinoma, bladder carcinoma, lymphoma, multiple myeloma, follicular lymphoma and medullary carcinoma.

In some embodiments, the cancer is colon cancer, lung cancer, renal cancer, leukemia, CNS cancer, melanoma, ovarian cancer, breast cancer, or prostate cancer.

In some embodiments, the cancer is colon cancer, renal cancer, T cell leukemia, myeloma, leukemia, acute myeloid leukemia, acute lymphocytic leukemia, renal cell carcinoma, adenocarcinoma, glioblastoma, breast carcinoma, prostate carcinoma, or lung carcinoma.

In some embodiments, the cancer is Hodgkin's lymphoma, non-Hodgkin's lymphoma, B cell lymphoma, T cell lymphoma, or follicular lymphoma. In other embodiments, the B cell lymphoma is diffuse large B-cell lymphoma. In further embodiments, the diffuse large B-cell lymphoma is a germinal center-derived diffuse large B cell lymphoma, an activated B-cell-derived (ABC) diffuse large B-cell lymphoma, or a non-germinal center diffuse large B cell lymphoma.

In some embodiments, a HAT modulator compound can be used in combination with one or more HDAC modulators to treat a neurodegenerative disease in a subject in need thereof. In other embodiments, a HAT activator compound can be used in combination with one or more HDAC inhibitors to treat a neurodegenerative disease in a subject in need Non-limiting examples of neurodegenerative diseases include Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Hunting-ton's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases Progressive Supranuclear Palsy, Refsum's disease, Rett's syndrome, Tau-positive FrontoTemporal dementia, Tau-negative FrontoTemporal dementia, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes *dorsalis*, and Toxic encephalopathy.

In some embodiments, the neurodegenerative disease is selected from Alzheimer's Disease, ALS, Parkinson's Disease, and Huntington's Disease. In some embodiments, the neurodegenerative disease is Alzheimer's Disease. In some embodiments, the neurodegenerative disease is Huntington's Disease.

Epigenetic modifications including acetylation of histones may contribute to gene expression changes important to learning and memory (*Science* 2010: 328(5979), 701-702; herein incorporated by reference in its entirety). Addition of acetyl groups to histones by histone acyltransferases (HAT) enhances gene expression, while their removal by histone deacetylases (HDAC) reduces gene expression. Reduction in histone acetylation has recently been linked to age-induced memory impairment and various neurodegenerative diseases (*Science* 2010: 328(5979), 701-702; herein incorporated by reference in its entirety). HDAC inhibitors have been shown to enhance memory in mice (*Nature* 459, 55-60 (7 May 2009); herein incorporated by reference in its entirety). Although clinical trials of several HDAC inhibitors are currently underway to try to prevent deacetylation, the alternative strategy of increasing histone acetylation by activating HAT has not been significantly explored. Histone acetylation is discussed in, for example, U.S. Patent Publication Nos. 2010/0166781; 2010/0144885; 2009/0076155; *Neuroscience* 2011, 194, 272-281; and *J. Phys. Chem B* 2007, 111(17), 4527-4534 (each of which herein incorporated by reference in its entirety). Further details on neurodegenerative diseases, including Alzheimer's disease, can be found in WO 2011/072243 and WO 2012/088420, each incorporated by reference herein in its entirety.

In some embodiments, the invention provides for compounds with histone acetyltransferase activity which can be used in combination with one or more HDAC modulators to treat patients with cancers or neurodegenerative diseases. In some embodiments, the compounds are HAT activators. In some embodiments, the compounds are HAT inhibitors. In some embodiments, the HDAC modulator is a HDAC activator. In some embodiments, the HDAC modulator is a HDAC inhibitor. In some embodiments, the compounds have good HAT activation potency, high selectivity, reasonable pharmacokinetics and/or good permeability across the blood-brain-barrier (BBB). In some embodiments, these compounds can be used as therapy with decreased side effects for AD patients. In some embodiments, the compounds improve cognition or memory in AD and Alzheimer's-like pathologies, as well as minimize the side effects for subjects afflicted with other neurodegenerative diseases. In some embodiments, the compounds of the invention can also be developed as anti-cancer therapies. In some embodiments, acetylation of histone proteins increases gene expression in a subject resulting in enhanced memory and cognition.

In some embodiments, the invention provides a method for reducing amyloid beta (A) protein deposits in a subject in need thereof, the method comprising administering to the subject a HAT activator and a HDAC inhibitor. In some embodiments, the subject exhibits abnormally elevated levels of amyloid beta plaques. In some embodiments, the subject is afflicted with Alzheimer's disease, Lewy body dementia, inclusion body myositis, or cerebral amyloid angiopathy.

In further embodiments, the invention provides for the utilization of HAT agonists in combination with one or more HDAC modulators as memory enhancers in normal subjects (for example, a subject not afflicted with a neurodegenerative disease). In further embodiments, the invention provides for the utilization of HAT agonists in combination with one or more HDAC modulators as memory enhancers in aging subjects (for example, a subject who is >55 years old). In further embodiments, the invention provides for the utilization of HAT agonists in combination with one or more HDAC modulators as memory enhancers for other conditions associated with cognitive decrease/impairment. In some embodiments, the HDAC modulator is a HDAC activator. In some embodiments, the HDAC modulator is a HDAC inhibitor. Non-limiting examples of conditions associated with cognitive decrease/impairment include a variety of syndromes associated with mental retardation and syndromes associated with learning disabilities, Parkinson's disease, Pick's disease, a Lewy body disease, amyotrophic lateral sclerosis, Huntington's disease, Creutzfeldt-Jakob disease, Down syndrome, multiple system atrophy, neuronal degeneration with brain iron accumulation type I (Hallervorden-Spatz disease), pure autonomic failure, REM sleep behavior disorder, mild cognitive impairment (MCI), cerebral amyloid angiopathy (CAA), mild cognitive deficits, aging, vascular dementias mixed with Alzheimer's disease, a neurodegenerative disease characterized by abnormal amyloid deposition, and any combination thereof.

In some embodiments, the invention provides methods for identifying a combination of one or more HAT modulators and one or more HDAC modulators that can acetylate histone proteins thus increasing gene expression in a subject resulting in enhanced memory and cognition. In some embodiments, the invention provides methods for identifying a combination of one or more HAT activators and one or more HDAC inhibitors can acetylate histone proteins thus increasing gene expression in a subject resulting in enhanced memory and cognition.

To shrink the candidate pool of HAT modulator and HDAC modulator combinations to be tested in animal models of neurodegenerative diseases, such as animals that exhibit elevated levels of inclusion bodies, for example Aβ accumulation animal models (e.g., animal models of AD), or, for example, a mouse model for Huntington's disease, HAT modulators or HDAC modulators can first be screened or selected based on their possession of certain characteristics, such as having one or more of: an $EC_{50}$ no greater than about 100 nM; a histone acetylation activity in vitro; and the ability to penetrate the BBB. HAT modulator and HDAC modulator combinations can first be screened or selected based on their possession of certain characteristics, such as having a histone acetylation activity in vitro or resulting in increased histone acetylation in vitro compared to histone acetylation in vitro of the HAT modulator or HDAC modulator alone.

In some embodiments, the candidate pool of HAT modulator and HDAC modulator combinations can be tested in animal models of neurodegenerative diseases, such as, but not limited to, animals that exhibit elevated levels of inclusion bodies, for example A accumulation animal models (e.g., animal models of AD), or a mouse model for Huntington's disease to determine whether they increase gene expression in a subject resulting in enhanced memory and cognition. As used herein, a HAT activator compound does not necessarily preclude the possibility that the compound may also be able to inhibit other HATs. As used herein, a HDAC inhibitor compound does not necessarily preclude the possibility that the compound may also be able to activate other HATs.

In some embodiments, the compounds of the invention are HAT modulators. The term "modulate", as it appears herein, refers to a change in the activity or expression of a protein molecule. For example, modulation can cause an increase or a decrease in protein activity, binding characteristics, or any other biological, functional, or immunological properties of a secretase protein molecule. In some embodiments, the compounds activate HAT. In some embodiments, the compounds inhibit HAT.

In some embodiments, the compounds of the invention are HDAC modulators. The term "modulate", as it appears herein, refers to a change in the activity or expression of a protein molecule. For example, modulation can cause an increase or a decrease in protein activity, binding characteristics, or any other biological, functional, or immunological properties of a secretase protein molecule. In some embodiments, the compounds inhibit HDAC. In some embodiments, the compounds activate HDAC.

A HAT modulator compound can be a compound that increases the activity and/or expression of a HAT molecule (e.g., GCN5, GCN5L, PCAF, or HAT1) in vivo and/or in vitro. HAT modulator compounds can be compounds that exert their effect on the activity of a HAT protein via the expression, via post-translational modifications, or by other means. In some embodiments, a HAT modulator compound increases HAT protein or mRNA expression, or acetyltransferase activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

A HDAC modulator compound can be a compound that decreases the activity and/or expression of a HDAC molecule in vivo and/or in vitro. HDAC modulator compounds can be compounds that exert their effect on the activity of a HDAC protein via the expression, via post-translational modifications, or by other means. In some embodiments, a HDAC modulator compound decreases HDAC protein or mRNA expression, or deacetyltransferase activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

Test compounds or agents that bind to a HAT molecule (such as GCN5, GCN5L, PCAF, or HAT1), and/or have a stimulatory effect on the activity or the expression of a HAT molecule, can be identified by various assays. The assay can be a binding assay comprising direct or indirect measurement of the binding of a test compound or a known HAT ligand to the active site of a HAT protein. The assay can also be an activity assay comprising direct or indirect measurement of the activity of a HAT molecule. The assay can also be an expression assay comprising direct or indirect measurement of the expression of a HAT mRNA or protein. The various screening assays can be combined with an in vivo assay comprising measuring the effect of the test compound on cognitive and synaptic function in an animal model for neurodegenerative disorders, such as, but not limited to, AD or Huntington's Disease. The assay can be an assay comprising measuring the effect of the test compounds on cell viability. In one embodiment, the cells are cancer cells, such as, but not limited to B-cell lymphoma cell lines, or T-cell lymphoma cell lines (e.g. Ly1, Ly7, Ly10, SU-DHL2, HH, or H9 cell lines).

The inhibitors of the expression of a HAT molecule can be identified via contacting a HAT-positive cell or tissue with a test compound and determining the expression of a HAT protein or HAT mRNA in the cell. The protein or mRNA expression level of a HAT molecule in the presence of the test compound can be compared to the protein or mRNA expression level of a HAT protein in the absence of the test compound. The test compound can then be identified as an inhibitor of expression of a HAT protein (such as GCN5, GCN5L, PCAF, or HAT1) based on this comparison. In other words, the test compound can also be a HAT inhibitor compound (such as an antagonist).

Activators of the expression of a HAT molecule can also be identified via contacting a HAT-positive cell or tissue with a test compound and determining the expression of a HAT protein or HAT mRNA in the cell. The protein or mRNA expression level of a HAT molecule in the presence of the test compound can be compared to the protein or mRNA expression level of a HAT protein in the absence of the test compound. The test compound can then be identified as an activator of expression of a HAT protein (such as GCN5, GCN5L, PCAF, or HAT1) based on this comparison. For example, when expression of HAT protein or mRNA is statistically or significantly more in the presence of the test compound than in its absence, the compound is identified as an activator of the expression of a HAT protein or mRNA. In other words, the test compound can also be a HAT activator compound (such as an agonist). The expression level of a HAT protein or mRNA in cells can be determined by methods described herein.

Determining the ability of a test compound to bind to a HAT molecule, a HDAC molecule or a variant thereof can be accomplished using real-time Bimolecular Interaction Analysis (BIA) [McConnell, (1992); Sjolander, S., and Urbaniczky, C. Integrated fluid handling system for biomolecular interaction analysis. *Anal. Chem.* 1991, 63, 2338-2345; herein incorporated by reference in its entirety]. BIA is a technology for studying biospecific interactions in real time, without labeling any of the interactants (e.g., BIA-Core™). Changes in optical phenomenon surface plasmon resonance (SPR) can be used as an indication of real-time reactions between biological molecules.

In some embodiments, the invention provides for compounds that bind to a HAT activator protein, such as GCN5, GCN5L, PCAF, or HAT1. These compounds can be identified by the screening methods and assays described herein, and enhance the activity or expression of HAT activator proteins.

Test compounds or agents that bind to a HAT molecule and/or have a stimulatory effect on the activity or the expression of a HAT molecule, can be combined with one or more test compounds or agents that bind to a HDAC molecule. The assay can be an activity assay comprising direct or indirect measurement of the activity of a HAT molecule and/or a HDAC molecule. The assay can also be an expression assay comprising direct or indirect measurement of the expression of a HAT mRNA or protein and/or a HDAC mRNA or protein. The various screening assays can be combined with an in vivo assay comprising measuring the effect of a HAT activator and a HDAC inhibitor on cognitive and synaptic function in an animal model for neurodegenerative disorders, such as, but not limited to, AD or Huntington's Disease. The assay can be an assay comprising measuring the effect of the test compounds on cell viability. In one embodiment, the cells are cancer cells, such as, but not limited to B-cell lymphoma cell lines, or T-cell lymphoma cell lines. In one embodiment, the effect of a HAT activator and one or more HDAC inhibitors in combination is compared to the effect of a HAT activator or HDAC inhibitor alone.

Synthesis of representative HAT activators is disclosed, for example, in WO 2011/072243; WO12/088420 and US Patent Pub. No. 2013/0121919; each herein incorporated by reference in its entirety.

In some embodiments, the HAT activator is a compound of formula (I),

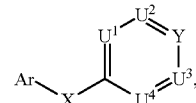

wherein,

Ar is

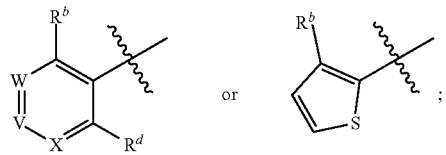

$R^a$ is H, $C_1$-$C_6$-alkyl, $C_1$-$C_6$-haloalkyl, O—($C_1$-$C_6$-alkyl), O—($C_1$-$C_6$-haloalkyl), halogen, CN, or $NO_2$;

$R^b$ is H, OH, halogen, $C_1$-$C_6$-alkyl, —($C_1$-$C_6$-alkyl)$CO_2$—($C_1$-$C_6$-alkyl), $C_1$-$C_6$-haloalkyl, $C_2$-$C_6$-alkenyl, $C_3$-$C_8$-cycloalkyl, $C_2$-$C_6$-heteroalkyl, $C_3$-$C_8$-heterocycloalkyl, aryl, heteroaryl, O—($C_1$-$C_6$-alkyl), O—($C_1$-$C_6$-alkyl)$CO_2$—($C_1$-$C_6$-alkyl), O—($C_1$-$C_6$-haloalkyl), O—($C_3$-$C_8$-cycloalkyl), O—($C_2$-$C_6$-alkenyl), O—($C_3$-$C_8$-heterocycloalkyl), $N(R^{10})$—($C_1$-$C_6$-alkyl), $N(R^{10})$—($C_1$-$C_6$-alkyl)$CO_2$—($C_1$-$C_6$-alkyl), $N(R^{10})$—($C_3$-$C_8$-cycloalkyl), SH, S—($C_1$-$C_6$-alkyl), S—($C_1$-$C_6$-alkyl)$CO_2$—($C_1$-$C_6$-alkyl), $SO_2$—($C_1$-$C_6$-alkyl), $SO_2$—($C_1$-$C_6$-alkyl)$CO_2$—($C_1$-$C_6$-alkyl), O—($C_2$-$C_6$-alkyl)-$N(R^{10})_2$, O—($C_2$-$C_6$-alkyl)-$N(R^{10})_3{}^+$halogen$^-$, O—($C_3$-$C_8$-cycloalkyl)-$N(R^{10})_2$, $N(R^{10})$—($C_2$-$C_6$-alkyl)-$N(R^{10})_2$, —($C_1$-$C_6$-alkyl)-$N(R^{10})_2$, —($C_1$-$C_6$-alkyl)-$R^3$, O—($C_1$-$C_6$-alkyl)-$R^3$, O—($C_3$-$C_8$-cycloalkyl)-$R^3$, $N(R^{10})$—($C_1$-$C_6$-alkyl)-$R^3$, O-aryl, or O-heteroaryl;

$R^c$ is H, —($C_1$-$C_6$-alkyl), O—($C_1$-$C_6$-alkyl), C(=O)NH-phenyl, wherein phenyl is substituted with one or more halo or haloalkyl;

$R^d$ is H, OH, halogen, $C_1$-$C_{16}$-alkyl, $C_1$-$C_{16}$-haloalkyl, O—($C_3$-$C_8$-cycloalkyl), O—($C_3$-$C_8$-heterocycloalkyl), O—($C_2$-$C_6$-alkenyl), O—($C_1$-$C_6$-alkyl), O—($C_1$-$C_6$-alkyl)-phenyl, O—($C_2$-$C_6$-alkyl)-$N(R^{10})_2$, O—($C_2$-$C_6$-alkyl)-$N(R^{10})_3{}^+$halogen$^-$, —($C_1$-$C_6$-alkyl)-$R^3$, O—($C_1$-$C_6$-alkyl)-$R^3$, O S($C_1$-$C_6$-alkyl), $N(R^{10})$—($C_1$-$C_6$-alkyl)-$R^3$, —$N(R^{10})$—($C_1$-$C_6$-alkyl), —$N(R^{10})$—($C_2$-$C_6$-alkenyl), —$N(R^{10})$—($C_3$-$C_8$-cycloalkyl), —$N(R^{10})$—($C_3$-$C_8$-heterocycloalkyl), $N(R^{10})$—($C_2$-$C_6$-alkyl)-$N(R^{10})_2$—($C_1$-$C_6$-alkyl)-$N(R^{10})_2$, S—($C_2$-$C_6$-alkyl)-$N(R^{10})_2$, $OCH_2C(O)O(C_1$-$C_6$-alkyl), O-aryl, N-aryl, O-heteroaryl, or N-heteroaryl;

$U^1$-$U^4$ are independently N or $CR^a$, wherein $U^1$-$U^4$ are not each N;

V is a bond, N or $CR^c$;

W and Z are independently N or $CR^1$;

X is —CO—, —CON($R^{10}$)—, —CON($R^{10}$)($CH_2)_n$—, —($CH_2)_n$CON($R^{10}$)—, —($CH_2)_n$CON($R^{10}$)($CH_2)_n$—, —SON($R^{10}$)—, —SON($R^{10}$)($CH_2)_n$—, —$SO_2$N($R^{10}$)—, —$SO_2$N($R^{10}$)($CH_2)_n$—, —N($R^{10}$)C(=O)N($R^{10}$)—, —N($R^{10}$)CO—, —N($R^{10}$)CO($CH_2)_n$—, or —N($R^{10}$)CO($CH_2)_n$—, —($CH_2)_n$N($R^{10}$)—, —C=N—; or

Ar and X together form

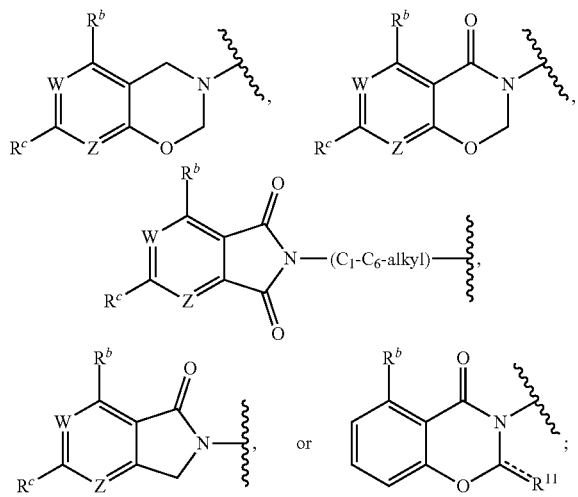

Y is a bond, N or CR$^2$;
R$^1$ is H, halogen, O—(C$_1$-C$_6$-alkyl), O—(C$_2$-C$_6$-alkyl)N(R$^{10}$)$_2$;
R$^2$ is H, C$_1$-C$_6$-alkyl, C$_1$-C$_6$-haloalkyl, O—(C$_1$-C$_6$-alkyl), O—(C$_1$-C$_6$-haloalkyl), halogen, CN, or NO$_2$;
R$^3$ is cycloalkylamino, optionally containing a heteroatom selected from N(R$^{10}$), O and S;
R$^{10}$ is independently H, —(C$_1$-C$_4$-alkyl), —(C$_1$-C$_4$-haloalkyl), —(C$_3$-C$_8$-cycloalkyl), —(C$_3$-C$_8$-heterocycloalkyl), aryl or heteroaryl;
⎓⎓⎓ is a double bond and R$^{11}$ is O, or
⎓⎓⎓ is a single bond and R$^{11}$ is —(C$_1$-C$_6$-alkyl), —(C$_1$-C$_6$-alkyl)-N(R$^{10}$)$_2$, or —(C$_1$-C$_6$-alkyl)-N(R$^{10}$)$_3$$^+$halogen$^-$; and
each n is independently an integer from 1-4, or a pharmaceutically acceptable salt thereof.

In some embodiments, the HAT activator is a compound of formula (I),

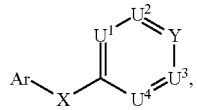

wherein,
Ar is

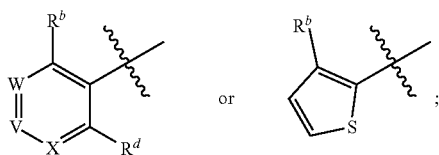

R$^a$ is H, C$_1$-C$_6$-alkyl, C$_1$-C$_6$-haloalkyl, O—(C$_1$-C$_6$-alkyl), O—(C$_1$-C$_6$-haloalkyl), halogen, CN, or NO$_2$;
R$^b$ is H, OH, C$_1$-C$_6$-alkyl, —(C$_1$-C$_6$-alkyl)CO$_2$—(C$_1$-C$_6$-alkyl), C$_1$-C$_6$-haloalkyl, C$_2$-C$_6$-alkenyl, C$_3$-C$_8$-cycloalkyl, C$_2$-C$_6$-heteroalkyl, C$_3$-C$_8$-heterocycloalkyl, aryl, heteroaryl, O—(C$_1$-C$_6$-alkyl), O—(C$_1$-C$_6$-alkyl)CO$_2$—(C$_1$-C$_6$-alkyl), O—(C$_1$-C$_6$-haloalkyl), O—(C$_3$-C$_8$-cycloalkyl), O—(C$_2$-C$_6$-alkenyl), O—(C$_3$-C$_8$-heterocycloalkyl), N(R$^{10}$)—(C$_1$-C$_6$-alkyl), N(R$^{10}$)—(C$_1$-C$_6$-alkyl)CO$_2$—(C$_1$-C$_6$-alkyl), N(R$^{10}$)—(C$_3$-C$_8$-cycloalkyl), SH, S—(C$_1$-C$_6$-alkyl), S—(C$_1$-C$_6$-alkyl)CO$_2$—(C$_1$-C$_6$-alkyl), SO$_2$—(C$_1$-C$_6$-alkyl), SO$_2$—(C$_1$-C$_6$-alkyl)CO$_2$—(C$_1$-C$_6$-alkyl), O—(C$_2$-C$_6$-alkyl)-N(R$^{10}$)$_2$, O—(C$_2$-C$_6$-alkyl)-N(R$^{10}$)$_3$$^+$halogen$^-$, O—(C$_3$-C$_8$-cycloalkyl)-N(R$^{10}$)$_2$, N(R$^{10}$)—(C$_2$-C$_6$-alkyl)-N(R$^{10}$)$_2$, —(C$_1$-C$_6$-alkyl)-N(R$^{10}$)$_2$, —(C$_1$-C$_6$-alkyl)-R$^3$, O—(C$_1$-C$_6$-alkyl)-R$^3$, O—(C$_3$-C$_8$-cycloalkyl)-R$^3$, N(R$^{10}$)—(C$_1$-C$_6$-alkyl)-R$^3$, O-aryl, or O-heteroaryl;
R$^c$ is H, —(C$_1$-C$_6$-alkyl), O—(C$_1$-C$_6$-alkyl), C(=O)NH-phenyl, wherein phenyl is substituted with one or more halo or haloalkyl;
R$^d$ is H, OH, C$_1$-C$_{16}$-alkyl, C$_1$-C$_6$-haloalkyl, O—(C$_3$-C$_8$-cycloalkyl), O—(C$_3$-C$_8$-heterocycloalkyl), O—(C$_2$-C$_6$-alkenyl), O—(C$_1$-C$_6$-alkyl), O—(C$_1$-C$_6$-alkyl)-phenyl, O—(C$_2$-C$_6$-alkyl)-N(R$^{10}$)$_2$, O—(C$_2$-C$_6$-alkyl)-N(R$^{10}$)$_3$$^+$halogen$^-$, —(C$_1$-C$_6$-alkyl)-R$^3$, O—(C$_1$-C$_6$-alkyl)-R$^3$, O S(C$_1$-C$_6$-alkyl), N(R$^{10}$)—(C$_1$-C$_6$-alkyl)-R$^3$, —N(R$^{10}$)—(C$_1$-C$_6$-alkyl), —N(R$^{10}$)—(C$_2$-C$_6$-alkenyl), —N(R$^{10}$)—(C$_3$-C$_8$-cycloalkyl), —N(R$^{10}$)—(C$_3$-C$_8$-heterocycloalkyl), N(R$^{10}$)—(C$_2$-C$_6$-alkyl)-N(R$^{10}$)$_2$—(C$_1$-C$_6$-alkyl)-N(R$^{10}$)$_2$, S—(C$_2$-C$_6$-alkyl)-N(R$^{10}$)$_2$, OCH$_2$C(O)O(C$_1$-C$_6$-alkyl), O-aryl, N-aryl, O-heteroaryl, or N-heteroaryl;
U$^1$-U$^4$ are independently N or CR$^a$, wherein U$^1$-U$^4$ are not each N;
V is a bond, N or CR$^c$;
W and Z are independently N or CR$^1$;
X is —CO—, —CON(R$^{10}$)—, —CON(R$^{10}$)(CH$_2$)$_n$—, —(CH$_2$)$_n$CON(R$^{10}$)—, —(CH$_2$)$_n$CON(R$^{10}$)(CH$_2$)$_n$—, —SON(R$^{10}$)—, —SON(R$^{10}$)(CH$_2$)$_n$—, —SO$_2$N(R$^{10}$)—, —SO$_2$N(R$^{10}$)(CH$_2$)$_n$—, —N(R$^{10}$)C(=O)N(R$^{10}$)—, —N(R$^{10}$)CO—, —N(R$^{10}$)CO(CH$_2$)$_n$—, or —N(R$^{10}$)CO(CH$_2$)$_n$—, —(CH$_2$)$_n$N(R$^{10}$)—, —C=N—; or
Ar and X together form

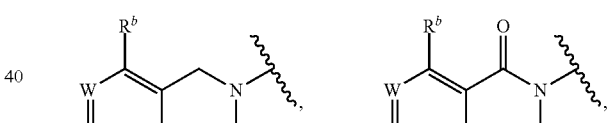
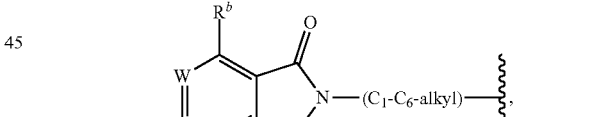
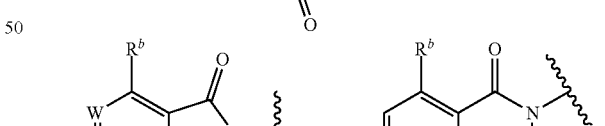

Y is a bond, N or CR$^2$;
R$^1$ is H, halogen, O—(C$_1$-C$_6$-alkyl), O—(C$_2$-C$_6$-alkyl)N(R$^{10}$)$_2$;
R$^2$ is H, C$_1$-C$_6$-alkyl, C$_1$-C$_6$-haloalkyl, O—(C$_1$-C$_6$-alkyl), O—(C$_1$-C$_6$-haloalkyl), halogen, CN, or NO$_2$;
R$^3$ is cycloalkylamino, optionally containing a heteroatom selected from N(R$^{10}$), O and S;
R$^{10}$ is independently H, —(C$_1$-C$_4$-alkyl), —(C$_1$-C$_4$-haloalkyl), —(C$_3$-C$_8$-cycloalkyl), —(C$_3$-C$_8$-heterocycloalkyl), aryl or heteroaryl;

═ is a double bond and R¹¹ is O, or
═ is a single bond and R¹¹ is —(C₁-C₆-alkyl), —(C₁-C₆-alkyl)-N(R¹⁰)₂, or —(C₁-C₆-alkyl)-N(R¹⁰)₃⁺halogen⁻; and each n is independently an integer from 1-4, or a pharmaceutically acceptable salt thereof.

In some embodiments, the compound of formula (I) is a compound of formula (Ia),

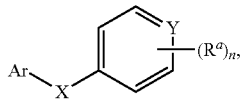

wherein,
Ar is

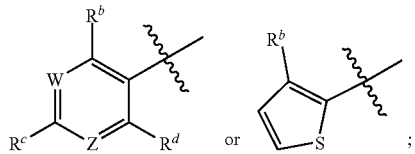

R$^a$ is H, C₁-C₆-alkyl, C₁-C₆-haloalkyl, O—(C₁-C₆-alkyl), O—(C₁-C₆-haloalkyl), halogen, CN, or NO₂;
R$^b$ is H, C₁-C₆-alkyl, C₂-C₆-alkenyl, C₃-C₈-cycloalkyl, C₂-C₆-heteroalkyl, C₃-C₈-heterocycloalkyl, aryl, heteroaryl, O—(C₁-C₆-alkyl), O—(C₃-C₈-cycloalkyl), O—(C₂-C₆-alkenyl), O—(C₃-C₈-heterocycloalkyl), N(R¹⁰)—(C₁-C₆-alkyl), N(R¹⁰)—(C₃-C₈-cycloalkyl), S—(C₁-C₆-alkyl), O—(C₂-C₆-alkyl)-N(R¹⁰)₂, O—(C₃-C₈-cycloalkyl)-N(R¹⁰)₂, N(R¹⁰)—(C₂-C₆-alkyl)-N(R¹⁰)₂, —(C₁-C₆-alkyl)-N(R¹⁰)₂, —(C₁-C₆-alkyl)-R³, O—(C₁-C₆-alkyl)-R³, O—(C₃-C₈-cycloalkyl)-R³, N(R¹⁰)—(C₁-C₆-alkyl)-R³, O-aryl, or O-heteroaryl;
R$^c$ is H, —(C₁-C₆-alkyl), O—(C₁-C₆-alkyl), C(═O)NH-phenyl, wherein phenyl is substituted with one or more halo or haloalkyl;
R$^d$ is H, OH, —(C₁-C₆-alkyl), O—(C₃-C₈-cycloalkyl), O—(C₃-C₈-heterocycloalkyl), O—(C₂-C₆-alkenyl), O—(C₁-C₆-alkyl), O—(C₂-C₆-alkyl)-N(R¹⁰)₂, —(C₁-C₆-alkyl)-R³, O—(C₁-C₆-alkyl)-R³, N(R¹⁰)—(C₁-C₆-alkyl)-R³, —N(R¹⁰)—(C₁-C₆-alkyl), —N(R¹⁰)—(C₂-C₆-alkenyl), —N(R¹⁰)—(C₃-C₈-cycloalkyl), —N(R¹⁰)—(C₃-C₈-heterocycloalkyl), N(R¹⁰)—(C₂-C₆-alkyl)-N(R¹⁰)₂, —(C₁-C₆-alkyl)-N(R¹⁰)₂, S—(C₂-C₆-alkyl)-N(R¹⁰)₂, OCH₂C(O)O-alkyl, O-aryl, N-aryl, O-heteroaryl, or N-heteroaryl;
W and Z are independently N or CR¹;
X is —CO—, —CON(R¹⁰)—, —CON(R¹⁰)(CH₂)$_n$—, —(CH₂)$_n$CON(R¹⁰)—, —(CH₂)$_n$CON(R¹⁰)(CH₂)$_n$—, —SON(R¹⁰)—, —SON(R¹⁰)(CH₂)$_n$—, —SO₂N(R¹⁰)—, —SO₂N(R¹⁰)(CH₂)$_n$—, —N(R¹⁰)C(═O)N(R¹⁰)—, —N(R¹⁰)CO—, —N(R¹⁰)CO(CH₂)$_n$—, or —N(R¹⁰)CO(CH₂)$_n$—, —(CH₂)$_n$N(R¹⁰)—, —C═N—; or
Ar and X together form

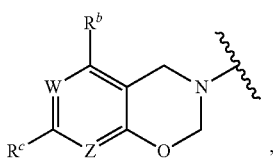

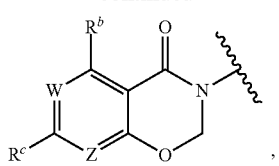

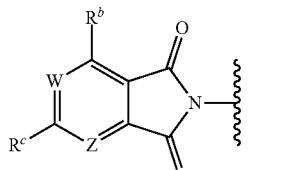, or

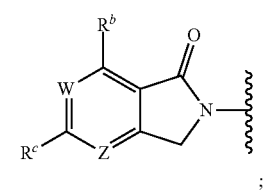;

Y is N or CR²;
R¹ is H, halogen, O—(C₁-C₆-alkyl), O—(C₂-C₆-alkyl)N(R¹⁰)₂;
R² is H, C₁-C₆-alkyl, C₁-C₆-haloalkyl, O—(C₁-C₆-alkyl), O—(C₁-C₆-haloalkyl), halogen, CN, or NO₂;
R³ is cycloalkylamino, optionally containing a heteroatom selected from N(R¹⁰), O and S;
R¹⁰ is independently H, —(C₁-C₄-alkyl), —(C₁-C₄-haloalkyl), —(C₃-C₈-cycloalkyl), —(C₃-C₅-heterocycloalkyl), aryl or heteroaryl; and
each n is independently an integer from 1-3.

In some embodiments, the compound of formula (I) is

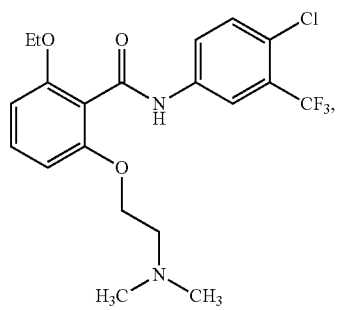

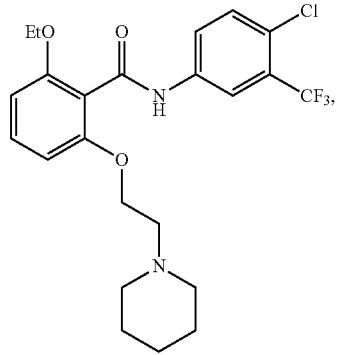

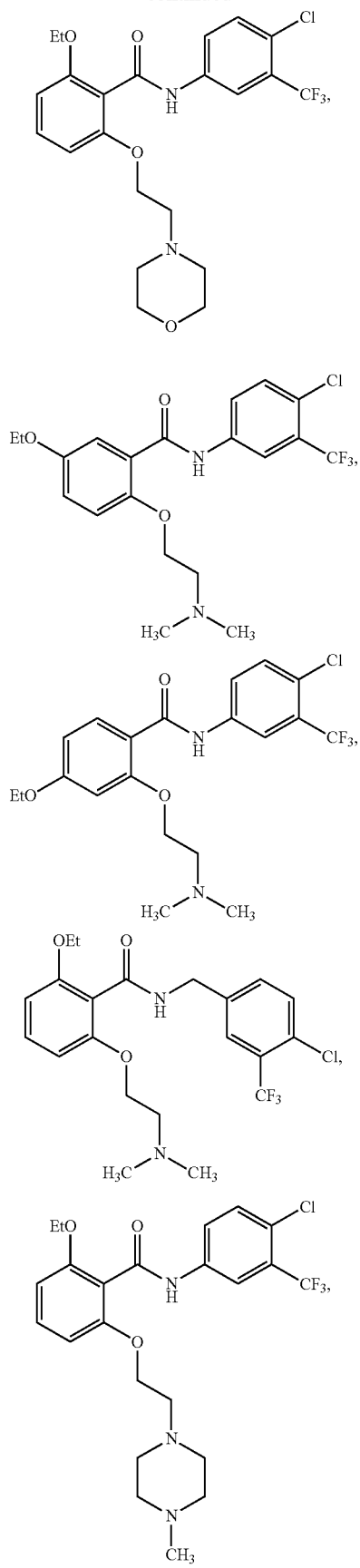
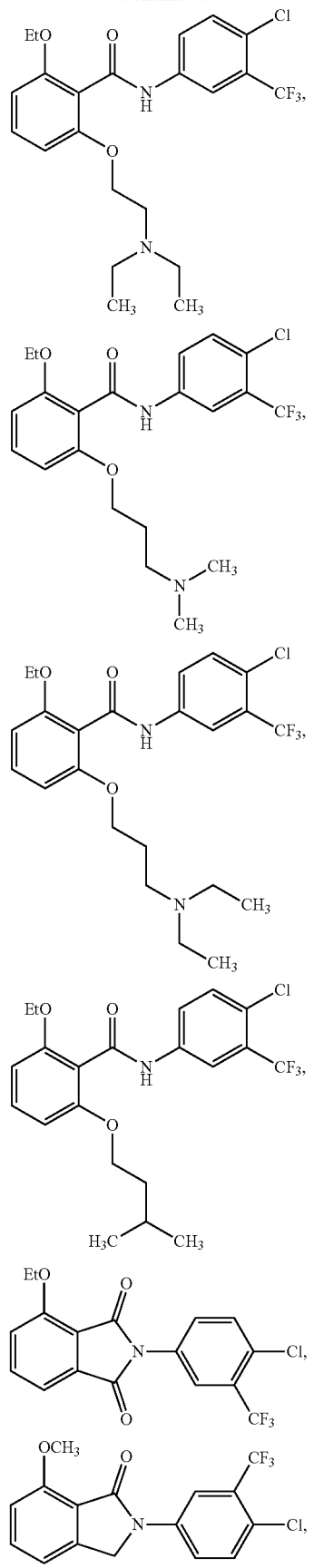

53
-continued
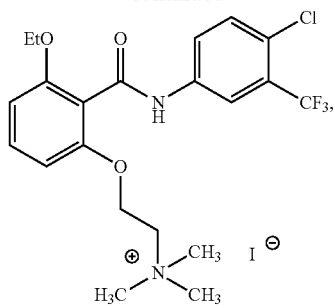
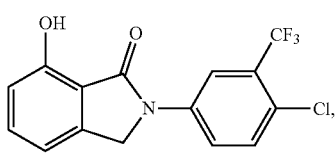
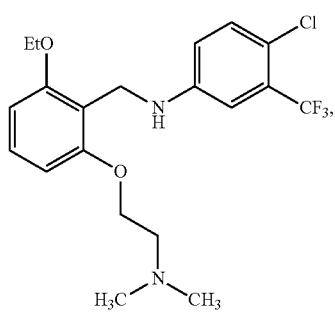
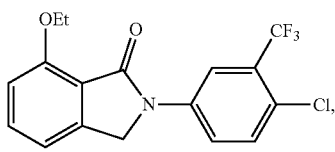
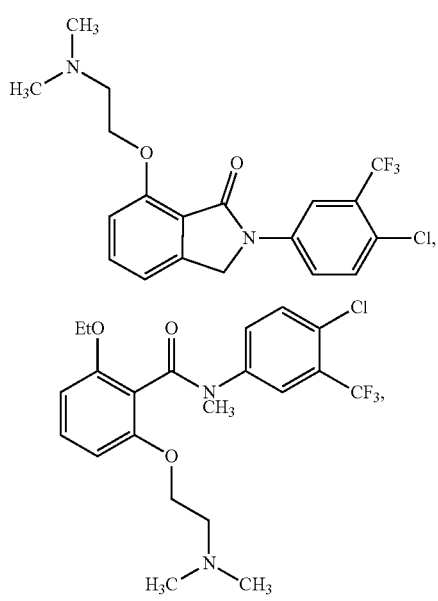
54
-continued
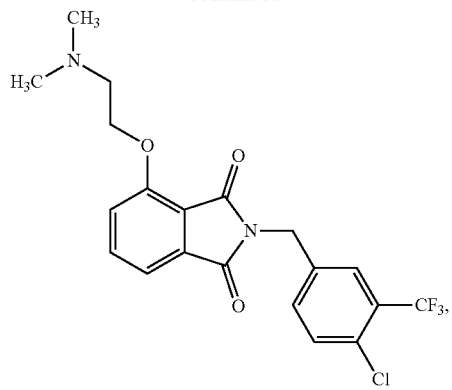
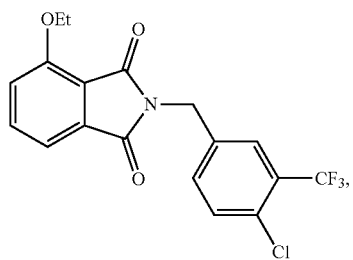
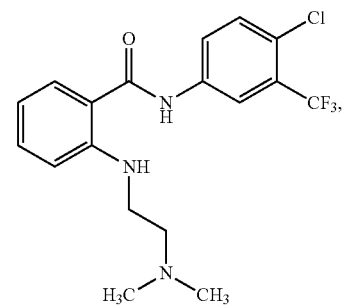
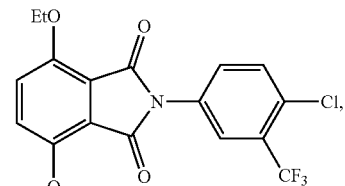
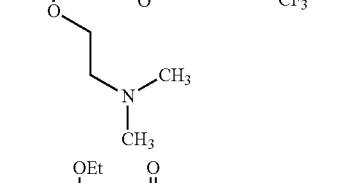
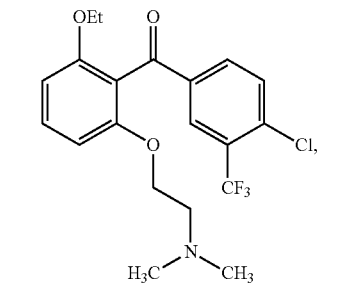

55
-continued
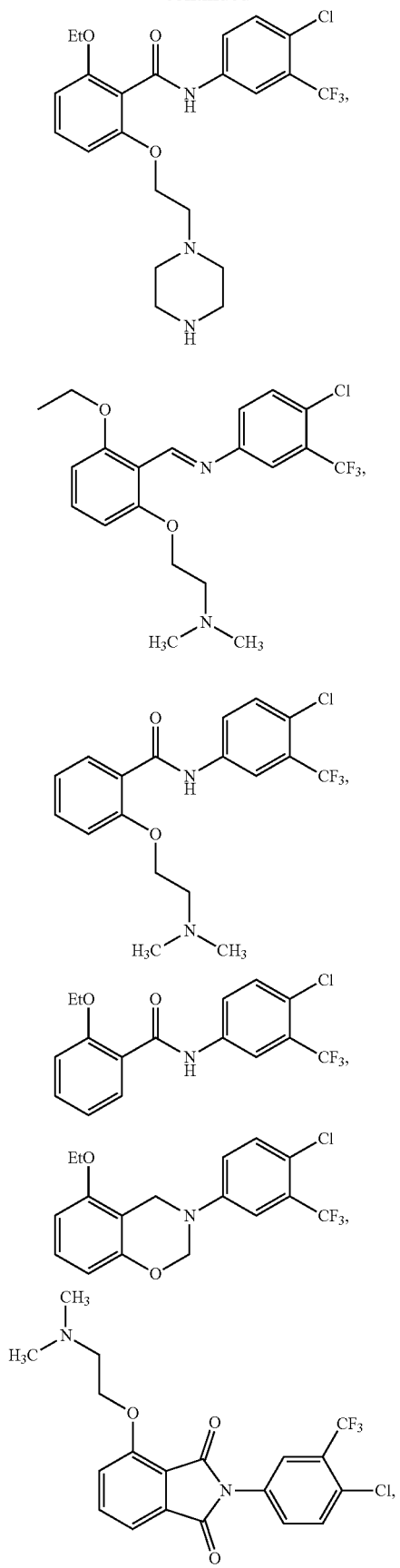
56
-continued
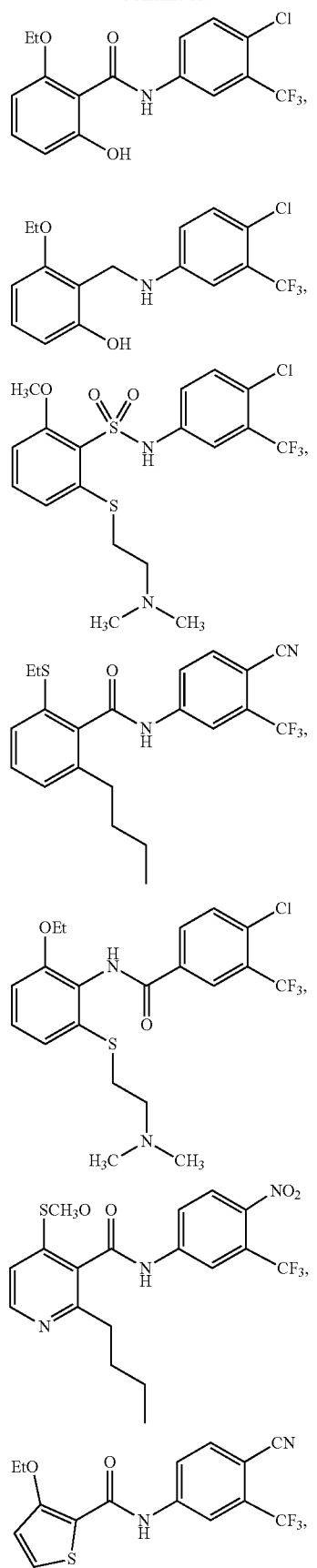

57
-continued
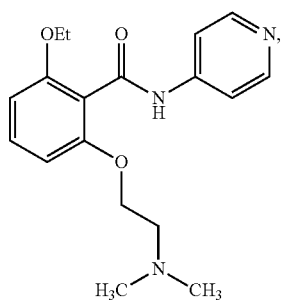
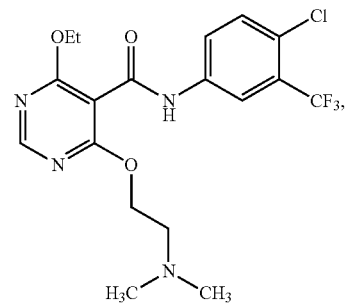
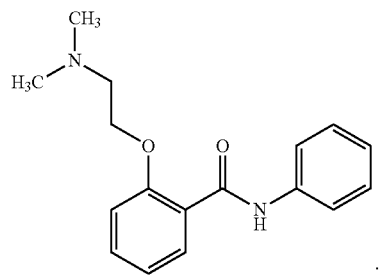
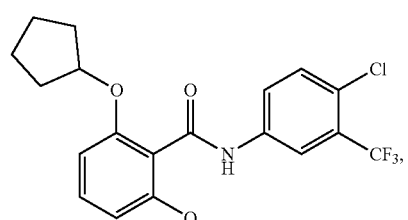
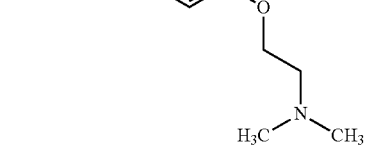
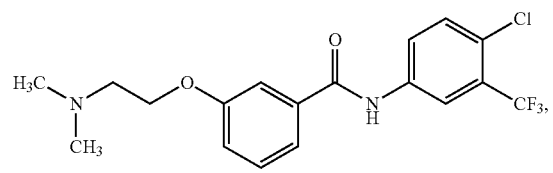
58
-continued
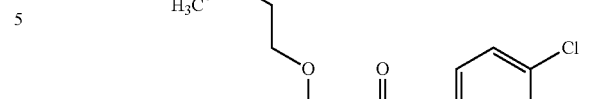
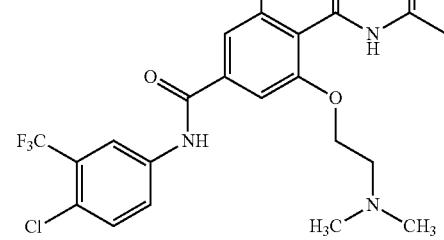
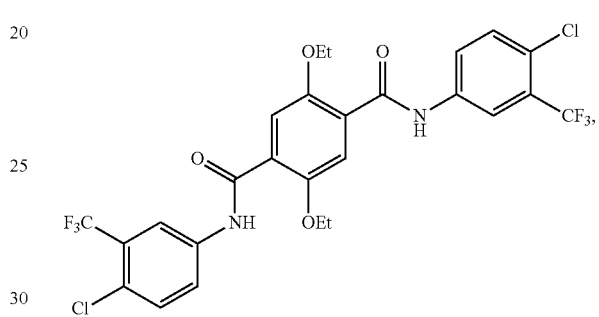
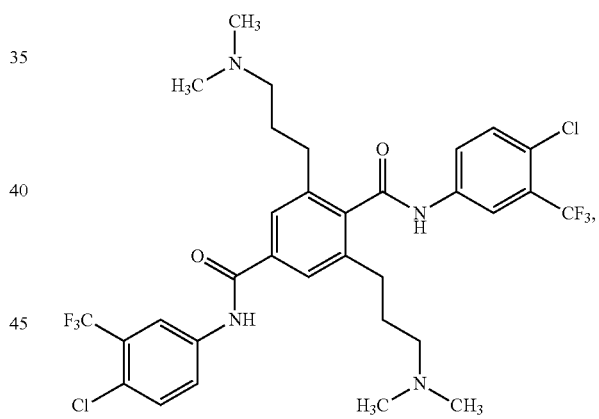
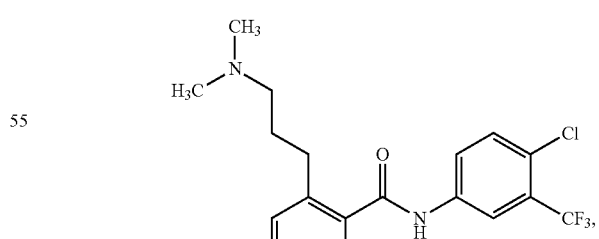
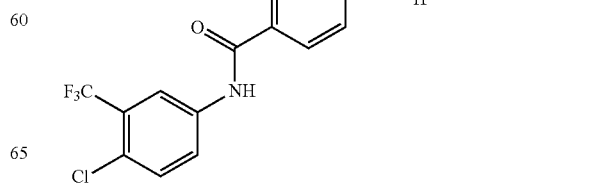

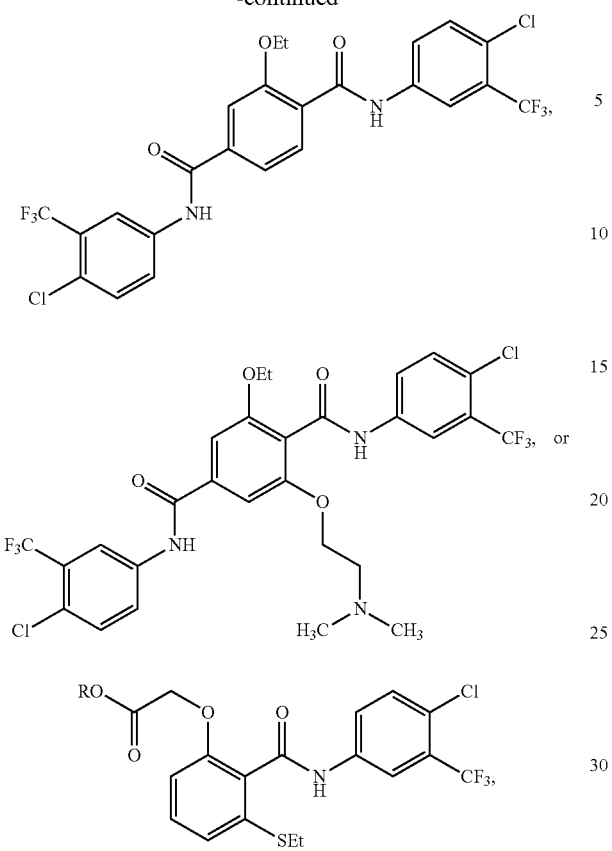
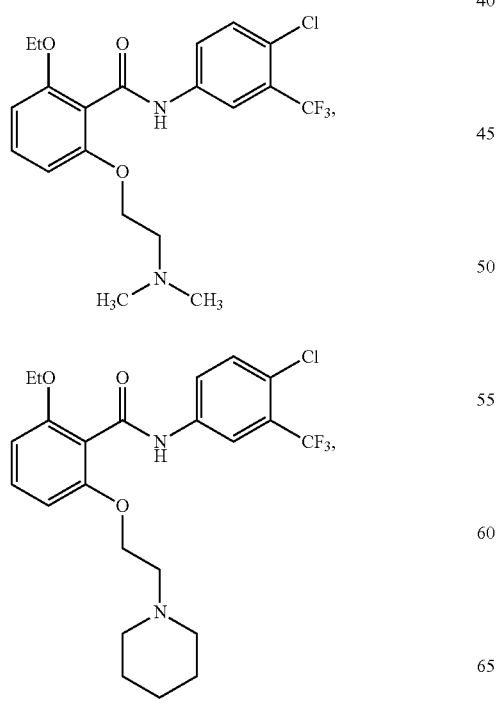
wherein R is H, Methyl, Ethyl, n-Propyl, Isopropyl, n-butyl, t-butyl, $C_8H_{18}$, $C_{15}H_{26}$, $C_{15}H_{28}$, $C_{15}H_{30}$, or $C_{15}H_{32}$.
In some embodiments, the compound of formula (I) is
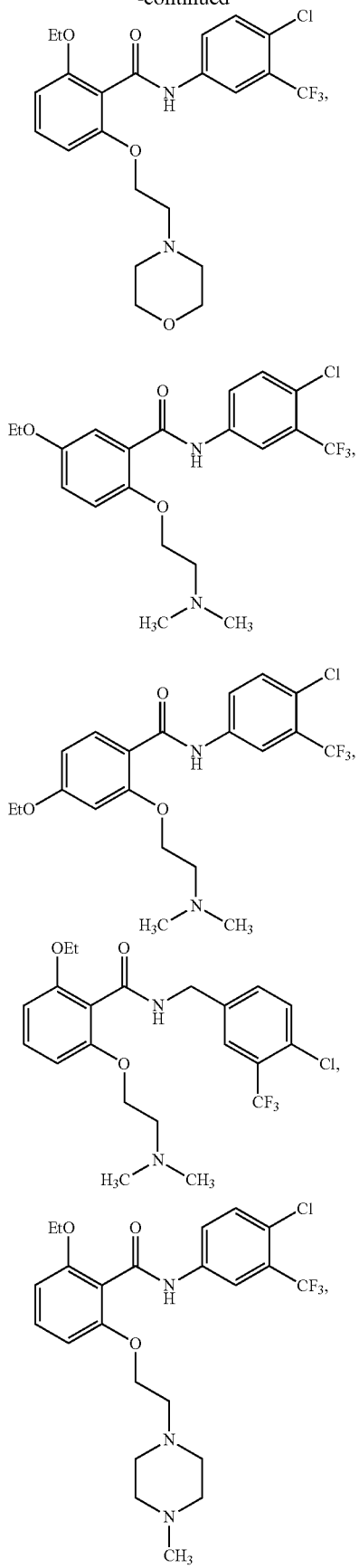

-continued
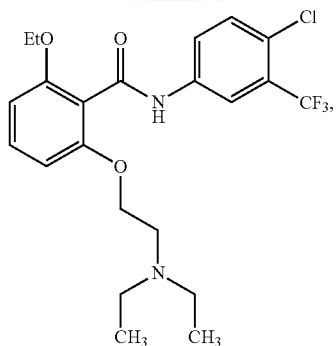
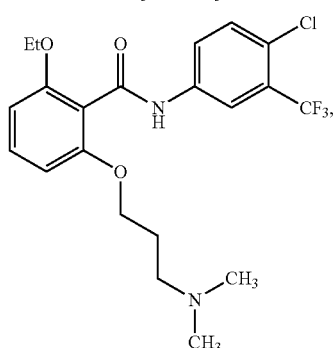
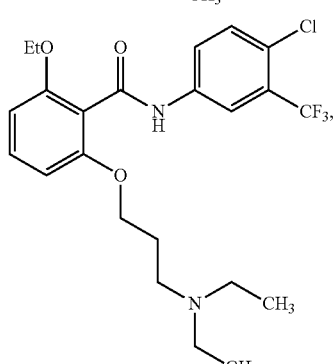
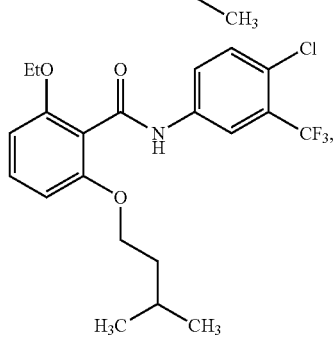
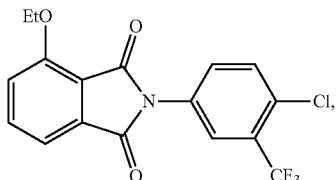
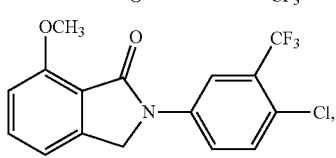
-continued
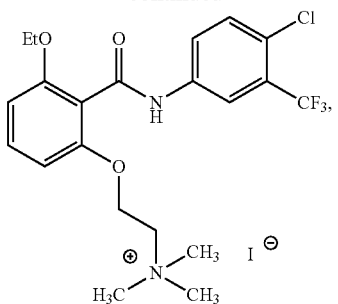
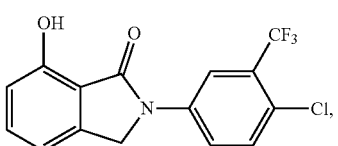
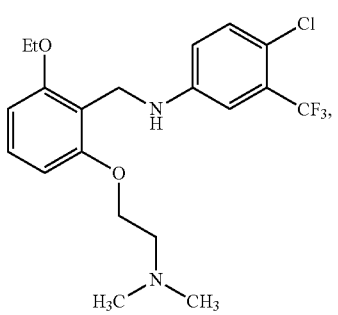
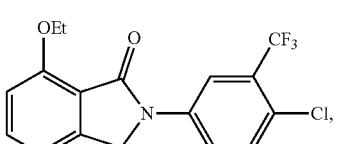
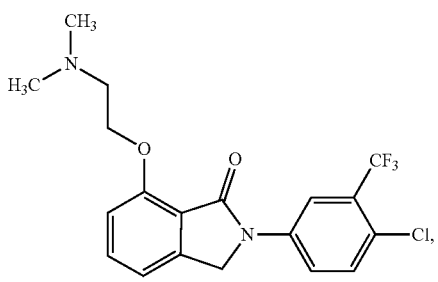
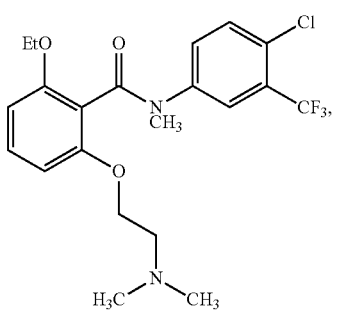

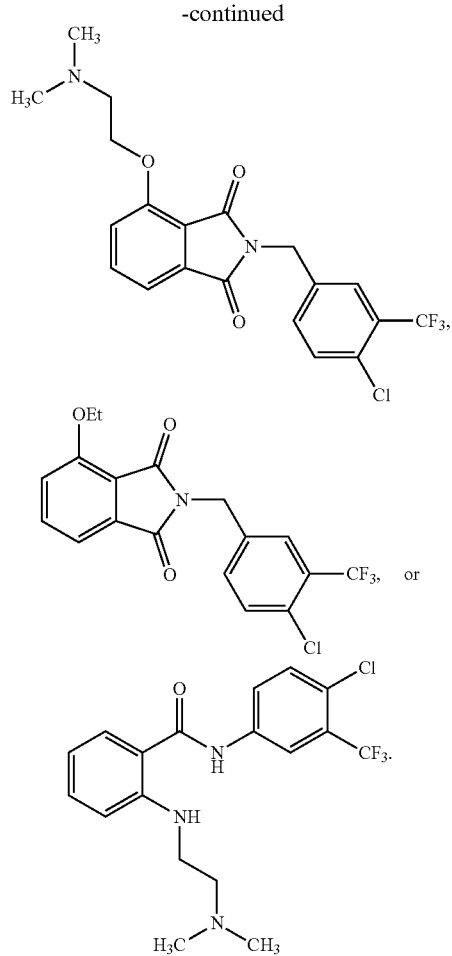
In some embodiments, the compound of formula (I) is
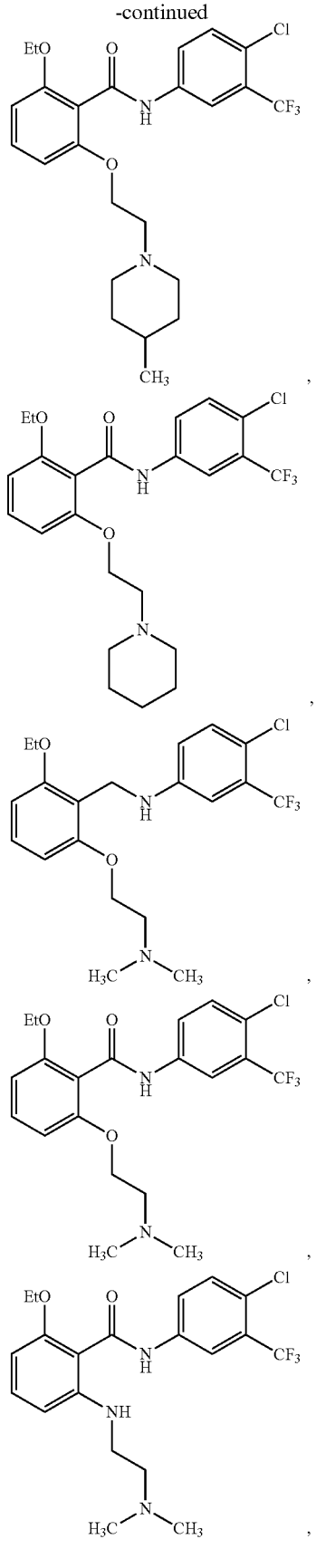
or a pharmaceutically acceptable salt thereof.

In some embodiments, the compound of formula (I) is

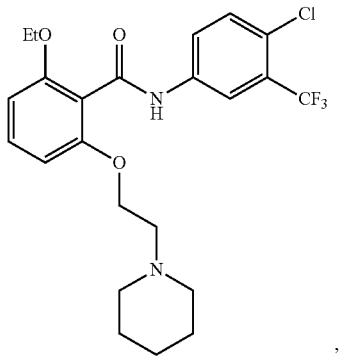 [SMILES: CCOc1cccc(OCCN2CCCCC2)c1C(=O)Nc1ccc(Cl)c(C(F)(F)F)c1]

or a pharmaceutically acceptable salt thereof.

In some embodiments, the compound of formula (I) is

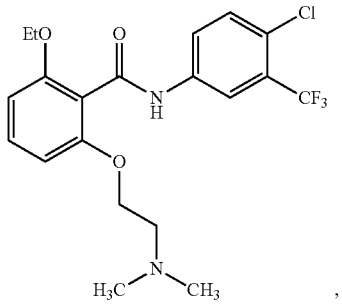 [SMILES: CCOc1cccc(OCCN(C)C)c1C(=O)Nc1ccc(Cl)c(C(F)(F)F)c1]

or a pharmaceutically acceptable salt thereof.

Exemplary methods of preparation of compounds of formula (I) are shown in Scheme A.

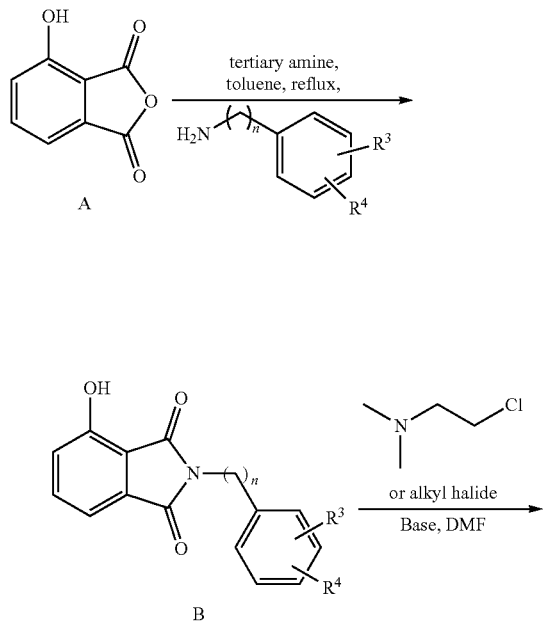

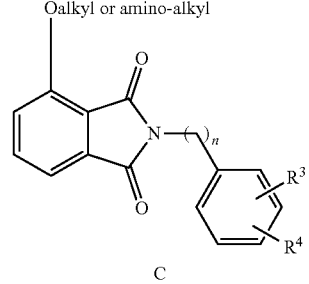

Compound A can be treated with a primary amine in the presence of a tertiary amine in a solvent such as toluene and heated to obtain compounds B. Compounds B can be alkylated using an alkyl halide or aminoalkyl halide in the presence of a base such as potassium carbonate in a solvent such as N,N-dimethylformamide to obtain compounds C. In the case of compounds C that contain amino-alkyl groups, treatment with methyl iodide can be performed to obtain the methylamino salt.

Further exemplary methods of preparation of compounds of formula (I) are shown in Scheme B.

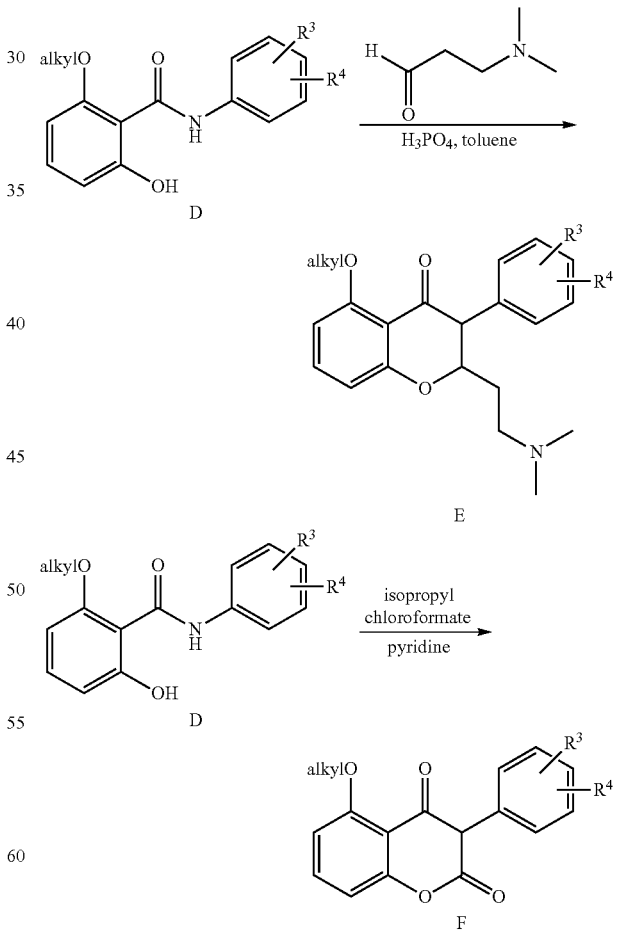

Compounds D can be treated with an amino-aldehyde in the presence of an acid such as phosphoric acid in a solvent such as toluene to obtain compounds E. Alternatively, compounds D can be treated with a formate source such as isopropyl chloroformate or triphosgene in a solvent such as pyridine to obtain compounds F.

Pharmaceutically acceptable salts are known in the art, and can be selected from those listed in Berge, et al. ["Pharmaceutical Salts," *J. Pharm. Sci.,* 66(1):1-19 (January 1977); herein incorporated by reference in its entirety]. In some embodiments, a pharmaceutically acceptable salt of a compound of formula (I) is an acid addition salt, for example a hydrohalide (such as hydrochloride or hydrobromide), sulfate, or phosphate salt. In some embodiments, a pharmaceutically acceptable salt of a compound of formula (I) is a base addition salt, for example a sodium, potassium, calcium, or ammonium salt. In some embodiments, the base addition salt is a tetrafluoroboro salt.

In some embodiments, the invention provides methods for reducing inclusion bodies (e.g., amyloid beta (Aβ) protein deposits, native and phosphorylated Tau proteins, native and phosphorylated alpha-synuclein, lipofuscin, cleaved TAR-DBP (TDB-43), or a combination thereof) in a subject afflicted with a neurodegenerative disease (e.g., a AD, Huntington's Disease, or Parkinson's Disease) by administering any one of the HAT modulator compounds having formula (I) and a HDAC modulator. In some embodiments, the invention provides methods for treating a neurodegenerative disease in a subject by administering any one of the HAT modulator compounds having formula (I) and a HDAC modulator. In some embodiments, the invention further provides methods for treating cancer in a subject by administering any one of the HAT modulator compounds having formula (I) and a HDAC modulator. In some embodiments, the compound administered to a subject is any one of the compounds of formula (I) and a HDAC modulator. In some embodiments, the compound of formula (I) is any of compounds

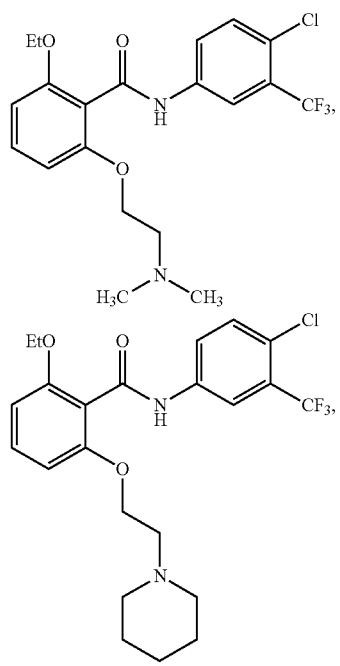

-continued

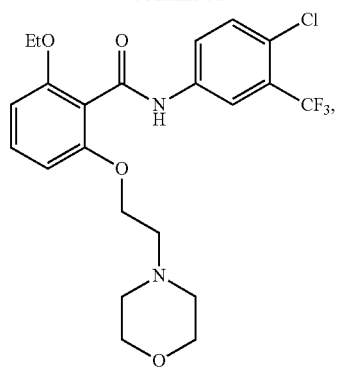

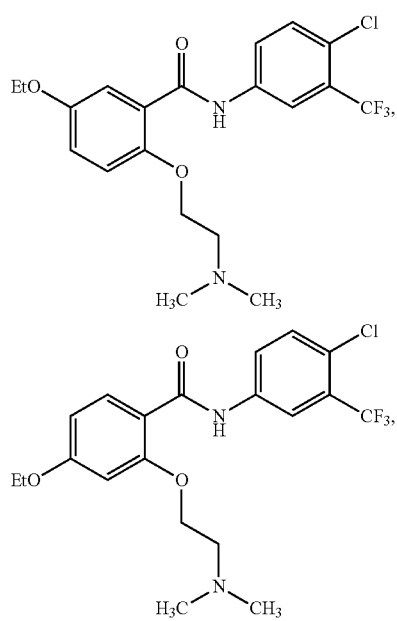

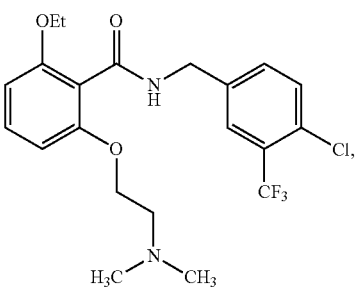

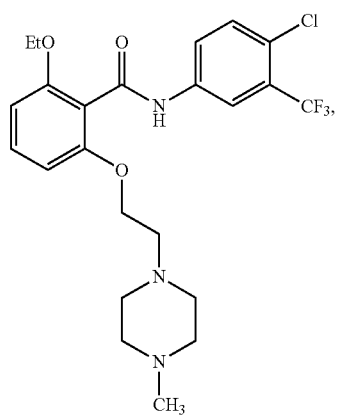

69
-continued
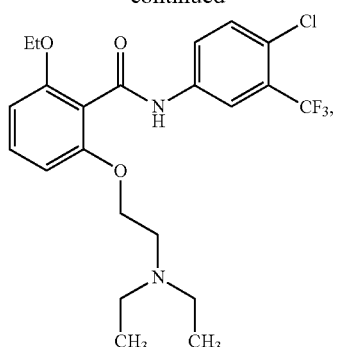
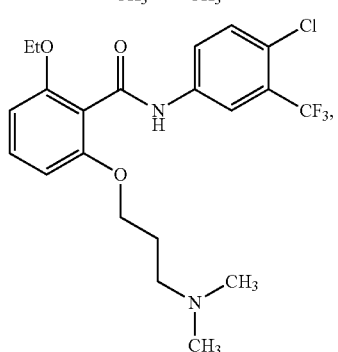
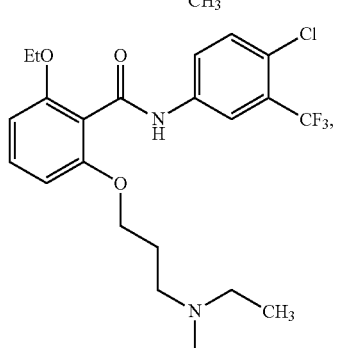
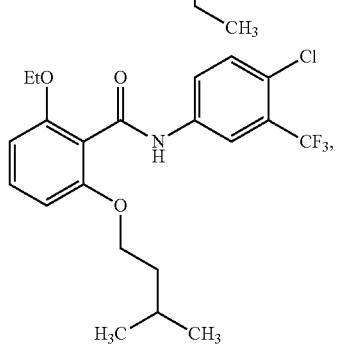
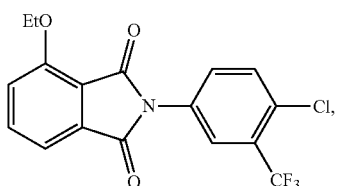
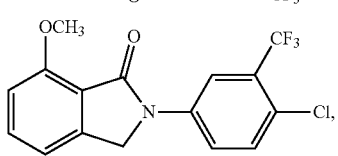
70
-continued
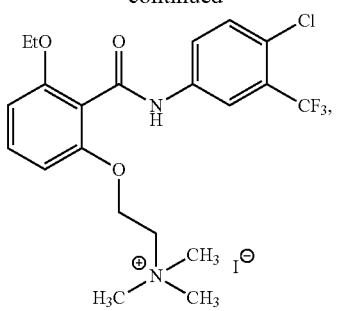
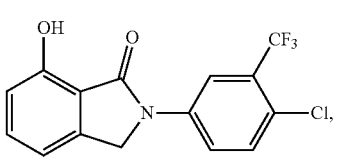
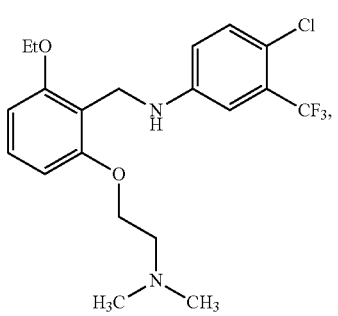
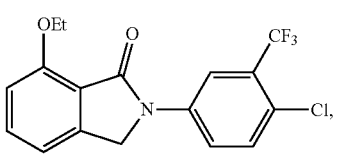
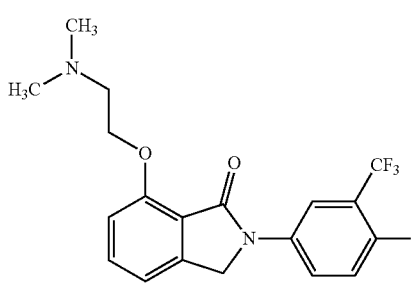
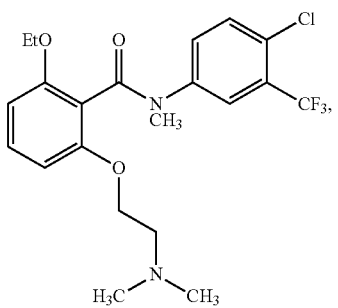

-continued

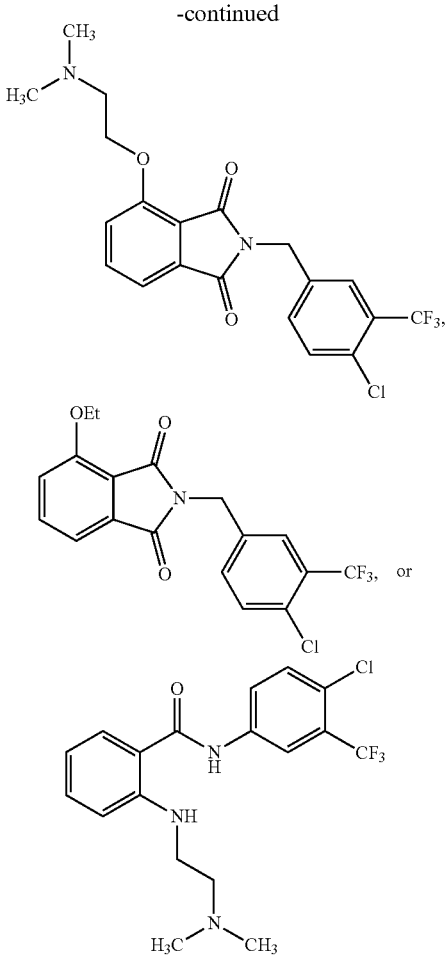

and a HDAC modulator. In some embodiments, the HDAC modulator is a HDAC inhibitor.

In some embodiments, the methods comprise administering to the subject a therapeutic amount of a HAT modulator compound and therapeutic amount a HDAC modulator compound. In some embodiments, the subject exhibits abnormally elevated amyloid beta plaques, or elevated Tau protein levels, or accumulations of alpha-synuclein, or accumulations of lipofuscin, or accumulation of cleaved TAR-DBP (TDB-43) levels, or a combination thereof. In some embodiments, the Aβ protein deposit comprises an $Aβ_{40}$ isomer, an $Aβ_{42}$ isomer, or a combination thereof. In a further embodiment, the subject is afflicted with Alzheimer's disease, Lewy body dementia, inclusion body myositis, Huntington's Disease, Parkinson's Disease, or cerebral amyloid angiopathy. In some embodiments, the subject is afflicted with cancer. In further embodiments, the cancer is Hodgkin's lymphoma, non-Hodgkin's lymphoma, B cell lymphoma, T cell lymphoma, or follicular lymphoma. In some embodiments, the B cell lymphoma is diffuse large B-cell lymphoma. In some embodiments, the diffuse large B-cell lymphoma is a germinal center-derived diffuse large B cell lymphoma, an activated B-cell-derived (ABC) diffuse large B-cell lymphoma, or non-germinal center diffuse large B cell lymphoma.

The dosage administered can be a therapeutically effective amount of the composition sufficient to result in amelioration of symptoms of a neurodegenerative disease such as, but not limited to reducing inclusion bodies (e.g., amyloid beta (Aβ) protein deposits, native and phosphorylated Tau proteins, native and phosphorylated alpha-synuclein, lipofuscin, cleaved TARDBP (TDB-43), or a combination thereof), or reducing memory loss in a subject. For example, observing at least, about a 25% reduction, at least about a 30% reduction, at least about a 40% reduction, at least about a 50% reduction, at least about a 60% reduction, at least about a 70% reduction, at least about a 80% reduction, at least about a 85% reduction, at least about a 90% reduction, at least about a 95% reduction, at least about a 97% reduction, at least about a 98% reduction, or a 100% reduction in inclusion bodies or memory loss in a subject is indicative of amelioration of symptoms of a neurodegenerative disease (for example, including, but not limited to, AD, Huntington's Disease, Parkinson's Disease). This efficacy in reducing inclusion occurrence can be, for example, a measure of ameliorating symptoms of a neurodegenerative disease.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A HAT modulator compound and a HDAC modulator compound can be administered to the subject one time (e.g., as a single injection or deposition). Alternatively, a HAT modulator compound and a HDAC modulator compound can be administered once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

In some embodiments, a HAT modulator compound and a HDAC modulator compound are used, formulated for use and/or administered to the subject. In some embodiments, the HAT modulator compound and the HDAC modulator are used, formulated for use and/or administered to the subject at the same time, optionally as a composition comprising the HAT modulator compound and the HDAC modulator, or as two separate doses. In some embodiments, the HAT modulator compound and the HDAC modulator are used, formulated for use and/or administered to the subject at different times. For example, some embodiments, the HAT modulator compound is used or administered prior to, or after the HDAC modulator. In one embodiment, the HAT modulator is used or administered prior to, or after the HDAC modulator separated by a time of at least about 1 minute, 2 minutes, 5 minutes, 10 minutes, 30 minutes: 45 minutes, 1 hour, 1.5 hours, 2 hours, 3 hours, 4 hours, 5 hours, 6 hours, 8 hours, 10 hours, 12 hours 16 hours, or 24 hours. Optionally, in some embodiments the HDAC modulator issued, formulated for use and/or administered to the subject separated by more than about 24 hours, 36 hours, 48 hours, 3 days, 4 days, 5 days, 6 days, or one week.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can also be used.

A therapeutically effective dose of a HAT modulator compound and a HDAC modulator compound can depend upon a number of factors known to those of ordinary skill in the art. The dose(s) of a HAT modulator compound and a HDAC modulator compound, can vary, for example, depending upon the identity, size, and condition of the subject or sample being treated, further depending upon the route by which the compounds are to be administered, if applicable, and the effect which the practitioner desires the HAT modulator compound and HDAC modulator compound to have. These amounts can be readily determined by a skilled artisan.

The HAT modulator compound and HDAC modulator compound of the invention can be incorporated into pharmaceutical compositions suitable for administration. Such compositions can comprise a HAT modulator compound (e.g., a compound of formula (I), or any of

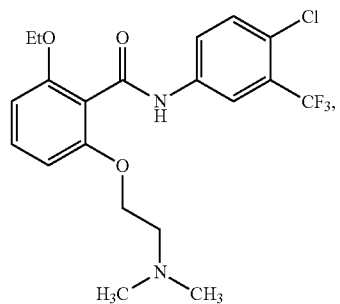

-continued

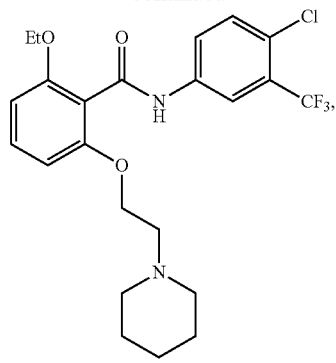

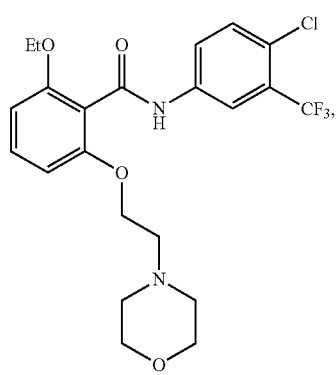

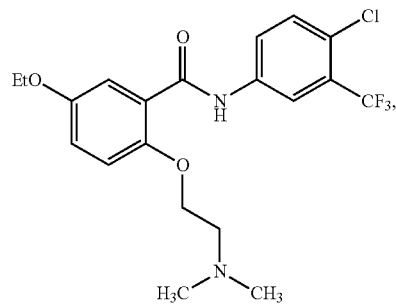

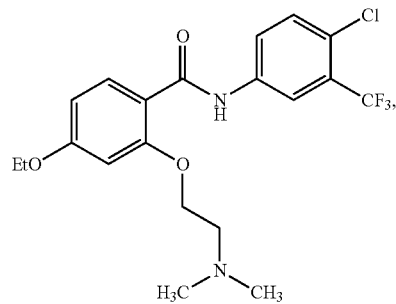

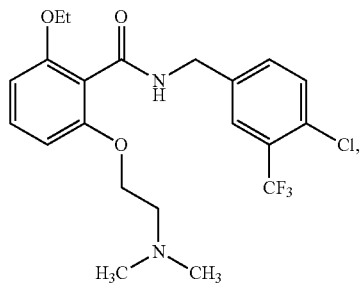

75
-continued
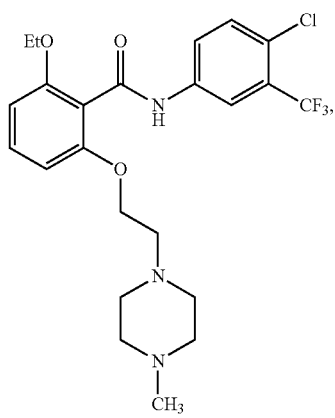
76
-continued
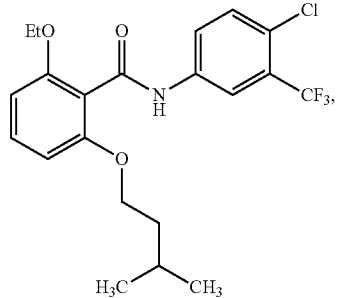
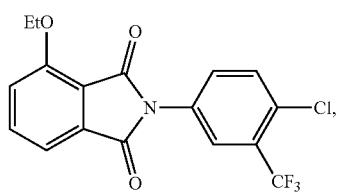
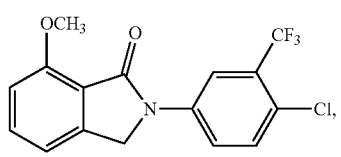
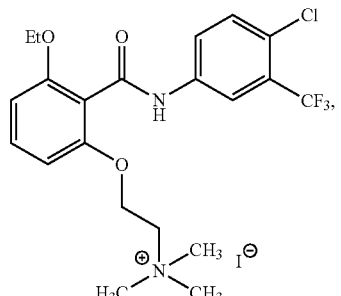
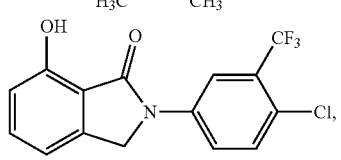
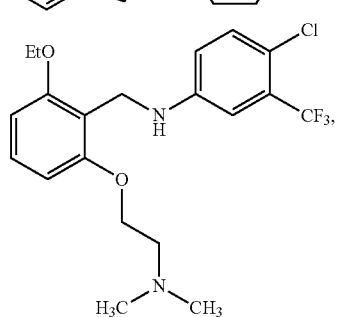
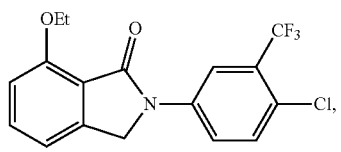

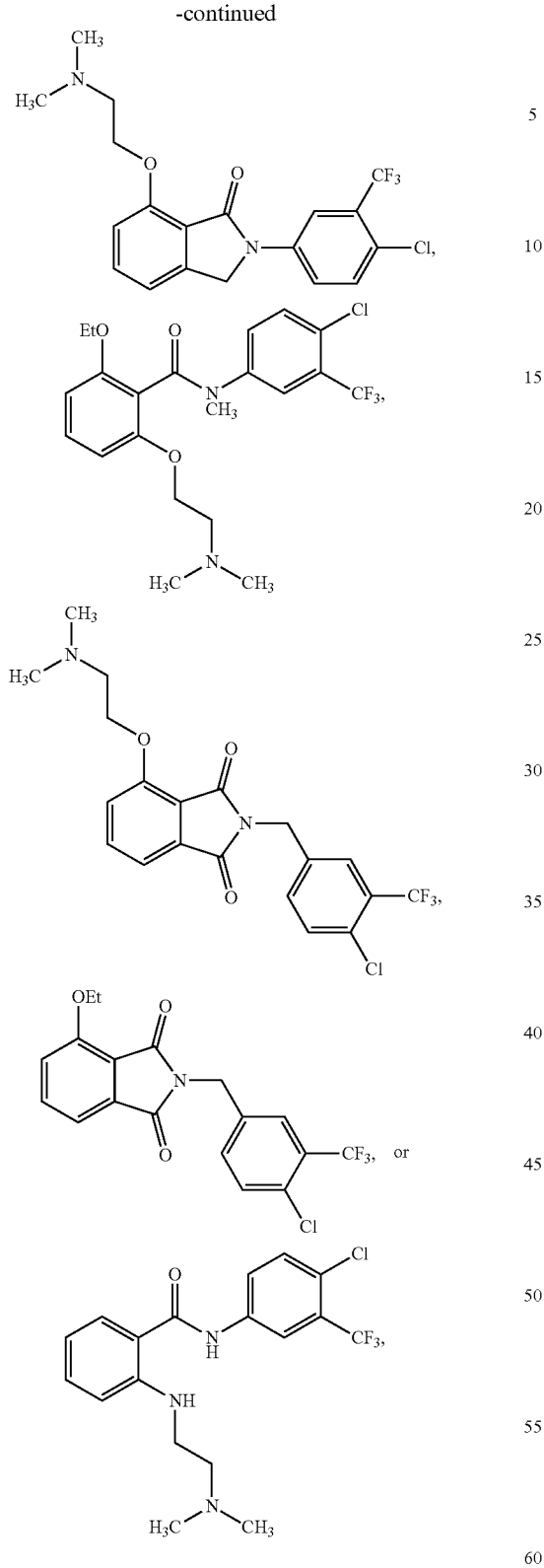
or any combination thereof), and a pharmaceutically acceptable carrier. Other compositions can comprise a HDAC modulator compounds (e.g. romidepsin, or vorinostat) and a pharmaceutically acceptable carrier. Other compositions can comprise a HAT modulator compound (e.g., a compound of formula (I), or any of -continued
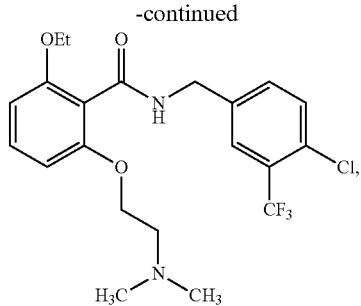
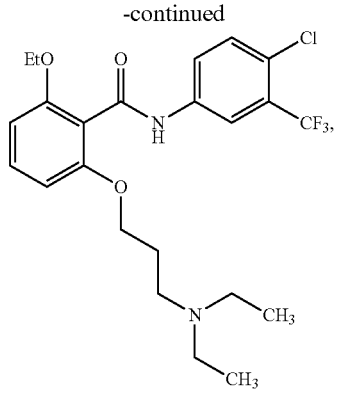
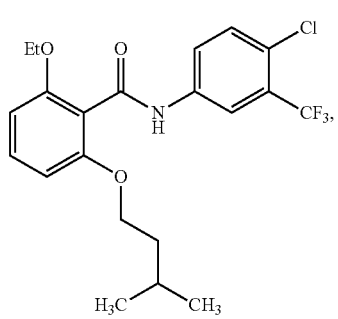
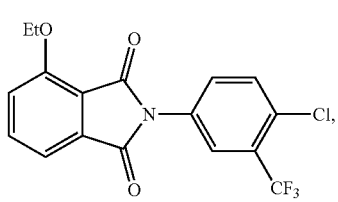
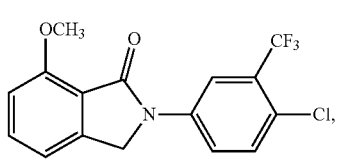
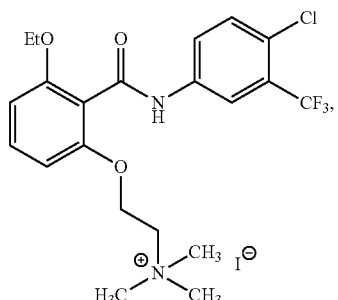
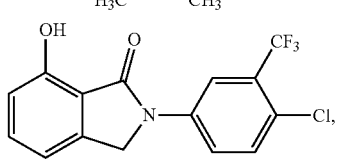

-continued

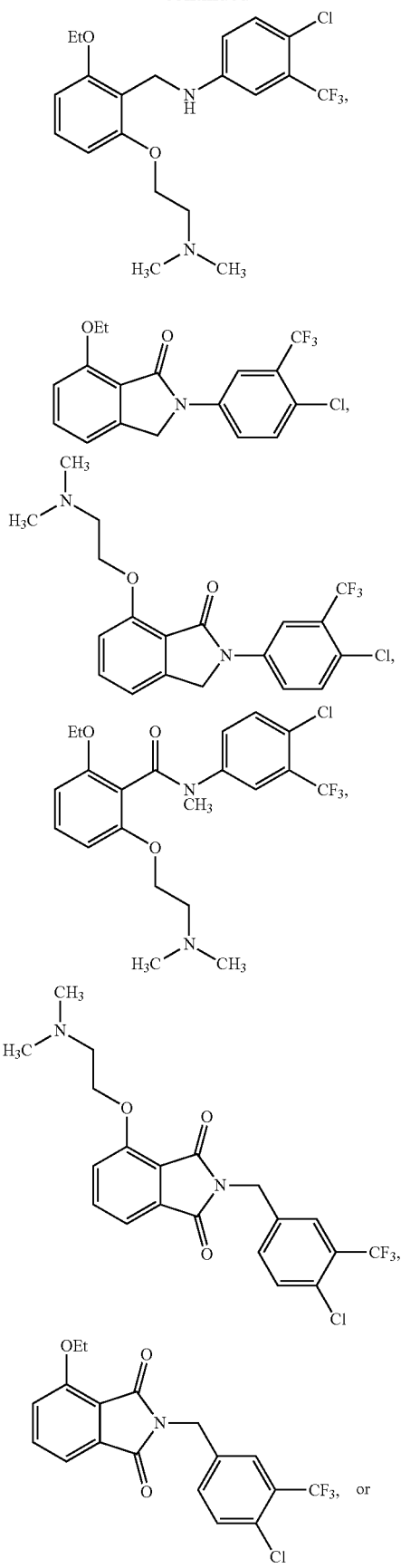

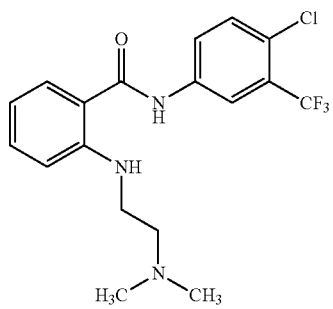

or any combination thereof), one or more HDAC modulator compounds (e.g. romidepsin, or vorinostat) and a pharmaceutically acceptable carrier. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

In one embodiment, the present disclosure relates to a pharmaceutical combination of romidepsin and

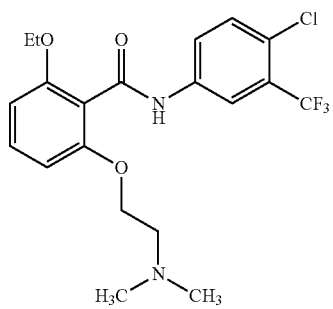 [SMILES: CCOc1cccc(OCCN(C)C)c1C(=O)Nc1ccc(Cl)c(C(F)(F)F)c1]

(YF2) or a pharmaceutically acceptable salt thereof. In another embodiment, the present disclosure relates to a pharmaceutical combination of romidepsin and

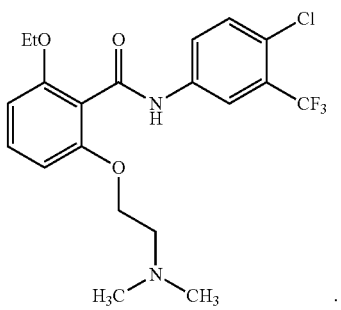 [SMILES: CCOc1cccc(OCCN(C)C)c1C(=O)Nc1ccc(Cl)c(C(F)(F)F)c1]

In one embodiment, the present disclosure relates to a pharmaceutical composition comprising romidepsin,

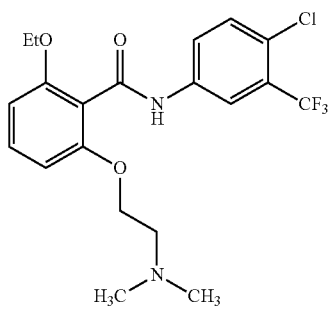 [SMILES: CCOc1cccc(OCCN(C)C)c1C(=O)Nc1ccc(Cl)c(C(F)(F)F)c1]

or a pharmaceutically acceptable salt thereof, and a pharmaceutically acceptable carrier or excipient. In another embodiment, the present disclosure relates to a pharmaceutical composition comprising romidepsin,

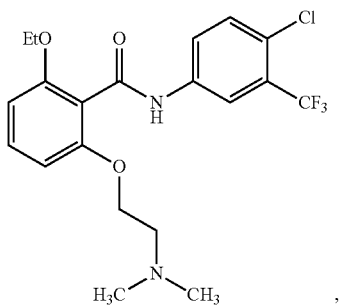 [SMILES: CCOc1cccc(OCCN(C)C)c1C(=O)Nc1ccc(Cl)c(C(F)(F)F)c1]

and a pharmaceutically acceptable carrier or excipient.

The present invention is based, in part, on the discovery that a HAT modulator alone, or in combination with a HDAC modulator, such as romidepsin, can treat cancer or neurodegenerative disease. Thus, in some embodiments, the present invention provides methods for treating cancer in a subject in need thereof with a HAT modulator alone or in combination with a HDAC modulator such as, for example, romidepsin. In other embodiments, the present invention provides methods for treating neurodegenerative disease in a subject in need thereof with a HAT modulator alone or in combination with a HDAC modulator such as, for example, romidepsin. When used in combination, the particular sequence of administration of HAT modulator and HDAC modulator is not important. Thus, in some embodiments, the HAT modulator and HDAC modulator may be administered at the same time. In some embodiments, the HAT modulator and HDAC modulator may be administered at different times. In some embodiments, the HAT modulator and HDAC modulator may be administered sequentially. In some embodiments, the HAT modulator is administered prior to administration of the HDAC modulator. In some embodiments, the HDAC modulator is administered prior to the administration of the HAT modulator. In some embodiments, the subject is currently taking a HDAC modulator, such as romidepsin, and a HAT modulator is administered while the subject maintains treatment with the HDAC modulator. In some embodiments, the HAT modulator is a HAT activator. In some embodiments, the HAT modulator is a HAT inhibitor. In other embodiments, the HDAC modulator is a HDAC inhibitor. In other embodiments, the HDAC modulator is a HDAC activator.

In some embodiments, a HAT modulator is administered together with a HDAC modulator such as, for example, romidepsin, to patients with cancer or a neurodegenerative disease. In some embodiments, there is a synergistic effect between the HAT modulator and the HDAC modulator.

In some embodiments, the present invention provides a method for treating or preventing or cancer or a neurodegenerative disease by combined use of a HAT modulator and a HDAC modulator. In some embodiments, the methods comprise administering an amount of a HAT modulator or a pharmaceutically acceptable salt thereof in combination with an amount of a HDAC modulator, or a pharmaceutically acceptable salt thereof to a subject to treat or prevent cancer or a neurodegenerative disease. In some embodiments, a synergistic effect is observed between the HAT modulator and the HDAC modulator. In some embodiments, the HAT modulator or a pharmaceutically acceptable salt thereof and HDAC modulator, or a pharmaceutically acceptable salt thereof are administered in a therapeutically effective amount. In some embodiments, the HAT modulator, or a pharmaceutically acceptable salt thereof, along with a HDAC modulator or a pharmaceutically acceptable salt thereof, may be a part of a pharmaceutical composition and may be delivered alone or with other agents in combination with a pharmaceutically acceptable carrier. In some embodiments, the agent is another agent that treats cancer or neurodegenerative disease. In some embodiments, the HDAC modulator is selected from the group consisting of romidepsin, vorinostat, belinostat, panobinostat, entinostat, mocetinostat, abexinostat, quisinostat, gavinostat and combinations thereof. In some embodiments, the HDAC modulator is romidepsin. In another embodiment, the HDAC inhibitor is chidamide, resminostat, givinostat, or kevetrin.

In some embodiments, the present invention provides a method for treating and/or preventing cancer or a neurodegenerative disease by combined use of a HAT modulator and a HDAC modulator in subjects. In some embodiments, there is a synergistic effect between a HAT modulator and a HDAC modulator. Thus, in some embodiments, a HAT modulator and a HDAC modulator are administered in amounts that exhibit synergistic treatment of cancer or neurodegenerative disease. In some embodiments, a HAT modulator and a HDAC modulator are administered in amounts that exhibit synergistic treatment and/or prevention of cancer or neurodegenerative disease.

The precise dose to be employed in the compositions will also depend on the route of administration, and the seriousness of the affliction or disorder, and should be decided according to the judgment of the practitioner and each patient's circumstances. In specific embodiments of the invention, a HDAC modulator such as, for example, romidepsin can be administered by known methods and dose ranges.

In some embodiments, the doses are used when a HAT modulator is administered alone. In some embodiments, the doses are used when a HAT modulator is administered in combination with a HDAC modulator. In some embodiments, the doses are administered orally. In some embodiments, the doses are administered intravenously.

The HAT modulator and HDAC modulator (or pharmaceutically acceptable salts of either HAT modulator and HDAC modulator or both) can be administered at different times or at the same time.

In some embodiments, the compositions of the invention comprise a HAT modulator and a HDAC modulator. In some embodiments, a HAT modulator and a HDAC modulator are present together in a single dosage form such as, for example, an oral dosage form. In some embodiments, a HAT modulator and a HDAC modulator are present together in a single dosage form such as, for example, an intravenous dosage form. In some embodiments, a HAT modulator and a HDAC modulator are administered separately. In some embodiments, a HAT modulator is present together in a single dosage form such as, for example, an oral dosage form. In some embodiments, a HAT modulator is present together in a single dosage form such as, for example, an intravenous dosage form. In some embodiments, a HDAC modulator is present together in a single dosage form such as, for example, an oral dosage form. In some embodiments, a HDAC modulator is present together in a single dosage form such as, for example, an intravenous dosage form.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, rat, dog, cat, cow, horse, rabbit, monkey, pig, sheep, goat, or human. In some embodiments, the subject is mouse, rat, monkey, dog or human. In some embodiments, the subject is a mouse, monkey or human. In some embodiments, the subject is a human.

A pharmaceutical composition of the invention can be formulated to be compatible with its intended route of administration. Exemplary routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The injectable composition should be sterile and should be fluid to the extent that easy syringability exists. It should also be stable under the conditions of manufacture and storage and preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many embodiments, it can be useful to include isotonic agents, for example, sugars, polyalcohols such as mannitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the HAT modulator compound and the HDAC modulator compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. It will be recognized that one or more features of any embodiments or aspects disclosed herein can be combined and/or rearranged within the scope of the invention to produce further embodiments that are also within the scope of the invention.

As will be apparent to one of ordinary skill in the art from a reading of this disclosure, the embodiments of the present disclosure can be embodied in forms other than those specifically disclosed above. The particular embodiments described herein are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

The invention is further described by the following non-limiting Examples. Examples of mouse models for neurodegenerative diseases, including, Alzheimer's Disease, Huntington's Disease and Parkinson's Disease are described in WO 2011/072243 and WO 2012/088420, each incorporated by reference herein in its entirety.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

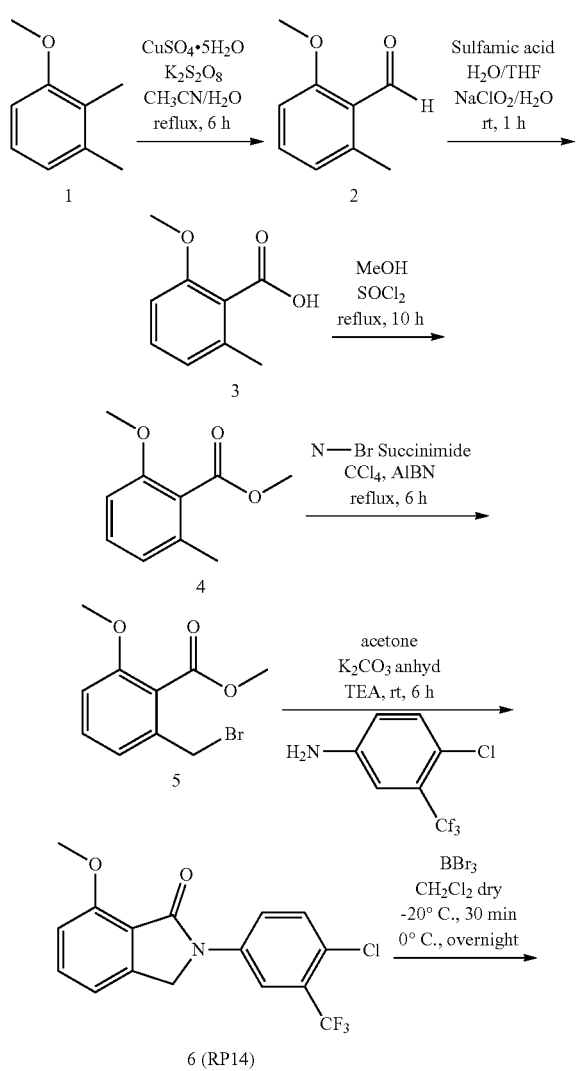

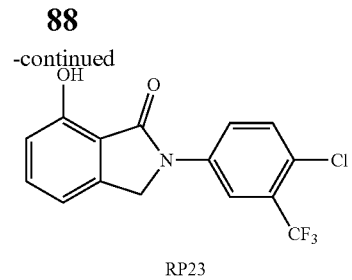

Methyl 2-methoxy-6-methylbenzoate, 4

A vigorously mixture of 1-methoxy-2,3-dimethylbenzene (1, 1.34 mL), Copper (II) Sulfate pentahydrate (2.5 g) and potassium peroxodisulfate (8.1 g) in acetonitrile/water 1:1 (70 mL) was heated at reflux for 6 h. The reaction was cooled to room temperature and was extracted with dichloromethane (3 times). The organic layer was dried over $Na_2SO_4$, filtered and evaporated to produce the desired liquid product (2) suitable for further reaction without purification. A solution of 2 (1.50 g) and sulfamic acid (1.30 g) in water (22.5 mL) and THF (11.2 mL) was stirred at room temperature and after 5 min a solution of $NaClO_2$ (1.180 g) in water (5 mL) was added. The reaction was stirred at room temperature for 1 h and then was extracted with ethyl acetate. The organic layer was separated and extracted with NaOH 1M. The aqueous solution was acidified with HCl 6N and extracted with dichloromethane. The organic layer was dried over $Na_2SO_4$, filtered and evaporated to obtain the solid product (3, 1.071 g). Thionyl chloride (0.55 mL) was added dropwise to a solution of 3 (83 mg) in methanol (0.5 mL) and the reaction was refluxed for 10 h. The methanol was removed by rotary evaporator and the residue was dilutes with water and extracted with ethyl acetate. The organic layer was washed with saturated solution of $NaHCO_3$ and then separated, dried over $Na_2SO_4$, filtered and evaporated to produce the crude product. Purification by flash chromatography gave the desired product as colorless oil (70 mg, yield 80%). $C_{10}H_{12}O_3$, MS-ES: $[M+H]^+=181$ m/z. $^1$H-NMR: ($CDCl_3$, 300 MHz) δ 2.29 (s, 3H, —$CH_3$), 3.83 (s, 3H, —$OCH_3$), 3.92 (s, 3H, —C(=O)$OCH_3$), 6.76 (d, 1H, Jo=8.7 Hz, H-5), 6.80 (dd, 1H, Jo=7.8 Hz, Jm=0.6 Hz, H-3), 7.25 (t, 1H, Jo=7.5 Hz, Jm=8.4 Hz, H-4).

methyl 2-(bromomethyl)-6-methoxybenzoate, 5

N-Bromosuccinimide (250 mg) and catalytic amount of 2,2'-Azobis(2-methylpropionitrile) was added to a solution of 4 (252 mg) in carbon tetrachloride (3.5 mL). The reaction was heated to reflux in the present of visible light for 6 h. After cooling to room temperature the reaction was filtered and the filtrate was evaporated. The residue was diluted with water and extracted with diethyl ether. The organic layer was dried over $Na_2SO_4$, filtered and evaporated. The obtained residue was purified by flash chromatography to produce the desired product (195 mg, yield 60%). $C_{10}H_{11}BrO_3$, MS-ES: $[M+H]^+=259$ m/z, $[M+H]^++2=261$ m/z. $^1$H-NMR: ($CDCl_3$, 300 MHz) δ 3.83 (s, 3H, —$OCH_3$), 3.94 (s, 3H, —C(=O)$OCH_3$), 4.48 (s, 2H, —$CH_2Br$), 6.89 (d, 1H, Jo=8.4 Hz, H-5), 7.00 (d, 1H, Jo=7.5 Hz, H-3), 7.33 (t, 1H, Jo=8.1 Hz, H-4).

2-(4-chloro-3-(trifluoromethyl)phenyl)-7-methoxyisoindoline-1-one, 6

A solution of 5 (130 mg), 4-chloro-3-(trifluoromethyl) aniline (98 mg), triethylamine (105 µL) and $K_2CO_3$ (10 mg)

was refluxed in acetone (1 mL) for 6 h. The reaction was extracted with ethyl acetate and water. The organic layer was dried over $Na_2SO_4$, filtered and evaporated. The crude product was purified by flash chromatography (dichloromethane/ethyl acetate, 9.5:0.5) to obtain the desired product (65 mg, yield 80%). $C_{16}H_{11}ClF_3NO_2$, MS-ES: $[M+H]^+=$ 342 m/z. $^1$H-NMR: ($CDCl_3$, 300 MHz) δ 4.01 (s, 3H, —$OCH_3$), 4.80 (s, 2H, —$CH_2$), 6.95 (d, 1H, Jo=8.1 Hz, H-4), 7.08 (d, 1H, Jo=7.2 Hz, H-6), 7.52 (d, 1H, Jo=9.0 Hz, H-5'), 7.56 (t, 1H, Jo=8.0 Hz, H-5), 8.06 (dd, 1H, Jo=9.2 Hz, Jm=2.7 Hz, H-6'), 8.23 (d, 1H, Jm=2.7 Hz, H-2').

2-(4-chloro-3-(trifluoromethyl)phenyl)-7-hydroxyisoindolin-1-one, RP23

Boron tribromide (1M in dichloromethane, 0.4 mL) was added dropwise to a solution of 6 (34 mg) in 1 mL of dichloromethane at −20° C. The reaction was stirred for 30 min at −20° C. and overnight at 0° C. The mixture was poured into ice-cold water and stirred for 30 min at room temperature. The product was filtered and washed with water to obtain the desired product (30 mg, yield: 89%). $C_{15}H_9ClF_3NO_2$, MS-ES: $[M+H]^+=328$ m/z. $^1$H-NMR: ($CDCl_3$, 300 MHz) δ 4.86 (s, 2H, —$CH_2$), 6.93 (dd, 1H, Jo=8.7 Hz, Jm=0.6 Hz, H-4), 7.02 (dd, 1H, Jo=7.8 Hz, Jm=0.6 Hz, H-6), 7.51 (t, 1H, Jo=8.0 Hz, H-5), 7.55 (d, 1H, Jo=9.0 Hz, H-5'), 8.04 (dd, 1H, Jo=8.7 Hz, Jm=2.7 Hz, H-6'), 8.14 (d, 1H, Jm=2.7 Hz, H-2'), 8.57 (s, 1H, sc. $D_2O$, OH).

Example 2

Scheme 2

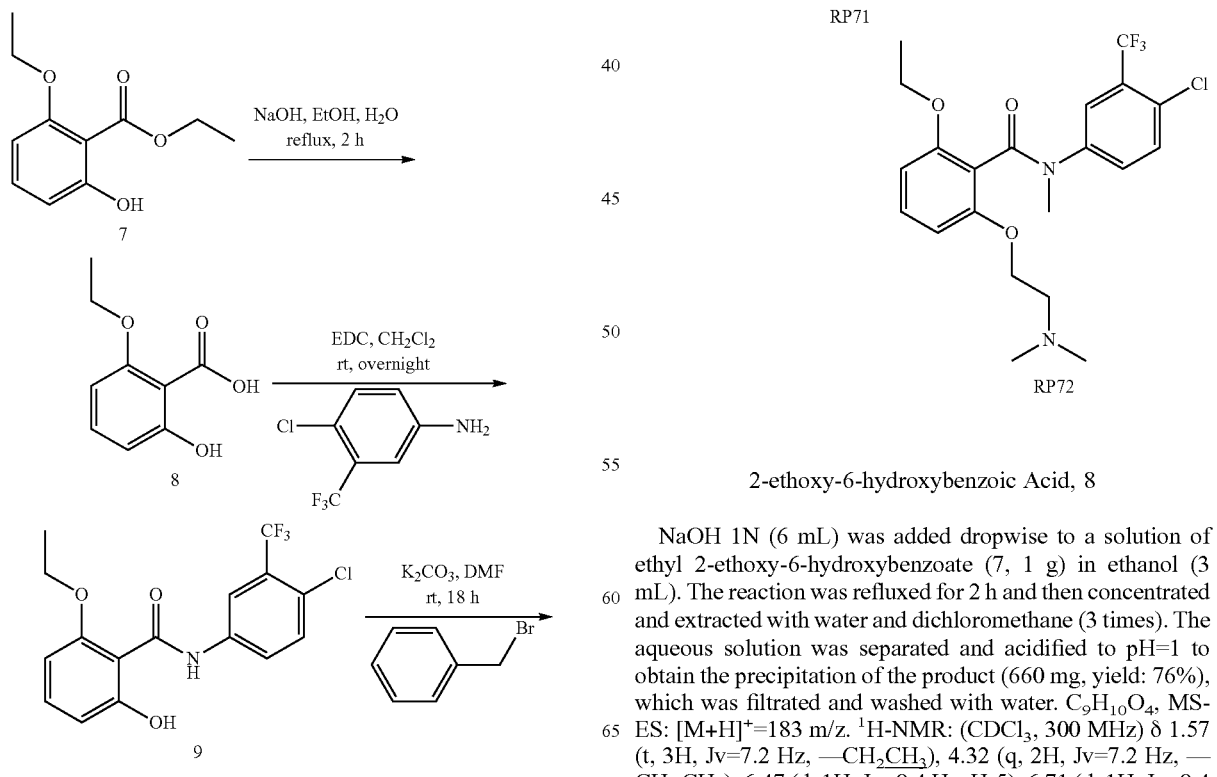

2-ethoxy-6-hydroxybenzoic Acid, 8

NaOH 1N (6 mL) was added dropwise to a solution of ethyl 2-ethoxy-6-hydroxybenzoate (7, 1 g) in ethanol (3 mL). The reaction was refluxed for 2 h and then concentrated and extracted with water and dichloromethane (3 times). The aqueous solution was separated and acidified to pH=1 to obtain the precipitation of the product (660 mg, yield: 76%), which was filtrated and washed with water. $C_9H_{10}O_4$, MS-ES: $[M+H]^+=183$ m/z. $^1$H-NMR: ($CDCl_3$, 300 MHz) δ 1.57 (t, 3H, Jv=7.2 Hz, —$CH_2\underline{CH_3}$), 4.32 (q, 2H, Jv=7.2 Hz, —$\underline{CH_2}CH_3$), 6.47 (d, 1H, Jo=8.4 Hz, H-5), 6.71 (d, 1H, Jo=8.4 hz, H-3), 7.39 (t, 1H, Jo=8.4 Hz, H-4), 11.60 (s, 1H, C(=O)OH), 12.16 (s, 1H, OH).

N-(4-chloro-3-(trifluoromethyl)phenyl)-2-ethoxy-6-hydroxybenzamide, 9

N-(3-Dimethylaminopropyl)-N'-ethylcarbodiimide hydrochloride (900 mg) was added gradually to a solution of 8 (660 mg) and 4-chloro-3-(trifluoromethyl)aniline (780 mg) in dichloromethane (5 mL) at 0° C. The reaction was stirred at room temperature overnight then filtered and the precipitate was crystallized from methanol (608 mg, yield: 67%). $C_{16}H_{13}ClF_3NO_3$, MS-ES: $[M+H]^+$=360 m/z. $^1$H-NMR: (CDCl$_3$, 300 MHz) δ 1.65 (t, 3H, Jv=6.9 Hz, —CH$_2$CH$_3$), 4.27 (q, 2H, Jv=6.9 Hz, —CH$_2$CH$_3$), 6.44 (d, 1H, Jo=8.4 Hz, H-5), 6.67 (d, 1H, Jo=8.4 Hz, H-3), 7.32 (t, 1H, Jo=8.4 Hz, H-4), 7.48 (d, 1H, Jo=8.7 Hz, H-5'), 7.77 (dd, 1H, Jo=8.7 Hz, Jm=2.4 Hz, H-6'), 7.91 (d, 1H, Jm=2.1 Hz, H-2'), 10.66 (s, 1H, —C(=O)NH), 13.29 (s, 1H, OH).

2-(benzyloxy)-N-(4-chloro-3-(trifluoromethyl)phenyl)-6-ethoxybenzamide, RP62

Benzyl bromide (24 μL) was added to a suspension of 9 (70 mg) and K$_2$CO$_3$ (36 mg) in DMF (1.5 mL). The reaction was stirred at room temperature and after 18 h the solvent was evaporated under vacuum and the residue partitioned between saturated aqueous solution of NaHCO$_3$ and ethyl acetate. The organic layer was separated, dried over Na$_2$SO$_4$, filtered and evaporated. Purification by flash chromatography (Hexane/Ethyl acetate, 8:2) gave the desired product (50 mg, yield: 60%). $C_{23}H_{19}ClF_3NO_3$, MS-ES: $[M-H]^-$=448 m/z, $[M+H]^+$=450 m/z. $^1$H-NMR: (DMSO-d$_6$, 400 MHz) δ 1.20 (t, 3H, Jv=6.9 Hz, —CH$_2$-CH$_3$), 4.02 (q, 2H, Jv=6.9 Hz, —CH$_2$—CH$_3$), 5.10 (s, 2H, CH$_2$-Ph), 6.70 (d, 1H, Jo=7.6 Hz, H-3), 6.74 (d, 1H, Jo=8.4 Hz, H-5), 7.12-7.34 (m, 6H), 7.49 (d, 1H, Jo=9.2 Hz, H-5'), 7.90 (dd, 1H, Jo=8.8 Hz, Jm=2.4 Hz, H-6'), 8.25 (d, 1H, Jm=2.4 Hz, H-2'), 10.67 (s, 1H, NH).

2-(benzyloxy)-N-(4-chloro-3-(trifluoromethyl)phenyl)-6-ethoxy-N-methylbenzamide, RP65

Iodomethane (20 μL) was added to suspension of RP62 (70 mg) and NaH (60% oil disp., 9 mg) in THF (2 mL) at room temperature. The reaction was stirred and after 12 h the solvent was evaporated and the residue was diluted with HCl 1M and extracted with dichloromethane (2 times). The organic layer was dried over Na$_2$SO$_4$, filtered and evaporated obtaining the desired product (80 mg, yield: 30%). $C_{24}H_{21}ClF_3NO_3$, MS-ES: $[M+H]^+$=464 m/z. $^1$H-NMR: (CDCl$_3$, 400 MHz) δ 1.40 (dt, 3H, Jv=7.2 Hz, —CH$_2$CH$_3$), 3.40 (s, 3H, N—CH$_3$), 3.90 (dd, 1H, Jv=7.2 Hz, —CH$_2$CH$_3$), 4.03 (dd, 1H, Jv=7.2, —CH$_2$CH$_3$), 4.90 (d, 1H, Jv=12 Hz, CH$_2$-Ph), 5.05 (d, 1H, Jv=12 Hz, CH$_2$-Ph), 6.33 (dd, 2H, Jo=7.6 Hz, H-3 and H-5), 7.04 (t, 1H, Jo=8.8 Hz, H-4), 7.11 (dd, 1H, Jm=2.8 Hz, Jo=9.0 Hz, H-6'), 7.18 (d, 1H, Jo=8.8 Hz, H-5'), 7.26-7.38 (m, 5H), 7.46 (d, 1H, Jm=2.4 Hz, H-2').

N-(4-chloro-3-(trifluoromethyl)phenyl)-2-ethoxy-6-hydroxy-N-methylbenzamide, RP71

A solution of RP65 (80 mg) in ethyl acetate was hydrogenated at atmospheric pressure over 10% Pd/C (19 mg) for 24 h. The mixture was filtered and the filtrate was evaporated to give the product (60 mg, yield: 94%). $C_{17}H_{15}ClF_3NO_3$.

$^1$H-NMR: (CDCl$_3$, 400 MHz) δ 1.20-1.22 (m, 3H, —CH$_2$CH$_3$), 3.42 (s, 3H, N—CH$_3$), 3.54-3.60 (m, 2H, —CH$_2$CH$_3$), 6.06 (d, 1H, Jo=8.4 Hz, H-3), 6.49 (d, 1H, Jo=8.4 Hz, H-5), 7.02-7.06 (m, 2H, H-6' and H-5'), 7.02-7.08 (m, 1H, H4), 7.40-7.42 (m, 1H, H-2'), 7.68 (s, 1H, OH).

Example 3

Scheme 3

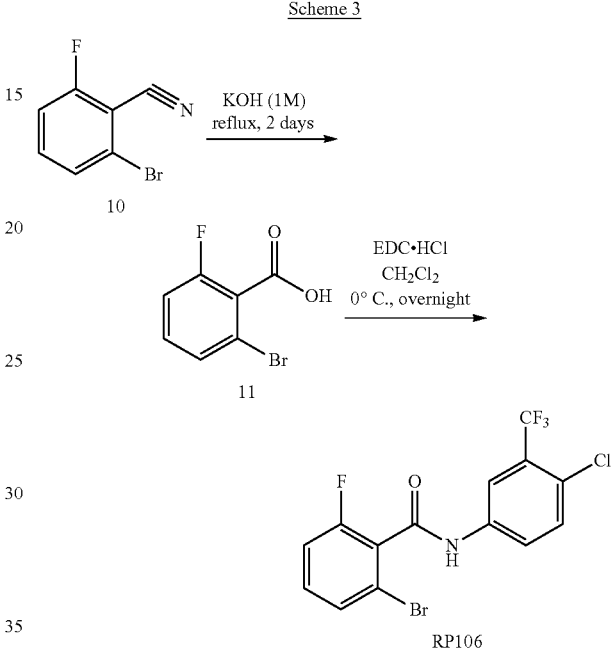

2-bromo-6-fluorobenzoic Acid, 11

A solution 2-bromo-6-fluorobenzonitrile 10 in KOH 1M (25 mL) was stirred to reflux for 2 day. The reaction was cooled to room temperature and the HCl concentrate was added to pH=2-3. The aqueous solution was extracted with ethyl acetate (3 times). The organic layer was separated, dried and evaporated to obtain the desired product (126 mg, yield: 95%). $C_7H_4BrFO_2$, MS-ES: $[M-H]^-$=218 m/z. $^1$H-NMR: (CDCl$_3$, 400 MHz) δ 7.14 (t, 1H, Jo=8.4 Hz, H-4), 7.29-7.35 (m, 1H, H-3), 7.45 (d, 1H, H-5).

2-bromo-N-(4-chloro-3-(trifluoromethyl)phenyl)-6-fluorobenzamide, RP106

N-(3-Dimethylaminopropyl)-N'-ethylcarbodiimide hydrochloride (EDC HCl, 74 mg) was added to a solution of 11 (65 mg) in dichloromethane (0.5 mL) at 0° C., and then 4-chloro-3-(trifluoromethyl)aniline (64 mg) was added. The solution was stirred at room temperature for 24 h. The solvent was evaporated and the residue was crystallized from methanol (55 mg, yield: 47%). $C_{14}H_7BrClF_4NO$, MS-ES: $[M-H]^-$=394 m/z. $^1$H-NMR: (CDCl$_3$, 400 MHz) δ 7.10 (t, 1H, Jo=8.4 Hz, H-4), 7.30-7.40 (m, 3H, H-3, H-6' and H-5'), 7.02-7.08 (m, 1H, H-5), 7.40-7.42 (m, 1H, H-2'), 7.60 (s, 1H, NH).

Example 4

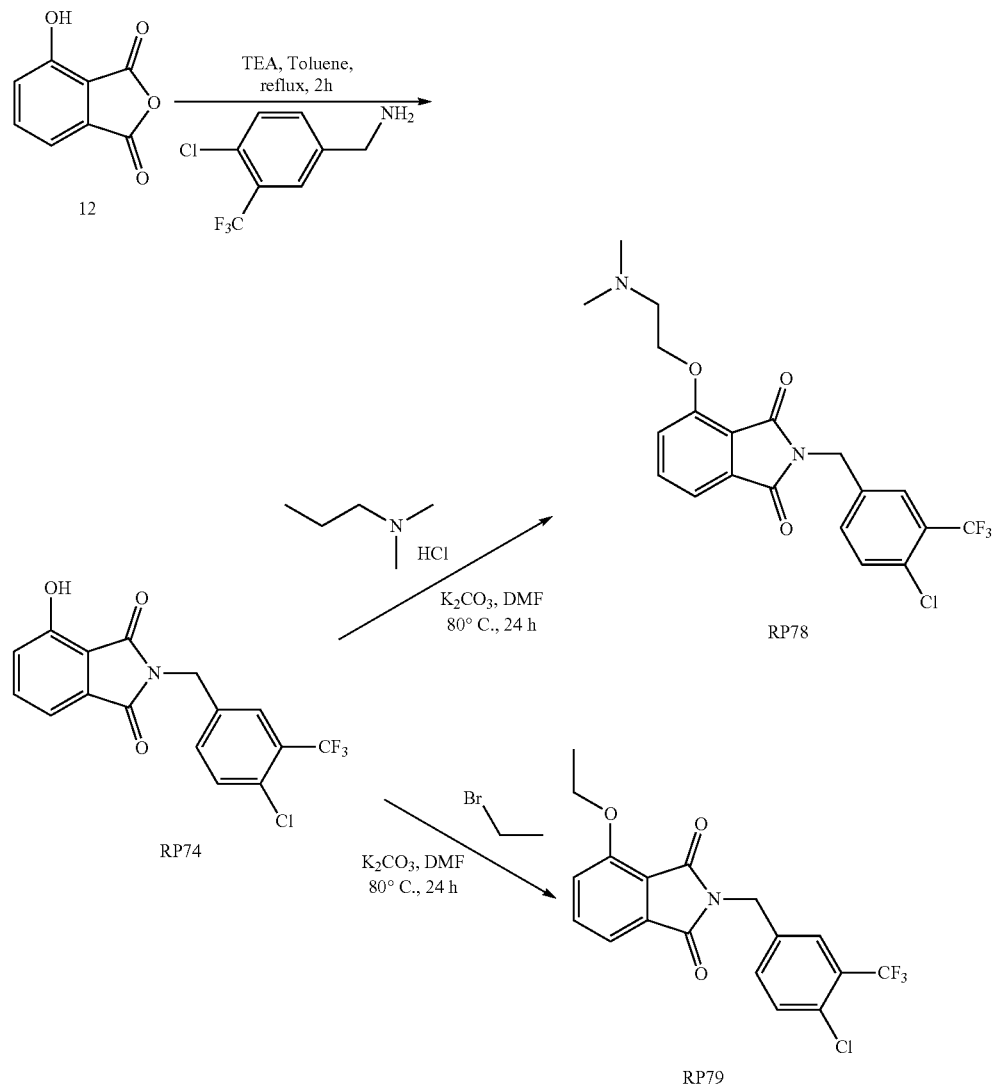

Scheme 4

2-(4-chloro-3-(trifluoromethyl)benzyl)-4-hydroxyisoindoline-1,3-dione, RP74

A solution of 12 (100 mg) and 4-chloro-3-(trifluoromethyl)benzylamine (111 µL) in acetic acid (3 mL) was heated to reflux for 2 h. The solvent was evaporated and the residue was extracted with dichloromethane and water. The organic layer was dried over $Na_2SO_4$, filtered and evaporated. The crude product was purified by flash chromatography (dichloromethane/methanol, 9.9:0.1)(89 mg, yield: 45%). $C_{16}H_9ClF_3NO_3$, MS-ES: $[M-H]^-=354$ m/z. $^1$H-NMR: ($CDCl_3$, 400 MHz) 4.79 (s, 2H, $CH_2$-Ph), 7.16 (d, 1H, Jo=8.0 Hz, H-7), 7.38 (d, 1H, Jo=6.8 Hz, H-5), 7.45 (d, 1H, Jo=8.4 Hz, H-5'), 7.52 (dd, 1H, Jo=7.6 Hz, Jm=2.0 Hz, H-6'), 7.51-7.53 (br s, 1H, OH), 7.58 (dd, 1H, Jo=8.8 Hz, Jo=8.4 Hz, H-6), 7.72 (d, 1H, Jm=2.0 Hz, H-2').

2-(4-chloro-3-(trifluoromethyl)benzyl)-4-(2-(dimethylamino)ethoxy)isoindoline-1,3-dione, RP78

A suspension of RP74 (89 mg), 2-Chloro-N,N-dimethylethylamine hydrochloride (40 mg), and $K_2CO_3$ (86 mg) in DMF (2 mL) was stirred at 80° C. for 24 h. The reaction mixture was diluted with dichloromethane and washed with water (3 times). The organic layer was dried over $Na_2SO_4$, filtered and evaporated. The crude product was purified by flash chromatography (methanol/ethyl acetate, 5:5) to provide the desired product (40 mg, yield: 40%). $C_{20}H_{18}ClF_3N_2O_3$, MS-ES: $[M+H]^+=427$ m/z. $^1$H-NMR: ($CDCl_3$, 400 MHz) 2.37 (s, 6H, —$N(CH_3)_2$), 2.83 (t, 2H, Jv=6.0 Hz, —$OCH_2CH_2$—N—), 4.26 (t, 2H, Jv=6.0 Hz, —$OCH_2CH_2$—N—), 4.78 (s, 2H, $CH_2$-Ph), 7.18 (d, 1H, Jo=8.0 Hz, H-7), 7.42 (d, 1H, Jo=8.4 Hz, H-5), 7.43 (d, 1H, Jo=6.8 Hz, H-5'), 7.53 (dd, 1H, Jo=8.4 Hz, Jo=8.0 Hz, Jm=2.0 Hz, H-6'), 7.63 (dd, 1H, Jo=8.8 Hz, Jo=8.4 Hz, H-6), 7.72 (d, 1H, Jm=2.0 Hz, H-2').

2-(4-chloro-3-(trifluoromethyl)benzyl)-4-ethoxyisoindoline-1,3-dione, RP79

A suspension of RP74 (95 mg), bromoethane (23 µL), and K$_2$CO$_3$ (93 mg) in DMF (2.5 mL) was stirred at 80° C. for 24 h. The reaction mixture was diluted with dichloromethane and washed with water (3 times). The organic layer was dried over Na$_2$SO$_4$, filtered and evaporated. The crude product was purified by flash chromatography (hexane/ethyl acetate, 6:4) to provide the desired product (95 mg, yield: 93%). C$_{18}$H$_{13}$ClF$_3$NO$_3$, MS-ES: [M+H]$^+$=384 m/z. $^1$H-NMR: (CDCl$_3$, 400 MHz) δ 1.50 (t, 3H, Jv=7.2 Hz, —CH$_2$CH$_3$), 4.24 (q, 2H, Jv=7.2 Hz, —CH$_2$CH$_3$), 4.78 (s, 2H, CH$_2$-Ph), 7.16 (d, 1H, Jo=8.0 Hz, H-7), 7.40 (d, 1H, Jo=7.2 Hz, H-5), 7.41 (d, 1H, Jo=8.4 Hz, H-5'), 7.54 (dd, 1H, Jo=8.4 Hz, Jm=2.0 Hz, H-6'), 7.62 (dd, 1H, Jo=7.2 Hz, H-6), 7.72 (d, 1H, Jm=2.0 Hz, H-2').

Example 5

Scheme 5

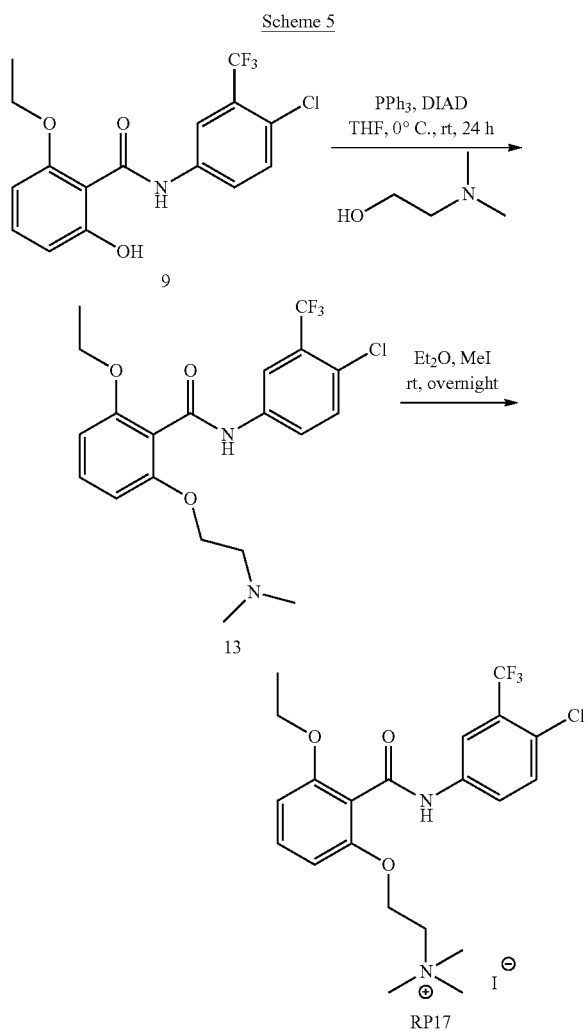

N-(4-chloro-3-(trifluoromethyl)phenyl)-2-(2-(dimethylamino)ethoxy)-6-ethoxybenzamide, 13

Diisopropyl azodicarboxylate (128 µL) was added to a solution of 9, 2-Dimethylaminoethanol (65 µL) and triphenylphosphine (170 mg) in THF (2.5 mL) at 0° C. The solution was stirred at room temperature overnight. The solvent was evaporated and the residue was diluted in ethyl acetate and washed with water and brine (3 times). The organic layer was dried over Na$_2$SO$_4$, filtered and evaporated. Purification by flash chromatography (dichloromethane/methanol, 9.4:0.6) gave the desired colorless oil. C$_{20}$H$_{22}$ClF$_3$N$_2$O$_3$, MS-ES: [M+H]$^+$=431 m/z. $^1$H-NMR: (CDCl$_3$, 400 MHz) δ 1.39 (t, 3H, Jv=6.9 Hz, O—CH$_2$CH$_3$), 2.25 (s, 6H, N(CH$_3$)$_2$), 2.65 (t, 2H, Jv=5.4 Hz, —OCH$_2$CH$_2$N—), 4.09 (q, 2H, Jv=6.9 Hz, —OCH$_2$CH$_3$), 4.19 (t, 2H, Jv=5.4 Hz, —OCH$_2$CH$_2$N—), 6.59 (d, 1H, Jo=8.7 Hz, H-3), 6.60 (d, 1H, Jo=8.7 Hz, H-5), 7.28 (t, 1H, Jo=8.4 Hz, Jo=8.7 Hz, H-4), 7.46 (d, 1H, Jo=8.4 Hz, H-5'), 7.80 (s, 1H, H-2'), 7.98 (d, 1H, Jo=8.1, H-6'), 8.71 (s, 1H, NH).

2-(2-((4-chloro-3-(trifluoromethyl)phenyl)carbamoyl)-3-ethoxyphenoxy)-N,N,N-trimethylethane-1-aminium iodide, RP17

Iodomethane (21 µL) was added to a solution of 13 (86 mg) in diethyl ether (1.2 mL) and the reaction was stirred at room temperature overnight. The white precipitate was collected by filtration and dried under vacuum to give the desired product (75 mg, yield: 65%). C$_{21}$H$_{25}$ClF$_3$IN$_2$O$_3$, MS-ESI: [M]$^+$=445 m/z. $^1$H-NMR: (DMSO-d$_6$, 400 MHz) δ 1.22 (t, 3H, Jv=7.1 Hz, —OCH$_2$CH$_3$), 3.04 (s, 9H, —N(CH$_3$)$_3$), 3.64 (m, 2H, —OCH$_2$CH$_2$N), 4.06 (q, 2H, Jv=6.9 Hz, —OCH$_2$CH$_3$), 4.45 (m, 2H, —OCH$_2$CH$_2$N), 6.79 (dd, 2H, Jo=8.7 Hz, Jm=2.0 Hz, H-4 and H-6), 7.39 (t, 1H, Jo=8.4 Hz, H-5), 7.67 (d, 1H, Jo=8.7 Hz, H-5'), 7.86 (d, 1H, Jo=8.1 Hz, H-6'), 8.27 (d, 1H, Jm=2.4 Hz, H-2'), 10.67 (s, 1H, NH).

Example 6

Isatoic anhydride was reacted with 4-chloro-3-trifluoromethyl aniline to provide RP 95:

Scheme 6

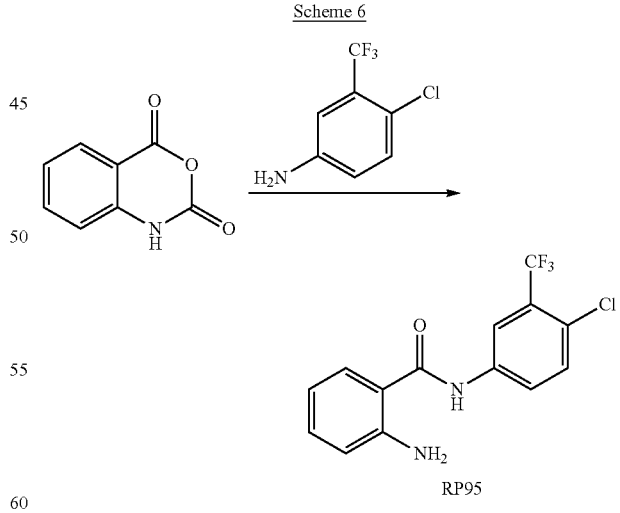

Example 7

2-bromo benzoic acid was reacted with 4-chloro-3-trifluoromethyl aniline to provide RP 101. RP 102 was obtained via reaction of RP101 with N, N-dimethylethane diamine.

Scheme 7

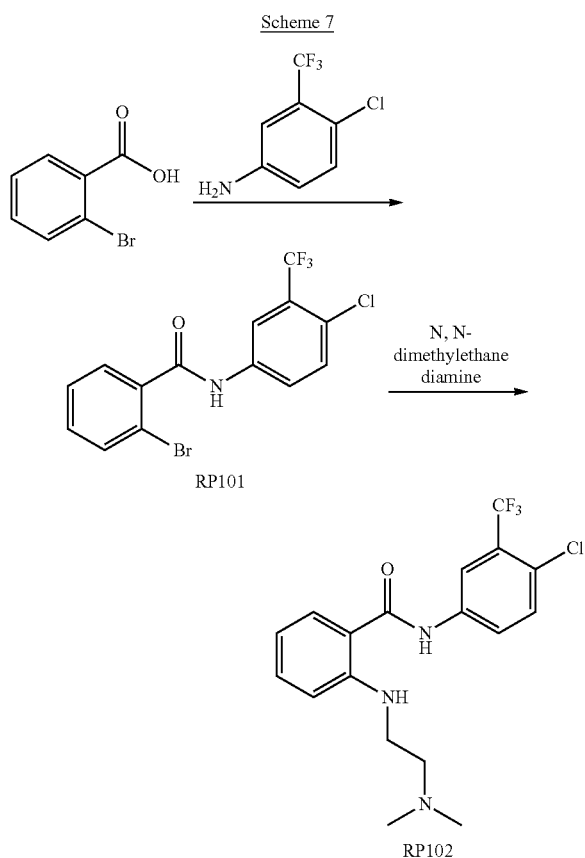

Example 8

Figure 21:
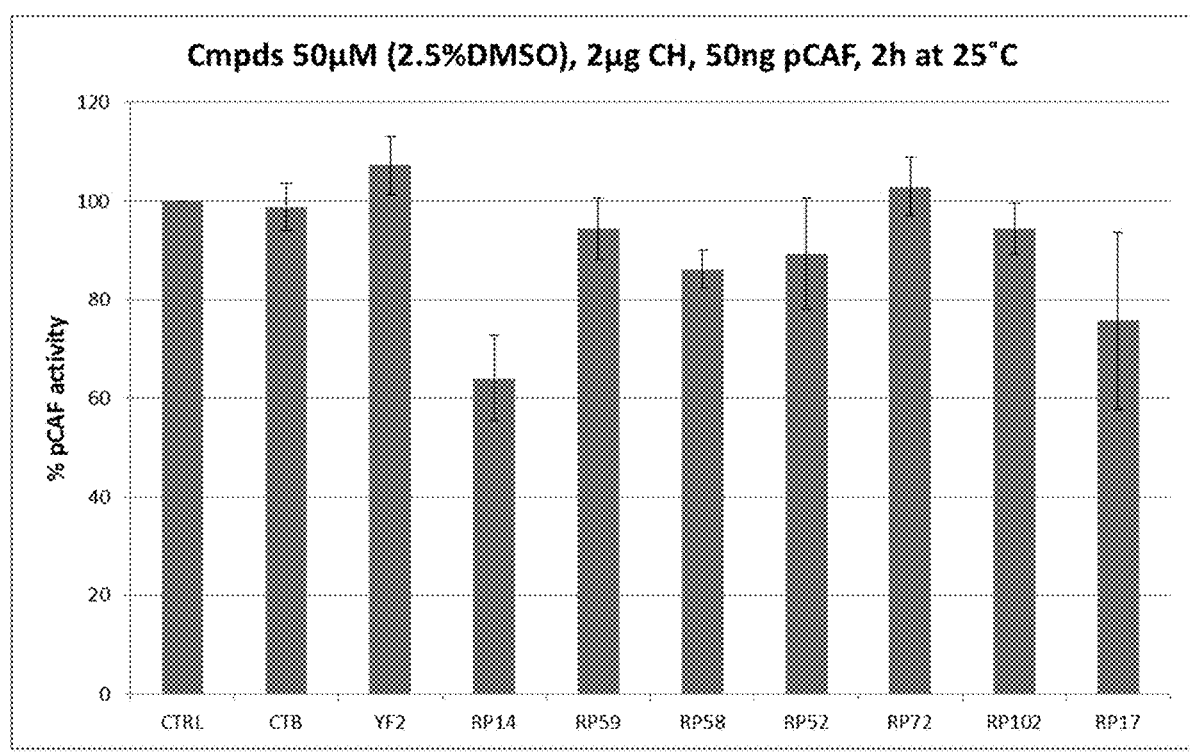
FIG. 21 shows in vitro measurement of pCAF activity for compounds.

In vitro measurements of pCAF enzymatic activity were performed with radioassay in which active pCAF (recombinant protein expressed in *E. Coli*, Millipore) was used to acetylate core histones (chicken erythrocyte histones, Millipore) in vitro with tracer levels of tritiated acetyl-CoA (Perkin Elmer) as the acetyl donor. Results are shown in FIG. 21.

Example 9

Histone Acetyl Transferase Activators as a Therapeutic Agent for Cancer and Inflammatory Diseases.

Described herein is a group of chemical entities which activate histone acetyl transferases leading to acetylation of p53 and induction of p21, at concentrations between 1-10 uM. The name of the chemical identities that were tested are: YF2, JF1, JF2, JF3, JF4, JF5, JF7, JF8, JF9, JF10, JF16, JF18, RP4, RP7, RP23, RP52, RP58, RP59, RP72, RP78, RP79, RP102. See FIGS. 1-4 for the structures and scheme of synthesis of representative compounds. Syntheses of other chemical entities are described, for example, in WO 2011/072243; WO 2012/088420; and U.S. Patent Publication No. 2013/0121919; each herein incorporated by reference in its entirety. Treatment of lymphoma cell lines with HAT activators as a single agent has a modest impact on cell viability over 24-72 hours. However, the combination of HAT inducer (RP52, RP59, but not RP14) with a HDAC inhibitor such as romidepsin produces synergy coefficients lower as low as 0.14 starting at 48 hours (synergy coefficients less than 1 indicate synergy) and reduced cell viability (FIGS. 5-18).

Luminetric assays for synergy between romidepsin and RP14 evaluated in different cell lines (FIGS. 5-7): Cells were untreated (bar labeled "c"); treated with 1.5 nM Romidepsin alone (bar labeled "1.5 R"); treated with RP14 alone at increasing concentrations from 1-10 μm (bar labeled 1, 2, 4, 6, 8, or 10); or treated with 1.5 nM Romidepsin in combination with RP14 at increasing concentrations from 1-10 μm (bar labeled R+1, R+2, R+4, R+6, R+8, or R+10).

Luminetric assays for synergy between romidepsin and RP52 evaluated in different cell lines (FIGS. 8-10): Cells were untreated (bar labeled "c"); treated with 1.5 nM Romidepsin alone (bar labeled "1.5 R"); treated with RP52 alone at increasing concentrations from 1-10 μm (bar labeled 1, 2, 4, 6, 8, or 10); or treated with 1.5 nM Romidepsin in combination with RP52 at increasing concentrations from 1-10 μm (bar labeled R+1, R+2, R+4, R+6, R+8, or R+10).

Luminetric assays for synergy between romidepsin and RP59 evaluated in different cell lines (FIGS. 11-13): Cells were untreated (bar labeled "c"); treated with 1.5 nM Romidepsin alone (bar labeled "1.5 R"); treated with RP59 alone at increasing concentrations from 1-10 μm (bar labeled 1, 2, 4, 6, 8, or 10); or treated with 1.5 nM Romidepsin in combination with RP59 at increasing concentrations from 1-10 μm (bar labeled R+1, R+2, R+4, R+6, R+8, or R+10).

Luminetric assays for synergy between romidepsin and different HAT activators (RP14, RP52, RP72, JF2) evaluated in different cell lines (FIGS. 14-15): Cells were untreated (bar labeled "H9"); treated with 2.5 nM Romidepsin alone (bar labeled "R 2.5 nM"); treated with HAT activator alone (bar labeled RP14, RP52, RP72, JF2); or treated with 2.5 nM Romidepsin in combination with HAT activator (bar labeled R+RP14, R+RP52, R+RP72, R+JF2).

Luminetric assays for synergy between romidepsin and RP14 evaluated in different cell lines (FIGS. 16-17): Cells were untreated (bar labeled "H9"); treated with 2 nM Romidepsin alone (bar labeled "R2 nM"); treated with RP14 alone at increasing concentrations from 0.1-10 μm (bar labeled RP14 0.1 μM, RP14 1 μM, RP14 2.5 μM, RP14 5 μM, RP14 10 μM); or treated with 2 nM Romidepsin in combination with RP14 at increasing concentrations from 0.1-10 μm (bar labeled R+RP14 0.1 μM, R+RP14 1 μM, R+RP14 2.5 μM, R+RP14 5 μM, R+RP14 10 μM).

Luminetric assays for synergy between romidepsin and RP72 evaluated in different cell lines (FIG. 18): Cells were untreated (bar labeled "HH"); treated with 1.25 nM Romidepsin alone (bar labeled "R1.25 nM"); treated with RP72 alone at increasing concentrations from 0.1-10 μm (bar labeled RP72 0.1 μM, RP72 1 μM, RP72 2.5 μM, RP72 5 μM, RP72 10 μM); or treated with 1.25 nM Romidepsin in combination with RP72 at increasing concentrations from 0.1-10 μm (bar labeled R+RP72 0.1 μM, R+RP72 1 μM, R+RP72 2.5 μM, R+RP72 5 μM, R+RP72 10 μM).

Treatment of diffuse large B-cell lymphoma cell lines (OCI-Ly1 and Su-DHL6) with RP52 lead to increased acetylation of p53 and induction of p21, a key regulator of the cell cycle (FIGS. 19A-B). Cells were treated with Romidepsin 1.5 nM, RP52 5 uM or the combination for 24 hours then lysed with RIPA buffer. Levels of total p53, acetylated p53, and p21 were detected by Western Blot analysis. Antibodies used were anti-acetyl-p53 (Santa Cruz), anti-p53 DO-1 (Abcam), anti-p21 (Cell Signaling).

The pharmaco-modulation of key tumor suppressors induced by HAT activators and their potent synergy with HDAC inhibitors give credence to the further development of these new chemical entities for the treatment of cancers and inflammatory disorders.

Figure 20A:
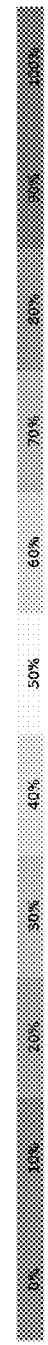
Figure 20B:
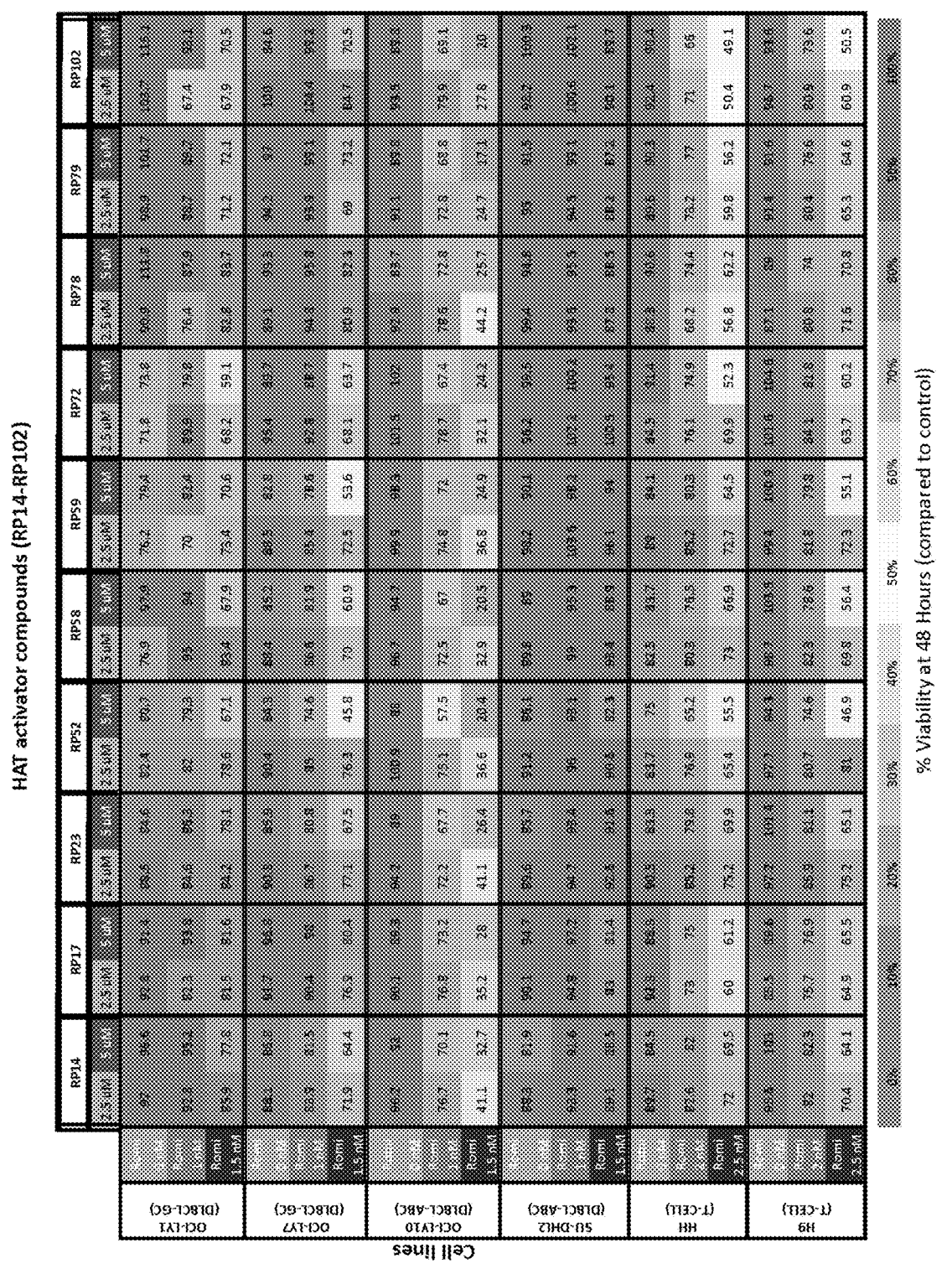
Figure 20C:
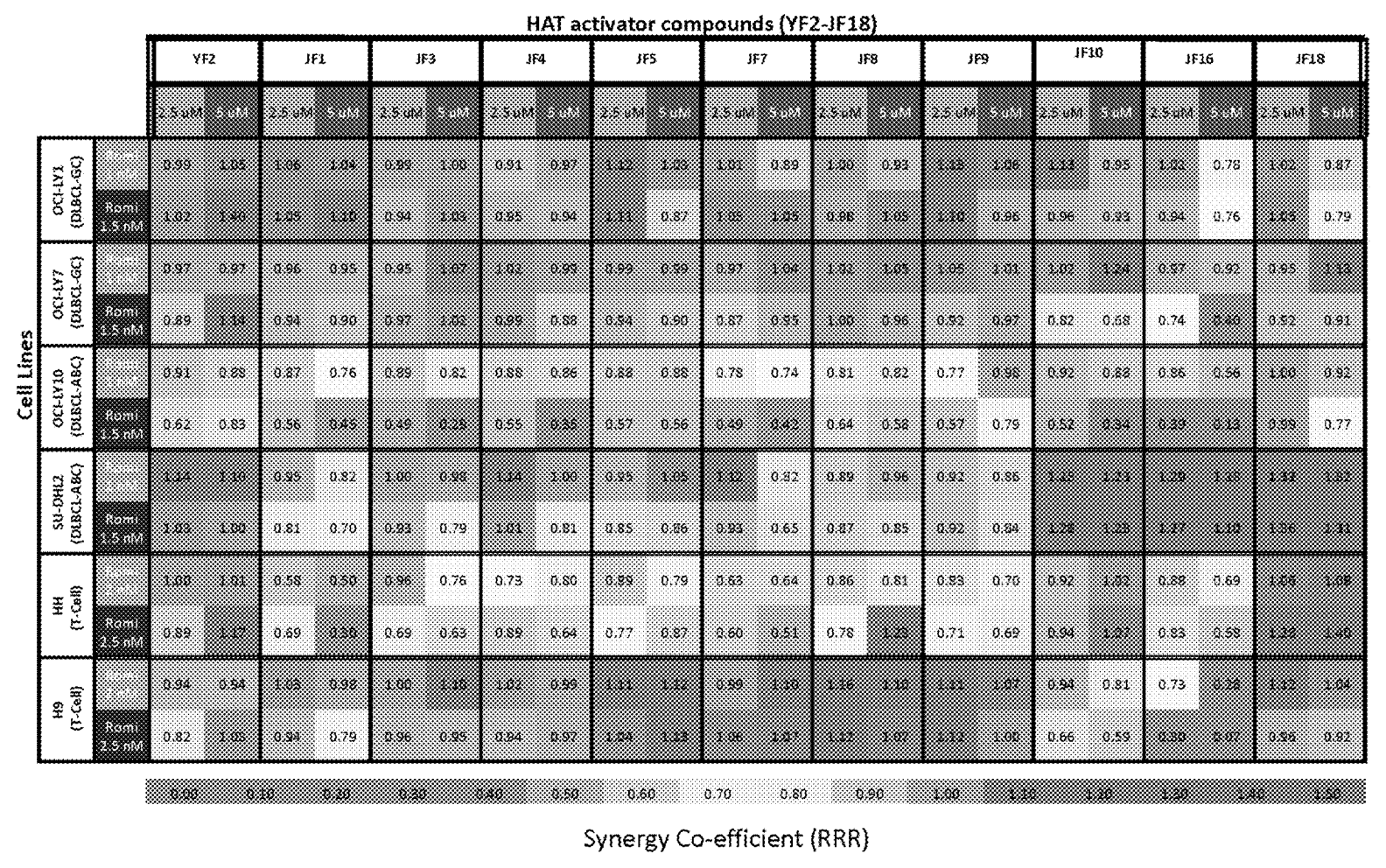
Figure 20D:
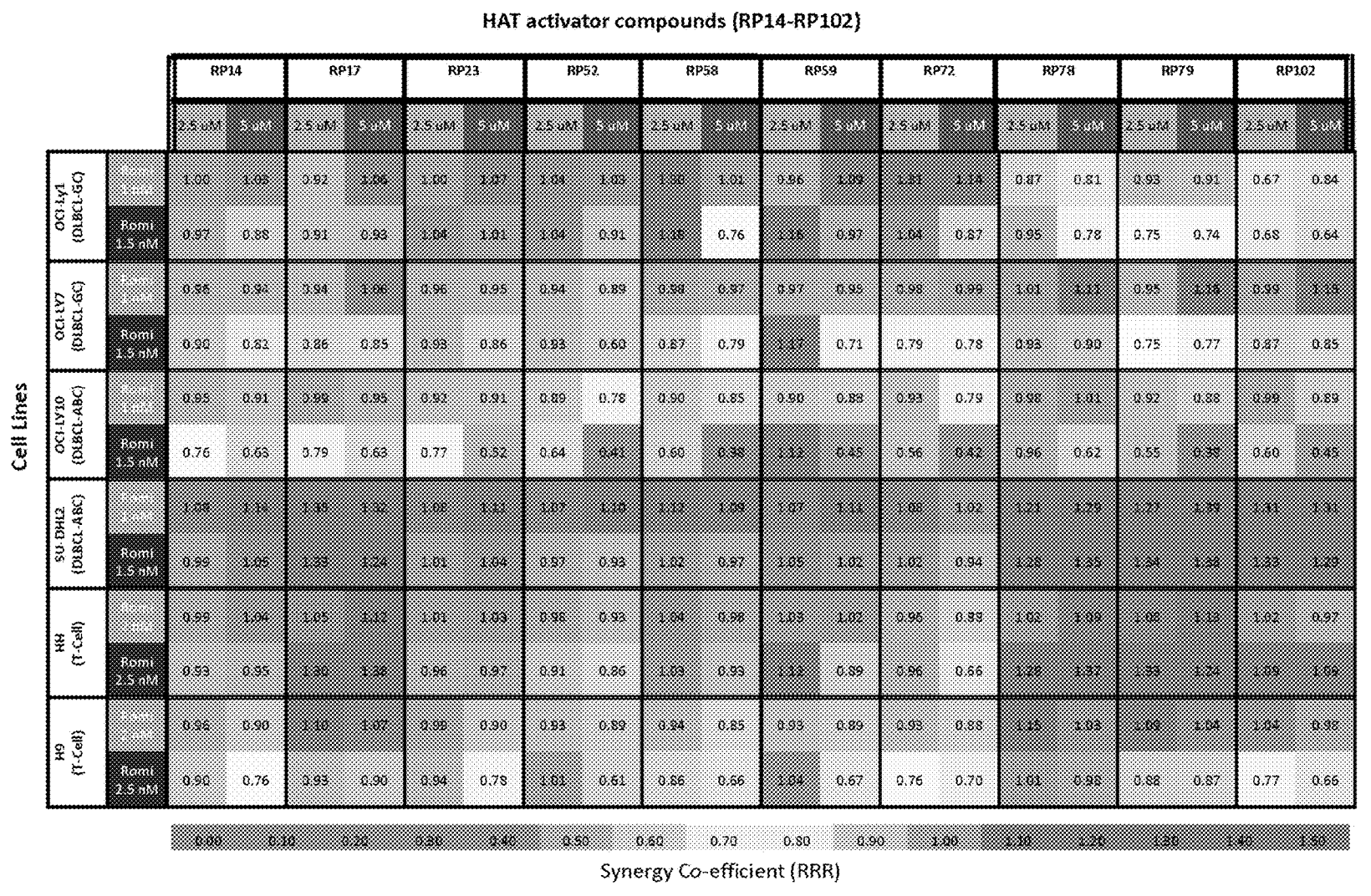

FIGS. 20A-D show the concentration-effect relationship for 21 HAT activator compounds in a panel of non-Hodgkin's lymphoma cell lines at 48 hours. Cell lines tested were germinal center-derived (GC) diffuse large B-cell lymphoma (DLBCL) cell lines (Ly1, Ly7, activated B-cell-derived (ABC) diffuse large B-cell lymphoma (DLBCL) cell lines (Ly10, SU-DHL2), or T-cell lymphoma cell lines (HH, H9). The cells were plated at a concentration of $3\times10^5$ cells/mL in a volume of 1 mL per condition and viability was measured by the cell titer glo assay. Cells were treated with the HAT activators at two concentrations (2.5 uM and 5 uM) for evaluation of the single agent activity. Synergy for 21 HAT activator compounds (YF2, JF1, JF3, JF4, JF5, JF7, JF8, JF9, JF10, JF16, JF18, RP14, RP17, RP23, RP52, RP58, RP59, RP72, RP78, RP79, RP102) with the pan-class histone deacetylase inhibitor, romidepsin, was evaluated at the inhibitory concentrations 10% (1 nM) and 20% (1.5 nM). Synergy coefficients were calculated as the relative risk ratio (RRR). Combinations yielding values RRR<1 are synergistic whereas those yielding RRR>1 are antagonistic, and RRR=1 are additive. FIG. 20A shows the percentage viability of cells treated with HAT activators YF2, JF1, JF3, JF4, JF5, JF7, JF8, JF9, JF10, JF16, JF18 as single agents or in combination with romidepsin at 48 hours. FIG. 20B shows the percentage viability of cells treated with HAT activators RP14, RP17, RP23, RP52, RP58, RP59, RP72, RP78, RP79, RP102 as single agents or in combination with romidepsin at 48 hours. FIG. 20C shows the synergy coefficients calculated as the relative risk ratio (RRR) for cells treated with HAT activators YF2, JF1, JF3, JF4, JF5, JF7, JF8, JF9, JF10, JF16, JF18 as single agents or in combination with romidepsin at 48 hours. FIG. 20D shows the synergy coefficients calculated as the relative risk ratio (RRR) for cells treated with HAT activators RP14, RP17, RP23, RP52, RP58, RP59, RP72, RP78, RP79, RP102 as single agents or in combination with romidepsin at 48 hours.

Figure 22A:
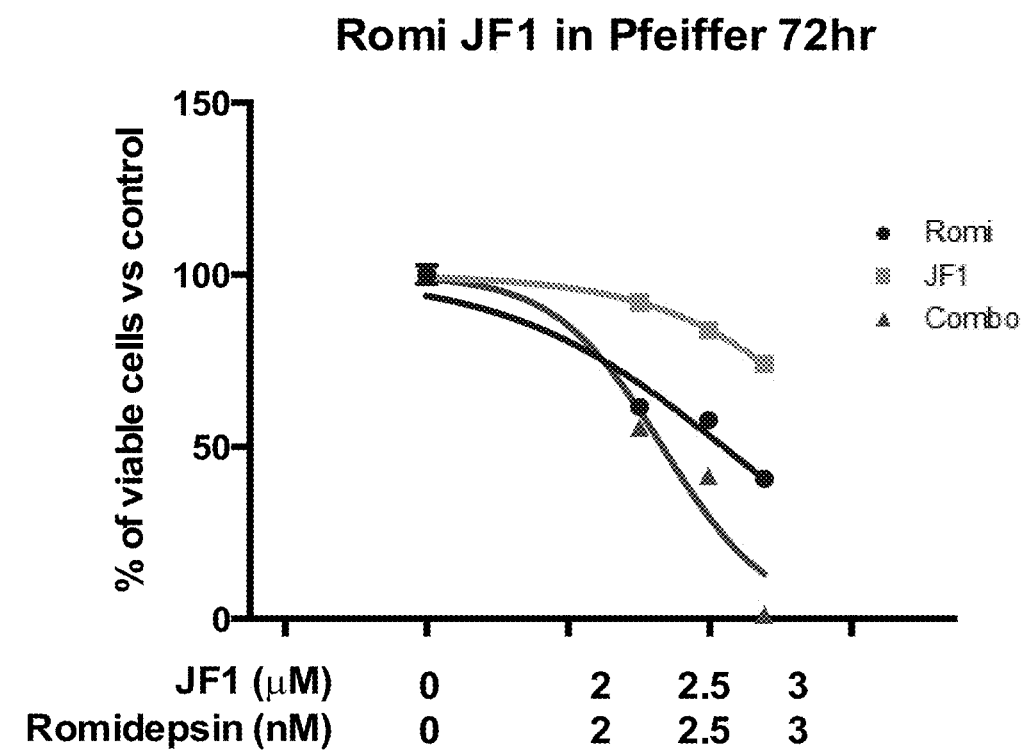
Figure 22B:
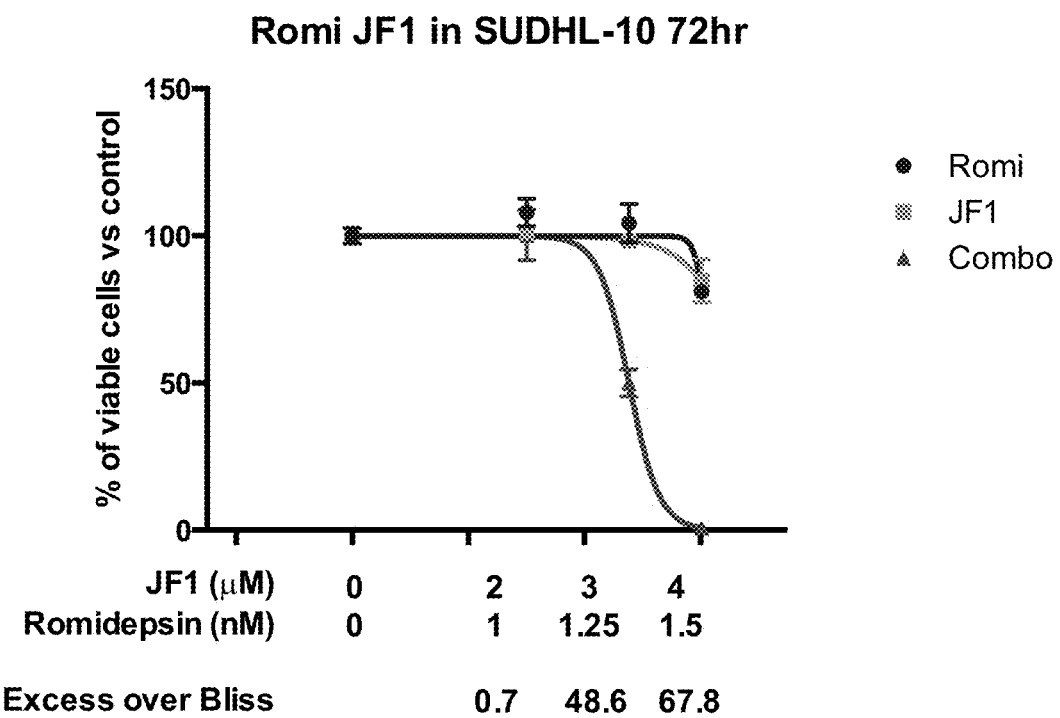
Figure 22C:
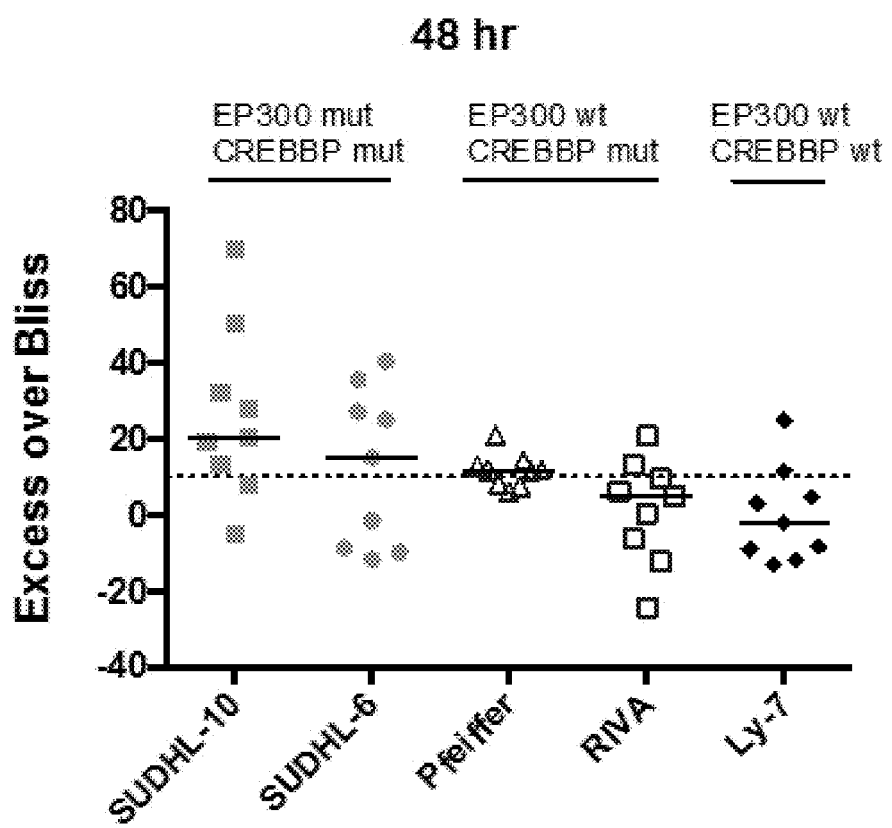
Figure 22D:
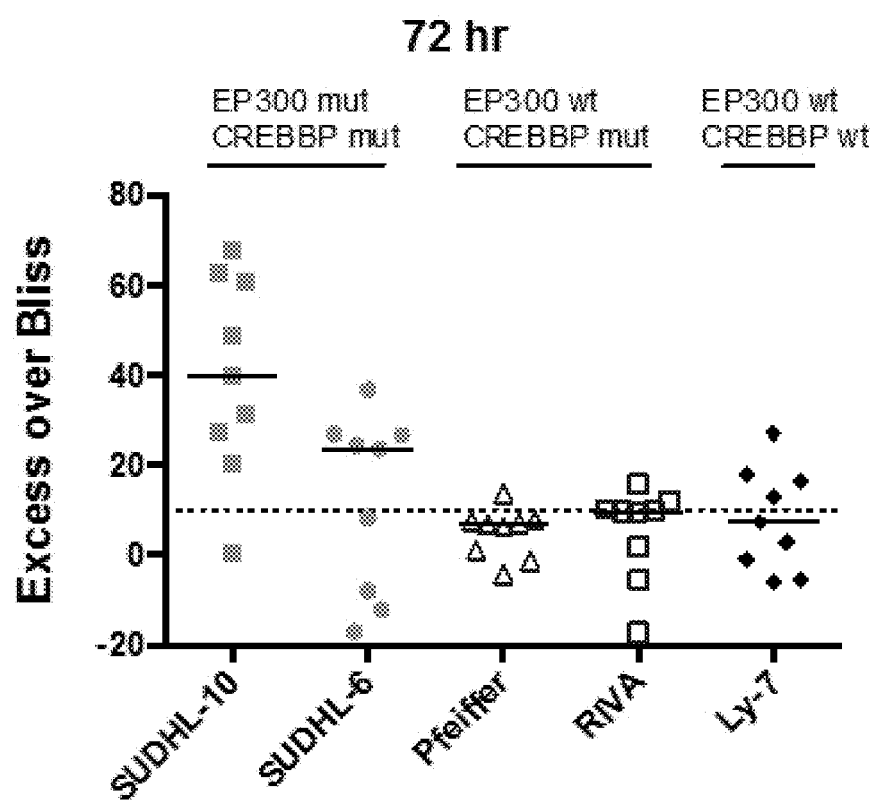
Figure 22E:
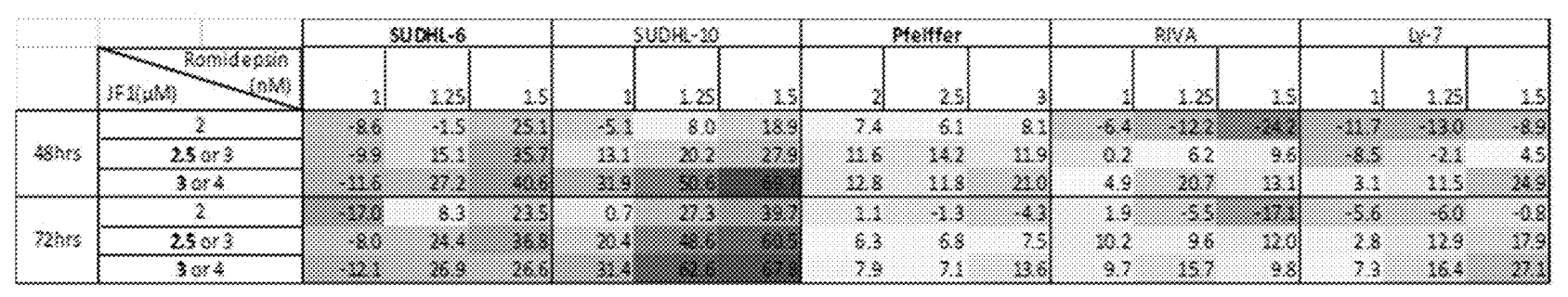

FIGS. 22A-E show the synergy effect of JF1, a HAT activator compound, with romidepsin (a pan-class HDAC inhibitor) in B-cell lymphoma cell lines. Synergy between JF1 and romidepsin was evaluated in Pfeiffer (EP300 wt/CREBBP mut) and SUDHL-10 cells (EP300 mut/CREBBP A). The cells were exposed to increasing concentration of JF1 and romidepsin alone and in combinations as indicated in FIGS. 22A and 22B. Excess Over Bliss was calculated. Drug synergy will be confirmed by Excess over bliss (EOB). Bliss is calculated by the following formula: X=(A+B)−(A*B); where X designates the combined response for the two single compounds with effects (inhibition) A and B. The difference between Bliss and observed growth inhibition (Y) induced by combinations of drugs A and B at the same dose is the termed EOB (EOB=Y−X) 18,19. An EOB>10 connotes synergy. Strong synergy was observed in SUDHL-10, whereas weak synergy was seen in Pfeiffer. Synergy effect of JF1 and romidepsin was also assessed in a panel of B-cell lymphoma cell lines (N=5) (FIGS. 22C-22E). Cells were treated by different concentrations of JF1 and romidepsin for 48 hrs (FIG. 22C) and 72 hrs (FIG. 22D) and an Excess Over Bliss was calculated for both time points for all five cell lines. SUDHL-6 and Pfeiffer (Bold) were treated 2, 2.5, 3 nM JF1, whereas the rest of cell lines were treated with 2, 3, 4 µM JF1. The synergy of JF1 and romidepsin in each cell line and at each time point is indicated in FIG. 22E. Synergy is defined by an Excess Over Bliss of 10. Cell lines with EP300 mutations have stronger synergy than EP300 wildtype (wt) cell lines. Genetic status of the cell lines disclosed in FIGS. 22A-22E are as follows: Pfeiffer: EP300 wt/CREBBP mis mut; SUDHL-10: EP300 mis mut/CREBBP trunc mut; SUDHL-6: EP300 mis mut/CREBBP trunc mut; RIVA: EP300 wt/CREBBP trunc mut; Ly-7: EP300 wt/CREBBP wt.

Figure 23:
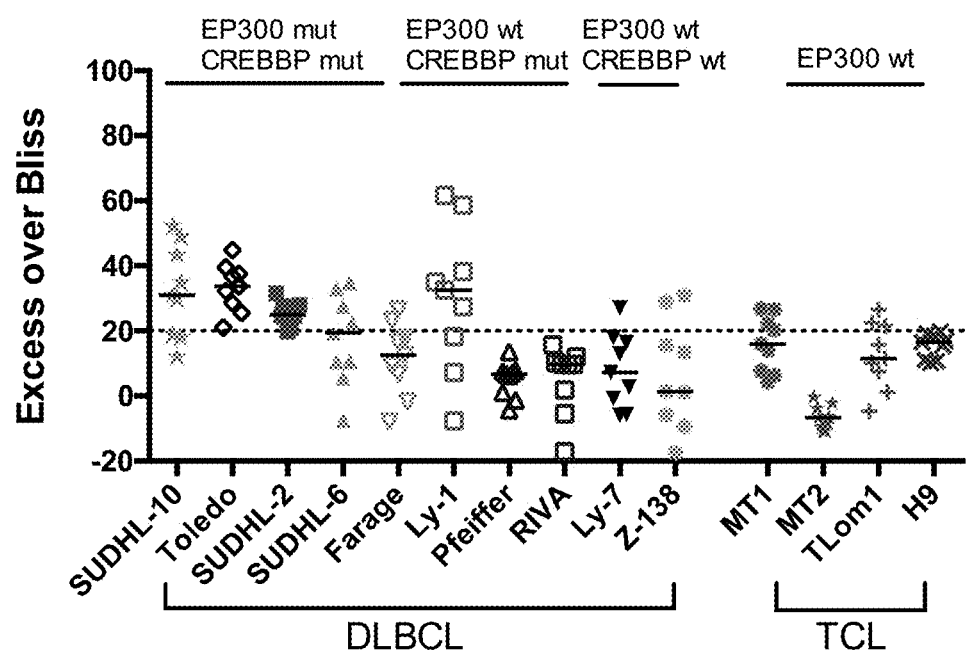
FIG. 23 shows the synergy effect of increasing concentrations of JF1 and romidepsin in ten B-cell lymphoma cell lines and four T-cell lymphoma cell lines alone and in combination at 72 hrs. Strong synergy is defined by an Excess Over Bliss of 20.

FIG. 23 shows the synergy effect of JF1 (a HAT activator compound) with romidepsin (a pan-class HDAC inhibitor) in ten B-cell lymphoma cell lines and four T-cell lymphoma cell lines. Cells were exposed to increasing concentrations of JF1 and romidepsin in various combinations for 72 hrs and Excess Over Bliss (EOB) was calculated. The data illustrates that strong synergy was found in 5 out of 14 cell lines (36%) treated with JF1 in combination with romidepsin, as defined by an EOB of at least 20

Figure 24:
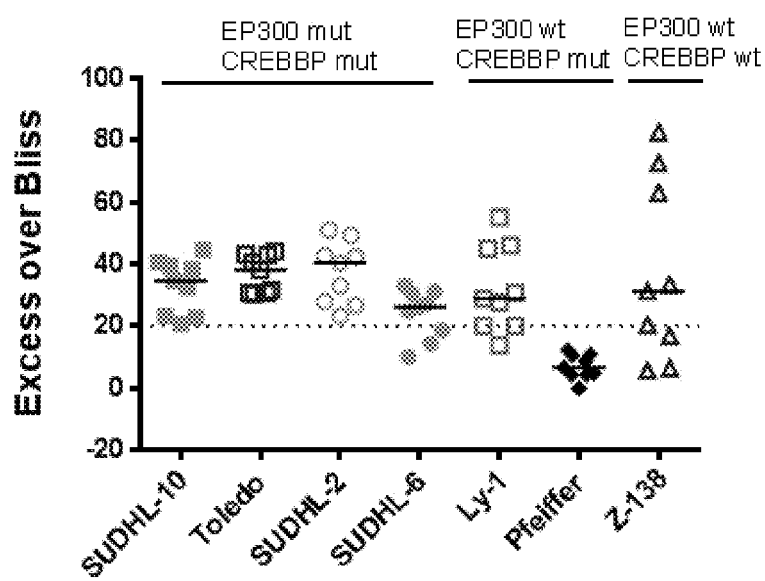
FIG. 24 shows the synergy effect of increasing concentrations of YF2 and romidepsin in seven B-cell lymphoma cell lines alone and in combination at 72 hrs. Strong synergy is defined by an Excess Over Bliss of 20.

FIG. 24 shows the synergy effect of YF2 (a HAT activator compound) with romidepsin (a pan-class HDAC inhibitor) in seven B-cell lymphoma cell lines. Cells were exposed to increasing concentrations of YF2 and romidepsin in various combinations for 72 hrs and Excess Over Bliss (EOB) was calculated. The data illustrates that strong synergy was found in 6 out of 7 cell lines (86%) treated with YF2 in combination with romidepsin, as defined by an EOB of at least 20. Only in Pfeiffer cells did the drug combination fail to show a strong response.

Figure 25A:
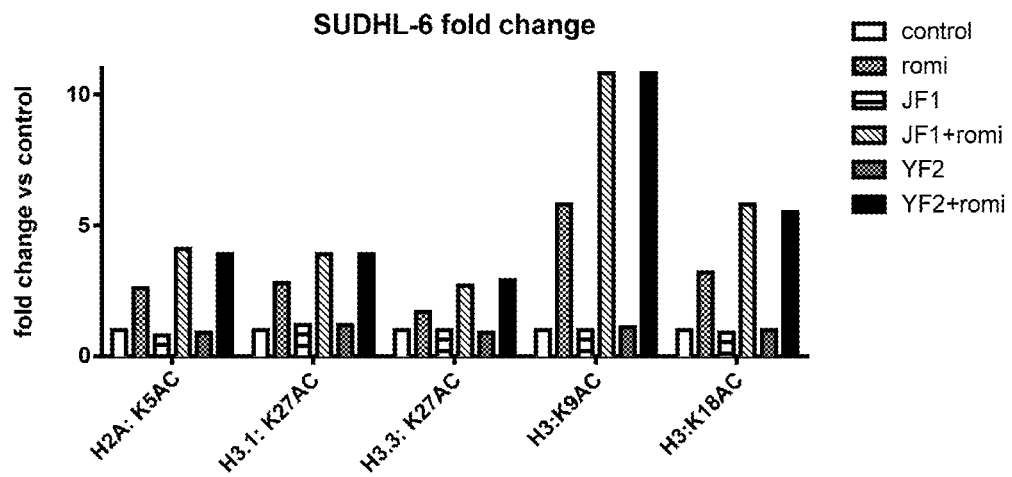
FIGS. 25A-B compare the synergistic effects of JF1 and YF2 on histone acetylation in B-cell lymphoma cell lines alone and in combination at 48 hrs, as quantified by mass spectrometry. The fold changes vs. control for histone acetylation in SUDHL-6 (FIG. 25A) and SUDHL-10 (FIG. 25B) were calculated for five lysine-acetylated histones.
Figure 25B:
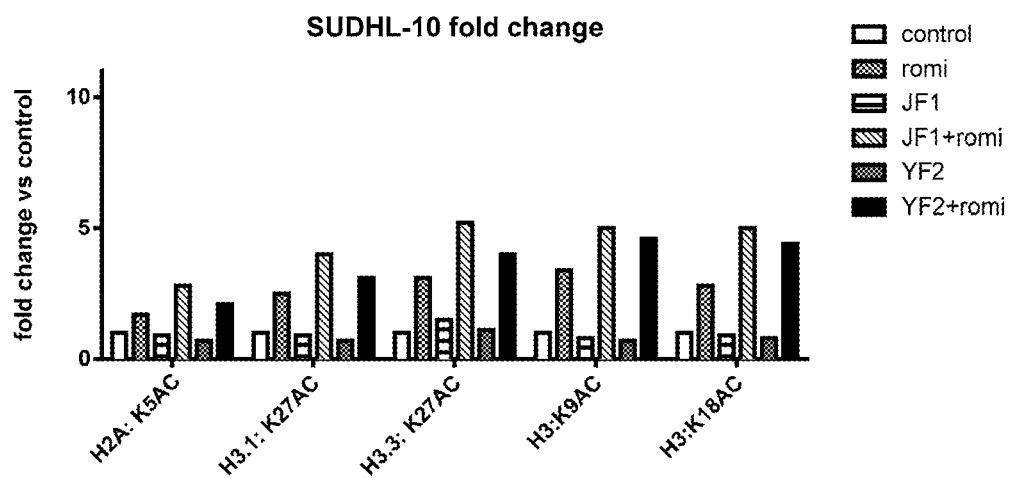

FIGS. 25A-B compare the synergy effects that HAT-activators JF1 and YF2 in combination with romidepsin have on histone acetylation in B-cell lymphoma cell lines, as quantified by mass spectrometry. In these experiments cells were seeded at 5,000 cells/mL and exposed to YF2 (6 uM), JF1 (3 uM) and romidepsin (1.5 nM) alone and in combinations for 48 hours. Following treatment, SUDHL-6 (EP300 mut/CREBBP mut, FIG. 25A) and SUDHL-10 cells (EP300 mut/CREBBP mut, FIG. 25B) were harvested for histone extraction.

Treatment of SUDHL-6 cells with romidepsin, JF1, YF2, JF1/romidepsin, and YF2/romidepsin at the aforementioned concentrations resulted in the extraction of five lysine-acetylated histones: H2A:K5AC, H3.1:K27AC, H3.3:K27AC, H3:K9AC, and H3:K18AC. For each, a synergy effect, calculated as a fold change of treatment vs. control, was observed showing an increase in histone acetylation for JF1/romidepsin and YF2/romidepsin compared to individual treatment of the cells with either JF1, YF2, or romidepsin alone (FIG. 25A). JF1 or YF2 in combination with romidepsin induced the global acetylation of histones compared with single agent effects. In the case of histone H3:K9AC, both combination treatments resulted in a 10-fold increase in acetylation vs. control, which amounted to about a 2-fold increase vs. romidepsin and an 8-fold increase vs. YF2 or JF1 alone.

The synergy trend for the SUDCL-6 cell line is evident for SUDCL-10 as well (FIG. 25B). In the same manner as described above, SUDHL-10 cells were treated separately with romidepsin, JF1, YF2, JF1/romidepsin, and YF2/romidepsin and the fold change in histone acetylation was measured. JF1 or YF2 in combination with romidepsin induced the global acetylation of histones compared with single agent effects. While the JF1/romidepsin combination exhibited a slightly superior synergy effect over YF2/romidepsin when compared to control and romidepsin alone, both combinations demonstrated a synergy effect across all the histones examined in the study. The maximum effect found for H3:K18AC was about a 1.8-fold increase for the JF1/romidepsin combination over romidepsin alone, but similar levels (about 1.6-fold enhancements) were observed for other histones as well. YF2/romidepsin combinations exhibited a maximum synergy effect of about 1.6-fold for H3:K9AC.

Figure 26:
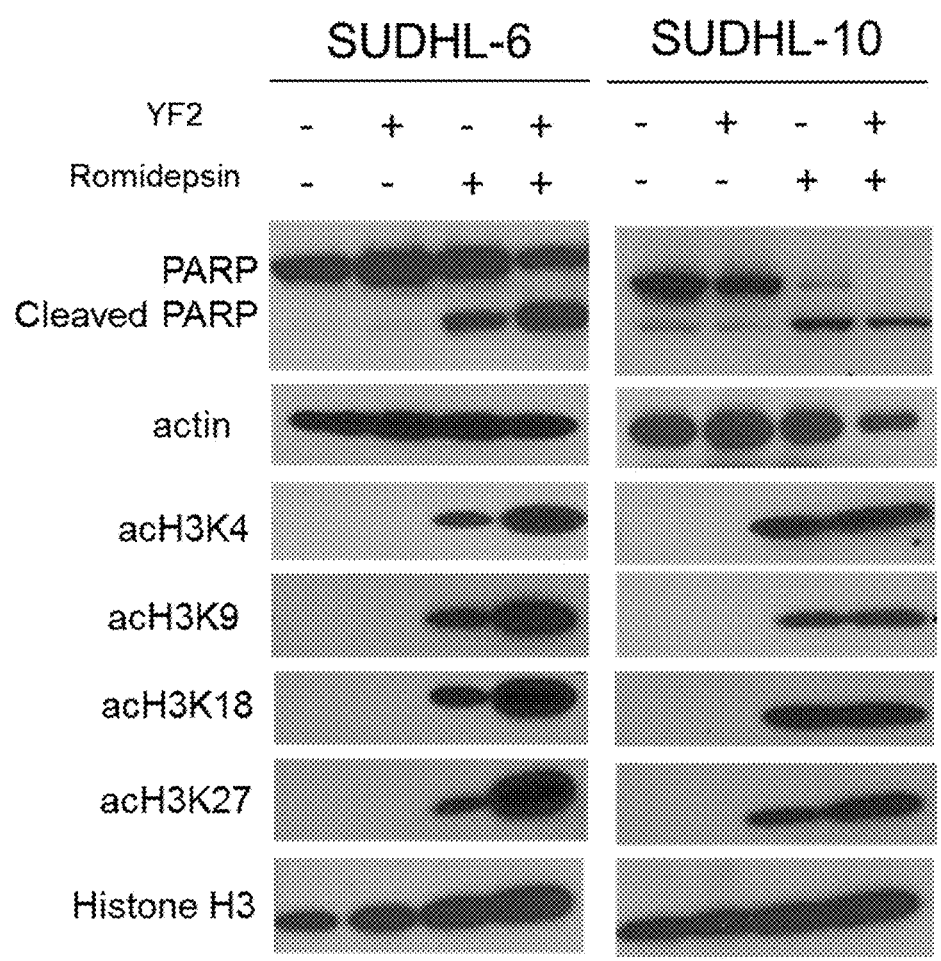
FIG. 26 provides a Western Blot showing the effect of JF1 and YF2 alone and in combination with romidepsin on histone acetylation in HAT-mutated cells lines, SUDHL-6 and SUDHL-10. Cells were exposed to YF2 and romidepsin alone and in combinations for 48 hours in SUDHL-6 and SUDHL-10 (EP300 mut/CREBBP mut).

FIG. 26 provides a Western Blot showing the effect of JF1 and YF2 alone and in combination with romidepsin on histone acetylation in HAT-mutated cells lines. Cells were exposed to YF2 and romidepsin alone and in combinations for 48 hours in SUDHL-6 and SUDHL-10 (EP300 mut/ CREBBP mut). The synergistic effect of YF2 on histone acetylation was evaluated by Western Blot with histone H3 serving as loading control. YF2 in combination with romidepsin induced the global acetylation of Histone H3 compared with single agent effects.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for treating lymphoma in a subject in need thereof, the method comprising administering to the subject a HAT activator and a HDAC inhibitor, wherein the HAT activator is

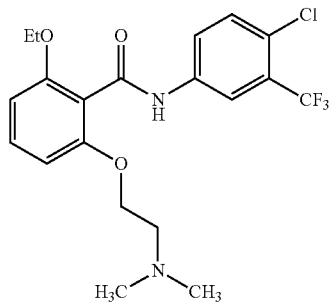 [SMILES: CCOc1cccc(OCCN(C)C)c1C(=O)Nc1ccc(Cl)c(C(F)(F)F)c1]

or a pharmaceutically acceptable salt thereof.

2. The method of claim 1, wherein the HAT activator increases histone acetylation.

3. The method of claim 1, wherein the HDAC inhibitor increases histone acetylation.

4. The method of claim 2, wherein histone acetylation comprises acetylation of histones H2B, H3, H4, or a combination thereof.

5. The method of claim 2, wherein histone acetylation comprises acetylation of histone lysine residues H3K4, H3K9, H3K14, H4K5, H4K8, H4K12, H4K16, or a combination thereof.

6. The method of claim 1, wherein the HAT activator increases p53 acetylation.

7. The method of claim 1, wherein the HDAC inhibitor increases p53 acetylation.

8. The method of claim 1, wherein the HDAC inhibitor is romidepsin, vorinostat, belinostat, panobinostat, entinostat, mocetinostat, abexinostat, quisinostat or gavinostat.

9. The method of claim 1, wherein the HDAC inhibitor is romidepsin or vorinostat.

10. The method of claim 1, wherein the HDAC inhibitor is romidepsin.

11. The method of claim 1, wherein the HDAC inhibitor is chidamide, resminostat, givinostat, or kevetrin.

12. The method of claim 1, wherein the lymphoma is Hodgkin's lymphoma, non-Hodgkin's lymphoma, B cell lymphoma, T cell lymphoma, or follicular lymphoma.

13. The method of claim 12, wherein the B cell lymphoma is diffuse large B-cell lymphoma.

14. The method of claim 13, wherein the diffuse large B-cell lymphoma is a germinal center-derived diffuse large B cell lymphoma, an activated B-cell-derived (ABC) diffuse large B-cell lymphoma, or non-germinal center diffuse large B cell lymphoma.

15. The method of claim 1, wherein the subject has at least one mutant HAT enzyme gene.

16. The method of claim 1, wherein the subject has a wildtype EP300 and wildtype CREBBP gene.

17. The method of claim 1, wherein the subject has a wildtype EP300 and CREBBP mutant gene.

18. The method of claim 17, wherein the mutation is on only one allele of EP300.

19. The method of claim 1, wherein the subject has a mutant EP300 and CREBBP wildtype gene.

20. The method of claim 19, wherein the mutation is on only one allele of EP300.

21. The method of claim 1, wherein the subject has a mutant EP300 and CREBBP mutant gene.

22. The method of claim 21, wherein the mutation is on only one allele of EP300 and on only one allele of CREBBP.

23. The method of claim 1, wherein the HAT activator and a HDAC inhibitor are administered separately.

24. The method of claim 23, wherein the HAT activator and a HDAC inhibitor are administered at different times.

* * * * *

UNITED STATES PATENT AND TRADEMARK OFFICE
CERTIFICATE OF CORRECTION

PATENT NO. : 11,406,608 B2  
APPLICATION NO. : 16/870584  
DATED : August 9, 2022  
INVENTOR(S) : Owen Anthony O'Connor et al.

Page 1 of 1

It is certified that error appears in the above-identified patent and that said Letters Patent is hereby corrected as shown below:

On the Title Page

(72) Inventors Should read: Owen Anthony O'Connor, Scarsdale, NY (US); Jennifer Effie Amengual, Scarsdale, NY (US); Donald W. Landry, New York, NY (US); Ottavio Arancio, New York, NH (US); Luigi Scotto, Stamford, CT (US); Shixian Deng, White Plains, NY (US); Rosa Purgatorio, Bari (IT); Jole Fiorito, Floral Park, NY (US)

Signed and Sealed this  
Twenty-fourth Day of January, 2023

Katherine Kelly Vidal  
*Director of the United States Patent and Trademark Office*